US009803185B2

(12) United States Patent
Wong et al.

(10) Patent No.: US 9,803,185 B2
(45) Date of Patent: Oct. 31, 2017

(54) METHOD FOR CANCER TARGETING TREATMENT AND DETECTION OF ARGININE USING ALBUMIN-BINDING ARGININE DEIMINASE FUSION PROTEIN

(71) Applicant: Vision Global Holdings Ltd., Hong Kong (HK)

(72) Inventors: Bing Lou Wong, Irvine, CA (US); Norman Fung Man Wai, Vancouver (CA); Sui Yi Kwok, Hong Kong (HK); Yun Chung Leung, Hong Kong (HK)

(73) Assignee: Vision Global Holdings Ltd., Hong Kong (HK)

( * ) Notice: Subject to any disclaimer, the term of this patent is extended or adjusted under 35 U.S.C. 154(b) by 0 days.

(21) Appl. No.: 14/981,855

(22) Filed: Dec. 28, 2015

(65) Prior Publication Data

US 2016/0115468 A1 Apr. 28, 2016

Related U.S. Application Data

(63) Continuation-in-part of application No. 14/197,236, filed on Mar. 5, 2014, now Pat. No. 9,255,262.

(51) Int. Cl.
*C12N 9/16* (2006.01)
*C12N 9/78* (2006.01)
*C07K 14/00* (2006.01)
*C12Q 1/34* (2006.01)
*A61K 38/00* (2006.01)

(52) U.S. Cl.
CPC .............. *C12N 9/78* (2013.01); *C07K 14/00* (2013.01); *C12Q 1/34* (2013.01); *A61K 38/00* (2013.01); *C07K 2319/33* (2013.01); *C07K 2319/70* (2013.01); *C12Y 305/03006* (2013.01)

(58) Field of Classification Search
None
See application file for complete search history.

(56) References Cited

U.S. PATENT DOCUMENTS 5,876,969 A * 3/1999 Fleer .................. A61K 38/21
435/252.3
7,569,384 B2 * 8/2009 Rosen .................. C07K 14/765
435/252.3

FOREIGN PATENT DOCUMENTS

| CN | 1634995 A | 7/2005 |
|----|-----------|--------|
| EP | 1987838 A1 | 11/2008 |
| EP | 2295560 A1 | 3/2011 |
| WO | WO00/23580 | * 4/2000 |

OTHER PUBLICATIONS

Ni et al. (Cancer Letters, vol. 261, 2008, pp. 1-11).*
Holtsberg et al. (J. of Controlled Release, 80 (2002), pp. 259-271.*
Syed et al., "Epigenetic status of argininosuccinate synthetase and argininosuccinate lyase modulates autophagy and cell death in glioblastoma", Cell Death and Disease (2013) 4, e458.
Qiu et al., "Arginine Starvation Impairs Mitochondrial Respiratory Function in ASS1-Deficient Breast Cancer Cells", Sci Signal. Apr. 1, 2014;7(319):ra31.
Huang et al., "Arginine deprivation as a new treatment strategy for head and neck cancer", Oral Oncology 48 (2012) 1227-1235.
Miraki-Moud et al., "Arginine deprivation using pegylated arginine deiminase has activity against primary acute myeloid leukemia cells in vivo", Blood First Edition Paper, prepublished online Apr. 20, 2015.
Kelly et al., "Arginine deiminase PEG20 inhibits growth of small cell lung cancers lacking expression of argininosuccinate synthetase", British Journal of Cancer (2012) 106, 324-332.
Delage et al., "Promoter methylation of argininosuccinate synthetase-1 sensitises lymphomas to arginine deiminase treatment, autophagy and caspase-dependent apoptosis", Cell Death and Disease (2012) 3, e342.
Feun et al., "Negative argininosuccinate synthetase expression in melanoma tumours may predict clinical benefit from arginine-depleting therapy with pegylated arginine deiminase", British Journal of Cancer (2012) 106, 1481-1485.
Lan et al., "Deficiency in expression and epigenetic DNA Methylation of ASS1 gene in nasopharyngeal carcinoma: negative prognostic impact and therapeutic relevance", Tumor Biol. (2014) 35:161-169.
Bowles et al., "Pancreatic cancer cell lines deficient in argininosuccinate synthetase are sensitive to arginine deprivation by arginine deiminase", Int. J. Cancer 123, 1950-1955 (2008).
Kim et al., "Arginine Deiminase as a Novel Therapy for Prostate Cancer Induces Autophagy and Caspase-Independent Apoptosis", Cancer Res 2009;69(2):700-8.
Shan et al., "Argininosuccinate synthetase 1 suppression and arginine restriction inhibit cell migration in gastric cancer cell lines", Sci Rep. Apr. 30, 2015;5:9783.
Ensor et al., "Pegylated Arginine Deiminase (ADI-SS PEG20,000 mw) Inhibits Human Melanomas and Hepatocellular Carcinomas in Vitro and in Vivo", Cancer Research 62, 5443-5450, Oct. 1, 2002.
Ashraf S. A. El-Sayed, "Purification, Immobilization, and Biochemical Characterization of L-Arginine Deiminase from Thermophilic Aspergillus fumigatus KJ434941: Anticancer Activity In Vitro", Biotechnol. Prog., 2015, vol. 31, No. 2, pp. 396-405.

(Continued)

*Primary Examiner* — Hope Robinson
(74) *Attorney, Agent, or Firm* — Spruson & Ferguson (HK)

(57) ABSTRACT

The present invention provides a pharmaceutical composition containing albumin-binding arginine deiminase (AAD) fusion protein for treating cancer or other arginine-dependent diseases. The AAD fusion protein can be purified from both soluble and insoluble fractions of crude proteins, binds to human serum albumin (HSA) or animal serum albumin and has its high activity with longer half life for efficient depletion of arginine in cancer cells. The specific activities of wild-type ADI and AAD fusion protein in the present invention are about 20 and about 19 U/mg (at physiological pH 7.4), respectively. The composition can be used alone or in combination with at least one chemotherapeutic agent to give a synergistic effect on cancer treatment and/or inhibiting metastasis. The AAD fusion protein can also be used as a component for detection and quantitative analysis of arginine in a testing kit for various samples including blood, food and analytical samples.

14 Claims, 26 Drawing Sheets

(56) References Cited

OTHER PUBLICATIONS

Guidance for Industry and Reviewers—Estimating the safe starting dose in clinical trials for therapeutics in adult healthy volunteers (2002).
Ni et. al. "Arginine deiminaase, a potential anto-tumor drug", Cancer Letters, NY, US vol. 261, No. 1 Jan. 7, 2008, pp. 1-11.
Roland et. al. "Strategies for extended serum half-life of protein therapeutics", current opinion in Biotechnology, vol. 22, No. 6, 2011, pp. 868-876.
Supplementary European search report of 14760354.2 issued from the EPO on Jun. 22, 2016.

* cited by examiner (A)

Native ADI (B)　　　　　　　AAD fusion protein with two ABD/ ABD1

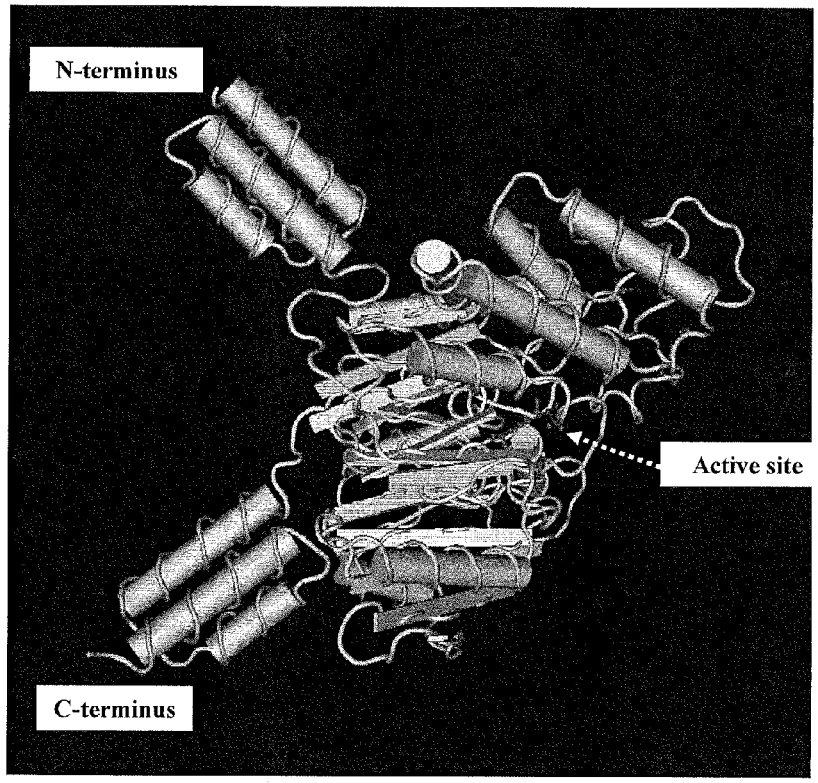

SEQ ID NO: 46
ABD without linker:
LAEAKVLANRELDKYGVSDYYKNLINNAKTVEGVKALIDEILAALP SEQ ID NO: 47
ABD with linker:
AQHDEAVDANSLAEAKVLANRELDKYGVSDYYKNLINNAKTVEGVKALIDEILAALP SEQ ID NO: 48
ABD1 without linker:
LAEAKVLANRELDKYGVSDFYKRLINKAKTVEGVEALKLHILAALP SEQ ID NO: 49
ABD1 with linker:
GSHHHHHHANSLAEAKVLANRELDKYGVSDFYKRLINKAKTVEGVEALKLHILAALP

FIG. 1 (continued)

(C) AAD fusion protein with one ABD/ ABD1 at N-terminus

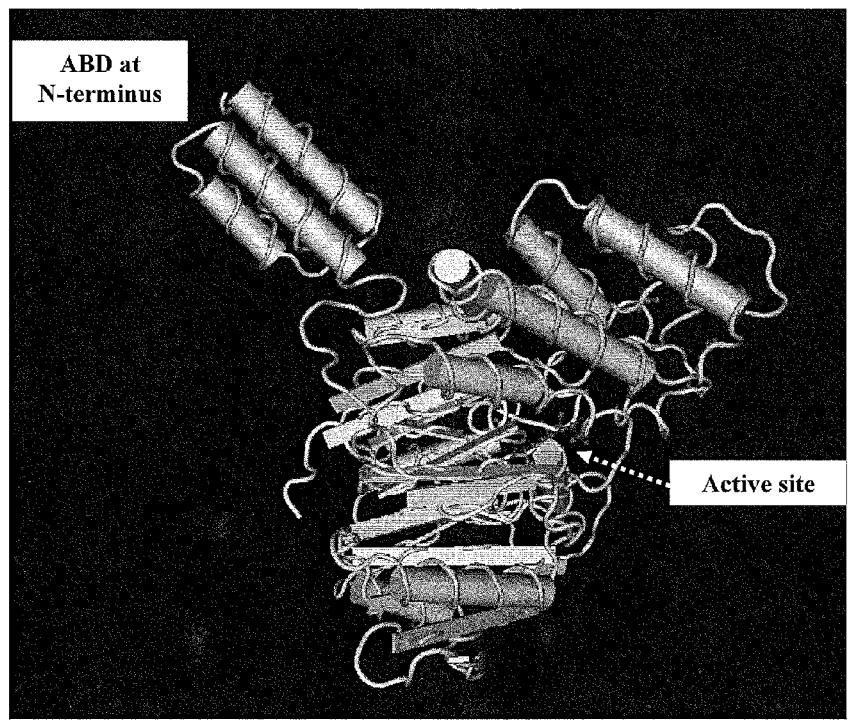

SEQ ID NO: 46
ABD without linker:
LAEAKVLANRELDKYGVSDYYKNLINNAKTVEGVKALIDEILAALP SEQ ID NO: 47
ABD with linker:
AQHDEAVDANSLAEAKVLANRELDKYGVSDYYKNLINNAKTVEGVKALIDEILAALP SEQ ID NO: 48
ABD1 without linker:
LAEAKVLANRELDKYGVSDFYKRLINKAKTVEGVEALKLHILAALP SEQ ID NO: 49
ABD1 with linker:
GSHHHHHHANSLAEAKVLANRELDKYGVSDFYKRLINKAKTVEGVEALKLHILAALP

FIG. 1 (continued)

(D) AAD fusion protein with one ABD/ABD1 at C-terminus

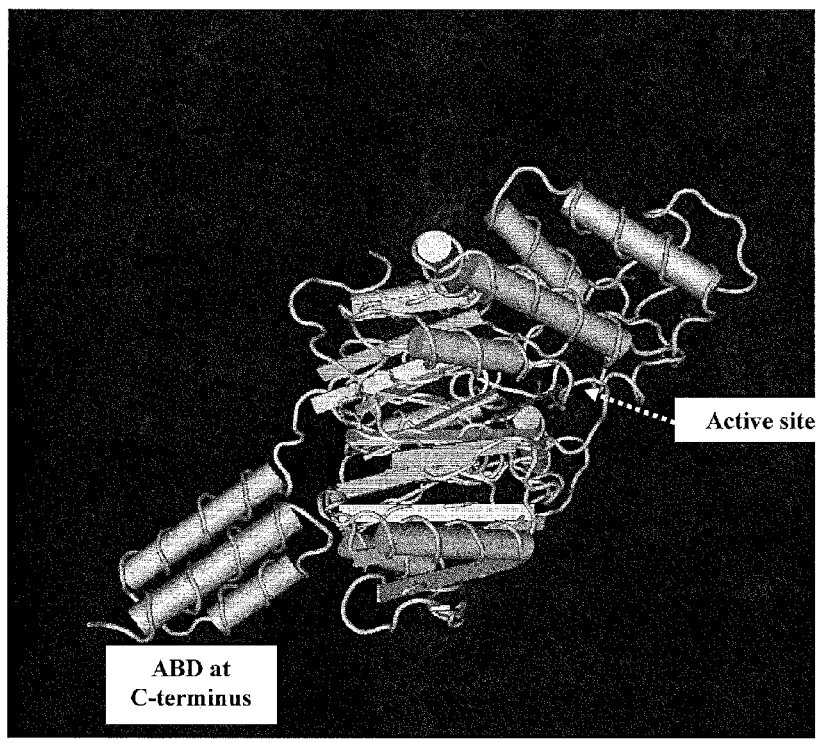

SEQ ID NO: 46
ABD without linker:
LAEAKVLANRELDKYGVSDYYKNLINNAKTVEGVKALIDEILAALP SEQ ID NO: 47
ABD with linker:
AQHDEAVDANSLAEAKVLANRELDKYGVSDYYKNLINNAKTVEGVKALIDEILAALP SEQ ID NO: 48
ABD1 without linker:
LAEAKVLANRELDKYGVSDFYKRLINKAKTVEGVEALKLHILAALP SEQ ID NO: 49
ABD1 with linker:
GSHHHHHHANSLAEAKVLANRELDKYGVSDFYKRLINKAKTVEGVEALKLHILAALP

FIG. 1 (continued)

| | | | |
|---|---|---|---|
| *Mycoplasma arginini* | 1 | MSVFDSKFKGIHVYSEIGELESVLVHPGREIDYITPARLDELLFSAILESHDARKEHKQ | 60 |
| *Lactococcus lactis* | 1 | ------MNNGINVNSEIGKLKSVLLHRPGAEVENITPDTMKQLLFDDIPYLKIAQKEHDF | 54 |
| *Bacillus cereus* | 1 | ------MKHPIHVTSEIGELQTVLLKRPGKEVEKLTPDYLQQLLFDDIPYLPIIQKEHDY | 54 |
| *Bacillus licheniformis* | 1 | ----MIMTTPIHVYSEIGPLKTVMLKRPGRELEKLTPEYLERLLFDDIPFLPAVQKEHDQ | 56 |
| | | *.* **** *::*:::.** *:: :** :..***. * :***. | |

```
                61  FVAELKAKDINVVELIDLVAETYDLASQEAKDKLIEEFLEDSEPVLSEEHKVVVRNFLKA  120
                55  FAQTLRDNGAETVYIENLATEVFEKSSE-TKEEFLSHLLHEAGYRPGRTYDGL-TEYLT-  111
                55  FAQTLRNRGVEVLYLEKLAAEALVDK-K-LREEFVDRILKEGQADVNVAHQTL-KEYLL-  110
                57  FAETLKQQGAEVLYLEKLTAEALDDA-L-VREQFIDELLTESKADINGAYDRL-KEFLL-  112
                    *. *: . :.: : .*..*.             ::::...:* :.         :. :  ::*

121  KKTSRELVEIMMAGITKYDL-----------GIEADHELIVDPMPNLYFTRDPFASVGNG  169
               112  SMPTKDMVEKVYAGVRKNELDIKRTALSDMAGSDAEKYFYLKPLPNAYFTRDPQASMGVG  171
               111  SFSNEELIQKIMGGVRKNEIETSKKTHLYE-LMEDHYPFYLDPMPNLYFTRDPAASVGDQ  169
               113  TFDADSMVEQVMSGIRKNELEREKKSHLHE-LMEDHYPFYLDPMPNLYFTRDPAAAIGSG  171
                    .   .::: : .*; * ::          :  . ;: ::*;** ***** *:;* *

170  VTIHYMRYKVRQBETLFSRFVFSNHPKLIN--TPWYYDPSLKLSIEGGDVFIYNKDTLVV  227
               172  MTINKMTFPARQPESLITEYVMANHPRFKD--TPIWRDRNHTTRIEGGDELILKKTTVAI  229
               170  LTINKMREPARRRESLFMEYIIKYHPRFAKHNVPIWLDRDYKFPIEGGDELILNEETIAI  229
               172  LTINKMKEPARRRESLFMRYIINHHPRFKGHEIPVWLDRDFKFRIEGGDELVLNEETVAI  231
                    :**. *   .*: *:*: .::: **::      * : * . .  ***** :: *: *:.:

228  GVSERTDLQTVTLLAKNIVANKECEFKRIVAINVPKWTNLMHLDTWLTMLDKDKFLYSPI  287
               230  GVSERTSSKTIQNLAKELFANPLSTFDTVLAVEIPHNHAMMHLDTVFTMINHDQFTVFPG  289
               230  GVSARTSAKAIERLAKNLFSRQ-NKIKKVLAIEIPKCRAFMHLDTVFTMVDYDKFTIHPA  288
               232  GVSERTTAQAIERLVRNLFQRQ-SRIRRVLAVEIPKSRAFMHLDTVFTMVDRDQFTIHPA  290
                    *** **  ::: *.:::. ,    :  ::*:::*:  :***** :**:: *:*   *

288  ANDVFKFWDYDLVNGGAEFQP--VENGLPLEGLLQSIINKKPVLIPIAGEGASQMEIERE  345
               290  IMDGAGNINVFILRPGQDG-EVEIEHLTDLKAALKKVLNLSELDL-IECGAGDPIAAPRE  347
               289  IQGPKGKMNIYILEKGADEETLKITHRTSLMEALKEVLDLSELVL-IPCGGGDVIASARE  347
               291  IQGPEGDMRIFVLERGKTADEIHTTEEHNLPEVLKRTLGLSDVKL-IFCGGGDEIASARE  349
                      ::. *                 . *  *::  :  .: :*   ...: **

346  THFDGTNYLAIRPGVVIGYSRNEKTNAALEAAGIKVLPFHGNQLSLGMGNARCMSMPLSR  405
               349  QWNDGSNTLAIAPGEIVTYDRNYVTVELLKEHGIKVHEILSSELGRGRGGARCMSQPLWR  407
               348  QWNDGSNTLAIAPGVVVTYDRNYVSNTLLREHGIEVIEVLSSELSRGRGGPRCMSMPIVR  407
               350  QWNDGSNTLAIAPGVVVTYDRNYISNECLREQGIKVIEIPSGELSRGRGGPRCMSMPLYR  409
                    **:*  ***  **  ::  *.**   :   *.  **:*:   . . :*. * *  **** *: *

406  KDVKW  410
               408  EDL--  410
               408  KDI--  410
               410  EDVK-  413
                    :*:
```

FIG. 2

(A) SEQ ID NO: 36

ADI- ... -ABD 1

MSVFDSKFKGIHVYSEIGELESVLVHEPGREIDYITPARLDELLFSAILESHDARKEHKQ
FVAELKANDINVVELIDLVAETYDLASQEAKDKLIEEFLEDSEPVLSEEHKVVVRNFLKA
KKTSRELVEIMMAGITKYDLGIEADHELIVDPMPNLYFTRDPFASVGNGVTIHYMRYKVR
QRETLFSRFVFSNHPKLINTPWYYDPSLKLSIEGGDVFIYNNDTLVVGVSERTDLQTVTL
LAKNIVANKECEFKRIVAINVPKWTNLMHLDTWLTMLDKDKFLYSPIANDVFKFWDYDLV
NGGAEPQPVENGLPLEGLLQSIINKKPVLIPIAGEGASQMEIERETHFDGTNYLAIRPGV
VIGYSRNEKTNAALEAAGIKVLPFHGNQLSLGMGNARCMSMPLSRKDVKW<u>............
.LAEAKVLANRELDKYGVSDFYKRLINKAKTVEGVEALKLHILAALP</u>

*(ABD 1: high affinity albumin binding domain; the linker is underlined.)*

Linker 1 (SEQ ID NO: 50): GSHHHHHHANS (B) SEQ ID NO: 37

ADI- ... -ABD

MSVFDSKFKGIHVYSEIGELESVLVHEPGREIDYITPARLDELLFSAILESHDARKEHKQ
FVAELKANDINVVELIDLVAETYDLASQEAKDKLIEEFLEDSEPVLSEEHKVVVRNFLKA
KKTSRELVEIMMAGITKYDLGIEADHELIVDPMPNLYFTRDPFASVGNGVTIHYMRYKVR
QRETLFSRFVFSNHPKLINTPWYYDPSLKLSIEGGDVFIYNNDTLVVGVSERTDLQTVTL
LAKNIVANKECEFKRIVAINVPKWTNLMHLDTWLTMLDKDKFLYSPIANDVFKFWDYDLV
NGGAEPQPVENGLPLEGLLQSIINKKPVLIPIAGEGASQMEIERETHFDGTNYLAIRPGV
VIGYSRNEKTNAALEAAGIKVLPFHGNQLSLGMGNARCMSMPLSRKDVKW<u>AQHDEAVDAN
S</u>LAEAKVLANRELDKYGVSDYYKNLINNAKTVEGVKALIDEILAALP

*(ABD: albumin binding domain; the linker is underlined.)*

Linker 2 (SEQ ID NO: 51): AQHDEAVDANS

FIG. 3

(C) SEQ ID NO: 38

MSVFDSKFKGIHVYSEIGELESVLVHEPGREIDYITPARLDELLFSAILESHDARKEHKQ
FVAELKANDINVVELIDLVAETYDLASQEAKDKLIEEFLEDSEPVLSEEHKVVVRNFLKA
KKTSRELVEIMMAGITKYDLGIEADHELIVDPMPNLYFTRDPFASVGNGVTIHYMRYKVR
QRETLFSRFVFSNHPKLINTPWYYDPSLKLSIEGGDVFIYNNDTLVVGVSERTDLQTVTL
LAKNIVANKECEFKRIVAINVPKWTNLMHLDTWLTMLDKDKFLYSPIANDVFKFWDYDLV
NGGAEPQPVENGLPLEGLLQSIINKKPVLIPIAGEGASQMEIERETHFDGTNYLAIRPGV
VIGYSRNEKTNAALEAAGIKVLPFHGNQLSLGMGNARCMSMPLSRKDVKWHHHHHHAQHD
EAVDANSLAEAKVLANRELDKYGVSDYYKNLINNAKTVEGVKALIDEILAALP

*(ABD: albumin binding domain; the linker is underlined.)*

(D) SEQ ID NO: 39

MSVFDSKFKGIHVYSEIGELESVLVHEPGREIDYITPARLDELLFSAILESHDARKEHKQ
FVAELKANDINVVELIDLVAETYDLASQEAKDKLIEEFLEDSEPVLSEEHKVVVRNFLKA
KKTSRELVEIMMAGITKYDLGIEADHELIVDPMPNLYFTRDPFASVGNGVTIHYMRYKVR
QRETLFSRFVFSNHPKLINTPWYYDPSLKLSIEGGDVFIYNNDTLVVGVSERTDLQTVTL
LAKNIVANKECEFKRIVAINVPKWTNLMHLDTWLTMLDKDKFLYSPIANDVFKFWDYDLV
NGGAEPQPVENGLPLEGLLQSIINKKPVLIPIAGEGASQMEIERETHFDGTNYLAIRPGV
VIGYSRNEKTNAALEAAGIKVLPFHGNQLSLGMGNARCMSMPLSRKDVKWAQHDEAVDAN
SLAEAKVLANRELDKYGVSDYYKNLINNAKTVEGVKALIDEILAALPHHHHHH

*(ABD: albumin binding domain; the linker is underlined.)*

FIG. 3 (continued)

(E)  SEQ ID NO: 40

MHHHHHHDEAVDANSLAEAKVLANRELDKYGVSDYYKNLINNAKTVEGVKALIDEILAAL
PSGSNNNNNNGSGGSVFDSKFKGIHVYSEIGELESVLVHEPGREIDYITPARLDELLFSA
ILESHDARKEHKQFVAELKANDINVVELIDLVAETYDLASQEAKDKLIEEFLEDSEPVLS
EEHKVVVRNFLKAKKTSRELVEIMMAGITKYDLGIEADHELIVDPMPNLYFTRDPFASVG
NGVTIHYMRYKVRQRETLFSRFVFSNHPKLINTPWYYDPSLKLSIEGGDVFIYNNDTLVV
GVSERTDLQTVTLLAKNIVANKECEFKRIVAINVPKWTNLMHLDTWLTMLDKDKFLYSPI
ANDVFKFWDYDLVNGGAEPQPVENGLPLEGLLQSIINKKPVLIPIAGEGASQMEIERETH
FDGTNYLAIRPGVVIGYSRNEKTNAALEAAGIKVLPFHGNQLSLGMGNARCMSMPLSRKD
VKW

*(ABD: albumin binding domain; the linker between His and ABD is underlined with solid line while the linker between Poly-N and ADI is underlined with dotted line.)*

Linker 3 (SEQ ID NO: 52): DEAVDANS; Linker 4: SGS; Linker 5 (SEQ ID NO: 53): GSGG

FIG. 3 (continued)

(F) SEQ ID NO: 41

MGHHHHHHDEAVDANSLAEAKVLANRELDKYGVSDYYKNLINNAKTVEGVKALIDEILAALPSG
SNNNNNNGSGGKHPIHVTSEIGELQTVLLKRPGKEVENLTPDYLQQLLFDDIPYLPIIQKEHDY
FAQTLRNRGVEVLYLEKLAAEALVDKKLREEFVDRILKEGQADVNAHQTLKEYLLSFSNEELI
QKIMGGVRKNEIETSKKTHLYELMEDHYPFYLDPMPNLYFTRDPAASVGDGLTINKMREPARRR
ESLFMEYIIKYHPRFAKHNVPIWLDRDYKFPIEGGDELILNEETIAIGVSARTSAKAIERLAKN
LFSRQNKIKKVLAIEIPKCRAFMHLDTVFTMVDYDKFTIHPAIQGPKGNMNIYILEKGADEETL
KITHRTSLMEALKEVLDLSELVLIPCGGGDVIASAREQWNDGSNTLAIAPGVVVTYDRNYVSNT
LLREHGIEVIEVLSSELSRGRGGPRCMSMPIVRKDI

*(ABD: albumin binding domain; the linker between His and ABD is underlined with solid line while the linker between Poly-N and bcADI is underlined with dotted line.)*

Linker 3 (SEQ ID NO: 52): DEAVDANS; Linker 4: SGS; Linker 5 (SEQ ID NO: 53): GSGG

FIG. 3 (continued)

(A) SEQ ID NO: 42

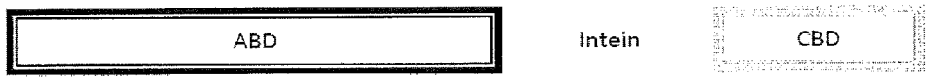

MAQHDEAVDANSLAEAKVLANRELDKYGVSDYYKNLINNAKTVEGVKALIDEILAALPEF
LEGSSCITGDALVALPEGESVRIADIVPGARPNSDNAIDLKVLDRHGNPVLADRLFHSGE
HPVYTVRTVEGLRVTGTANHPLLCLVDVAGVPTLLWKLIDEIKPGDYAVIQRSAFSVDCA
GFARGKPEFAPTTYTVGVPGLVRFLEAHHRDPDAQAIADELTDGRFYYAKVASVTDAGVQ
PVYSLRVDTADHAFITNGFVSHATGLTGLNSGLTTNPGVSAWQVNTAYTAGQLVTYNGKT
YKCLQPHTSLAGWEPSNVPALWQLQGDPITITITK (B) SEQ ID NO: 43

MKIEEGKLTNPGVSAWQVNTAYTAGQLVTYNGKTYKCLQPHTSLAGWEPSNVPALWQLQNNG
NNGLELRESGAISGDSLISLASTGKRVSIKDLLDEKDFEIWAINEQTMKLESAKVSRVFCTG
KKLVYILKTRLGRTIKATANHRFLTIDGWKRLDELSLKEHIALPRKLESSSLQLSPEIEKLS
QSDIYWDSIVSITETGVEEVFDLTVPGPHNFVANDIIVHNCSVFDSKFKGIHVYSEIGELES
VLVHEPGREIDYITPARLDELLFSAILESHDARKEHKQFVAELKANDINVVELIDLVAETYD
LASQEAKDKLIEEFLEDSEPVLSEEHKVVVRNFLKAKKTSRELVEIMMAGITKYDLGIEADH
ELIVDPMPNLYFTRDPFASVGNGVTIHYMRYKVRQRETLFSRFVFSNHPKLINTPWYYDPSL
KLSIEGGDVFIYNNDTLVVGVSERTDLQTVTLLAKNIVANKECEFKRIVAINVPKWTNLMHL
DTWLTMLDKDKFLYSPIANDVFKFWDYDLVNGGAEPQPVENGLPLEGLLQSIINKKPVLIPI
AGEGASQMEIERETHFDGTNYLAIRPGVVIGYSRNEKTNAALEAAGIKVLPFHGNQLSLGMG
NARCMSMPLSRKDVKW

FIG. 4

(C) C-Terminal fusion
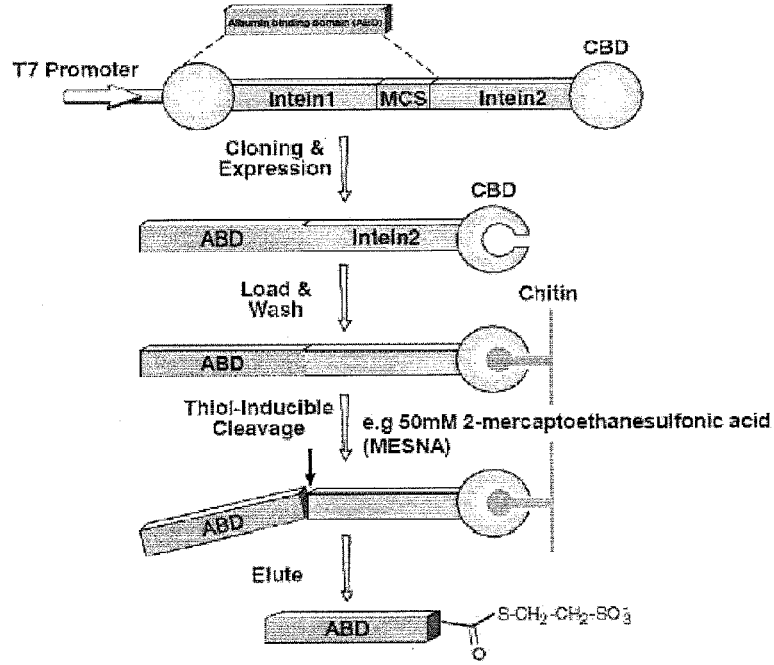
(D) N-Terminal fusion
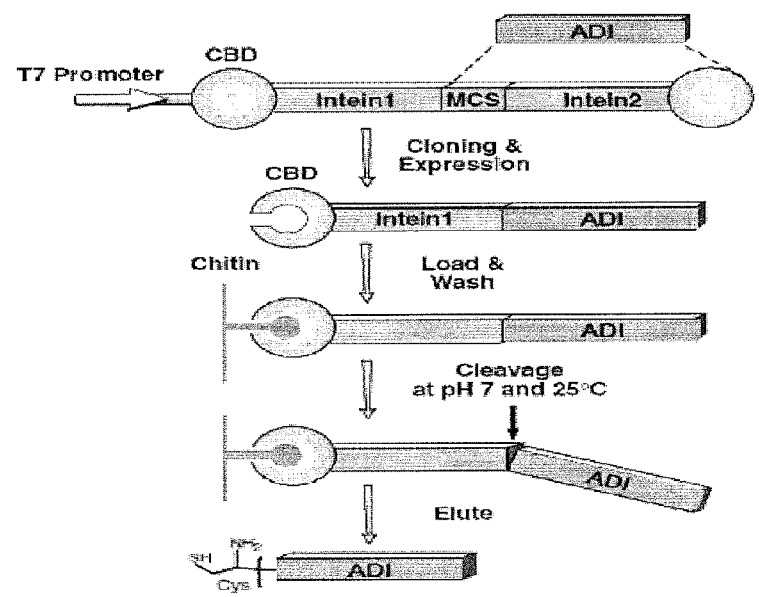
FIG. 4 (continued)

(E)

(A) GENE MAP

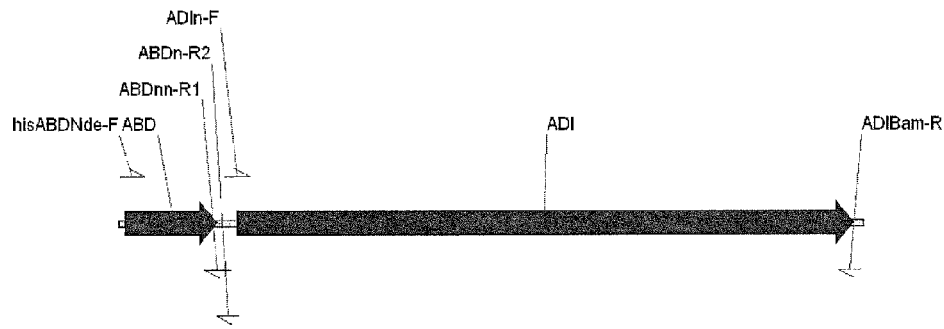

(B) Nucleotide sequence of His-ABD-PolyN–ADI (1484 bp):

(SEQ ID NO: 44)

```
5'-
ATGCATCATCACCATCACCATGATGAAGCCGTGGATGCGAATTCCTTAGCTGAAGCTAAAGTCT
TAGCTAACAGAGAACTTGACAAATATGGAGTAAGTGACTATTACAAGAACCTAATCAACAATGC
CAAAACTGTTGAAGGTGTAAAAGCACTGATAGATGAAATTTTAGCTGCATTACCTTCGGGTAGT
AACAACAATAATAACAATGGTAGCGGCGGTTCTGTATTTGACAGTAAATTTAAAGGAATTCACG
TTTATTCAGAAATTGGTGAATTAGAATCAGTTCTAGTTCACGAACCAGGACGCGAAATTGACTA
TATTACACCAGCTAGACTAGATGAATTATTATTCTCAGCTATCTTAGAAAGCCACGATGCTAGA
AAAGAACACAAACAATTCGTAGCAGAATTAAAAGCAAACGACATCAATGTTGTTGAATTAATTG
ATTTAGTTGCTGAAACATATGATTTAGCATCACAAGAAGCTAAAGACAAATTAATCGAAGAATT
TTTAGAAGACTCAGAACCAGTTCTATCAGAAGAACACAAAGTAGTTGTAAGAAACTTCTTAAAA
GCTAAAAAAACATCAAGAGAATTAGTAGAAATCATGATGGCAGGGATCACAAAATACGATTTAG
GTATCGAAGCAGATCACGAATTAATCGTTGACCCAATGCCAAACCTATACTTCACACGTGACCC
ATTTGCATCAGTAGGTAATGGTGTAACAATCCACTACATGCGTTACAAAGTTAGACAACGTGAA
ACATTATTCTCAAGATTTGTATTCTCAAATCACCCTAAACTAATTAACACTCCATGGTACTACG
ACCCTTCACTAAAATTATCAATCGAAGGTGGGGACGTATTTATCTACAACAATGACACATTAGT
AGTTGGTGTTTCTGAAAGAACTGACTTACAAACAGTTACTTTATTAGCTAAAAACATTGTTGCT
AATAAAGAATGTGAATTCAAACGTATTGTTGCAATTAACGTTCCAAAATGGACAAACTTAATGC
ACTTAGACACATGGCTAACAATGTTAGACAAGGACAAATTCCTATACTCACCAATCGCTAATGA
CGTATTTAAATTCTGGGATTATGACTTAGTAAACGGTGGAGCAGAACCACAACCAGTTGAAAAC
GGATTACCTCTAGAAGGATTATTACAATCAATCATTAACAAAAAACCAGTTTTAATTCCTATCG
CAGGTGAAGGTGCTTCACAAATGGAAATCGAAAGAGAAACACACTTCGATGGTACAAACTACTT
AGCAATTAGACCAGGTGTTGTAATTGGTTACTCACGTAACGAAAAAACAAACGCTGCTCTAGAA
GCTGCAGGCATTAAAGTTCTTCCATTCCACGGTAACCAATTATCATTAGGTATGGGTAACGCTC
GTTGTATGTCAATGCCTTTATCACGTAAAGATGTTAAGTGGTAA-3'
```

FIG. 6

(C) Amino acid sequence of His-ABD-PolyN–ADI:

(SEQ ID NO: 40)

M<u>HHHHHH</u>DEAVDANSLAEAKVLANRELDKYGVSDYYKNLINNAKTVEGVKALIDEILAALP<u>SGSNNNNNNGSGG</u>SVF

DSKFKGIHVYSEIGELESVLVHEPGREIDYITPARLDELLFSAILESHDARKEHKQFVAELKANDINVVELIDLVAET

YDLASQEAKDKLIEEFLEDSEPVLSEEHKVVVRNFLKAKKTSRELVEIMMAGITKYDLGIEADHELIVDPMPNLYFTR

DPFASVGNGVTIHYMRYKVRQRETLFSRFVFSNHPKLINTPWYYDPSLKLSIEGGDVFIYNNDTLVVGVSERTDLQTV

TLLAKNIVANKECEFKRIVAINVPKWTNLMHLDTWLTMLDKDKFLYSPIANDVFKFWDYDLVNGGAEPQPVENGLPLE

GLLQSIINKKPVLIPIAGEGASQMEIERETHFDGTNYLAIRPGVVIGYSRNEKTNAALEAAGTKVLPFHGNQLSLGMG

NARCMSMPLSRKDVKW (PolyN with linker: <u>SGSNNNNNNGSGG</u>)

FIG. 6 (continued)

(A) GENE MAP

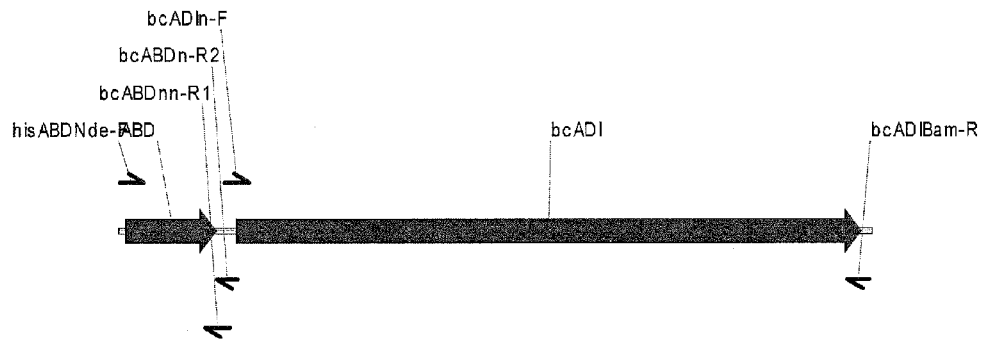

(B) The nucleotide sequence of His-ABD-PolyN–bcADI (1512 bp):

(SEQ ID NO: 45)

```
5'-
ATGGGTCATCATCACCATCACCATGATGAAGCCGTGGATGCGAACAGCTTAGCTGAAGCTAAAG
TCTTAGCTAACAGAGAACTTGACAAATATGGAGTAAGTGACTATTACAAGAACCTAATCAACAA
TGCCAAAACTGTTGAAGGTGTAAAAGCACTGATAGATGAAATTTTAGCTGCATTACCTTCGGGT
AGTAACAACAATAATAACAATGGTAGCGGCGGTAAACATCCGATACATGTTACTTCAGAAATTG
GGGAATTACAAACGGTTTTATTAAAACGACCGGGTAAAGAAGTGGAAAACTTGACGCCAGATTA
TTTGCAGCAATTATTATTTGACGATATTCCATACCTACCAATTATTCAAAAAGAGCATGATTAT
TTTGCACAAACGTTACGCAATCGGGGTGTTGAAGTTCTTTATTTAGAAAAACTAGCCGCTGAGG
CGTTAGTAGATAAAAAACTTCGAGAAGAATTTGTTGATCGTATTTTAAAAGAAGGACAGGCCGA
CGTAAATGTTGCACATCAAACTTTAAAAGAATATTTACTTTCCTTTTCAAATGAAGAATTAATT
CAAAAAATTATGGGCGGTGTACGGAAAAACGAAATTGAAACAAGTAAGAAGACACATTTATATG
AATTAATGGAAGATCATTATCCGTTTTACTTAGATCCAATGCCTAATTTATATTTTACTCGTGA
TCCAGCAGCTAGCGTGGGCGATGGCTTAACGATAAATAAGATGAGAGAACCAGCGCGTAGACGT
GAATCATTATTCATGGAGTACATCATTAAATATCATCCAAGATTTGCAAAACATAATGTACCAA
TCTGGTTAGATCGTGATTATAAATTTCCAATTGAAGGTGGCGACGAGCTAATTTTAAATGAAGA
AACAATTGCGATTGGAGTATCTGCTCGTACTTCAGCTAAAGCAATTGAACGTTTAGCAAAAAAT
CTCTTTAGCCGACAAAATAAAATTAAGAAAGTGTTAGCAATAGAAATTCCAAAATGCCGAGCAT
TTATGCATTTAGATACAGTATTTACAATGGTTGATTATGATAAGTTTACAATTCACCCAGCTAT
TCAAGGGCCAAAAGGGAATATGAATATTTATATTTTAGAAAAAGGAGCAGATGAGGAAACTCTT
AAAATTACACATCGTACTTCTTTAATGGAAGCATTAAAAGAGGTATTAGACTTAAGTGAATTAG
TTCTTATTCCATGTGGAGGAGGAGATGTAATTGCTTCTGCTCGTGAACAATGGAATGATGGCTC
GAACACATTAGCAATCGCGCCAGGTGTAGTTGTTACATATGATCGCAACTATGTATCCAATACG
TTATTACGGGAACACGGTATAGAAGTGATTGAGGTGCTAAGTTCAGAATTATCTCGTGGTCGTG
GGGGTCCACGTTGCATGAGTATGCCAATTGTTCGTAAAGATATTTAA-3'
```

FIG. 7

(C) The amino acid sequence of His-ABD-PolyN–bcADI:

(SEQ ID NO: 41)

MG<u>HHHHHH</u>DEAVDANSLAEAKVLANRELDKYGVSDYYKNLINNAKTVEGVKALIDEILAALP<u>SGSNNNNNNGSGG</u>KH
PIHVTSEIGELQTVLLKRPGKEVENLTPDYLQQLLFDDIPYLPIIQKEHDYFAQTLRNRGVEVLYLEKLAAEALVDKK
LREEFVDRILKEGQADVNVAHQTLKEYLLSFSNEELIQKIMGGVRKNEIETSKKTHLYELMEDHYPFYLDPMPNLYFT
RDPAASVGDGLTINKMREPARRRESLFMEYIIKYHPRFAKHNVPIWLDRDYKFPIEGGDELILNEETIAIGVSARTSA
KAIERLAKNLFSRQNKIKKVLAIEIPKCRAFMHLDTVFTMVDYDKFTIHPAIQGPKGNMNIYILEKGADEETLKITHR
TSLMEALKEVLDLSELVLIPCGGGDVIASAREQWNDGSNTLAIAPGVVVTYDRNYVSNTLLREHGIEVIEVLSSELSR
GRGGPRCMSMPIVRKDI (PolyN with linker: <u>SGSNNNNNNGSGG</u>)

FIG. 7 (continued)

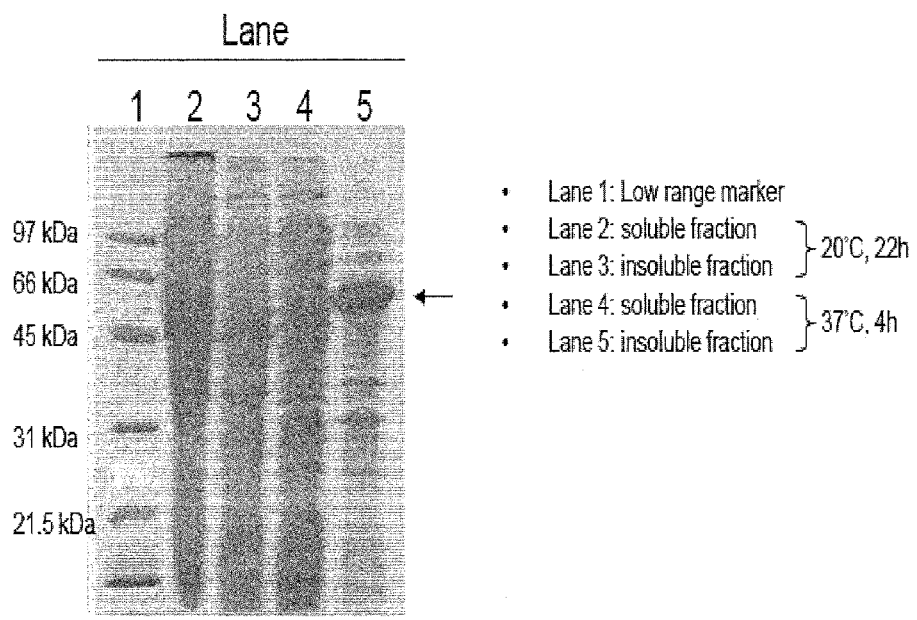
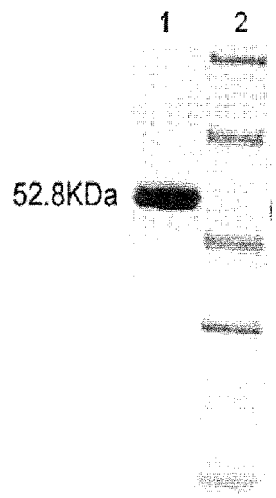
FIG. 8

Note:
HSA: Human serum albumin
AAD
AAD-HSA complex (A)
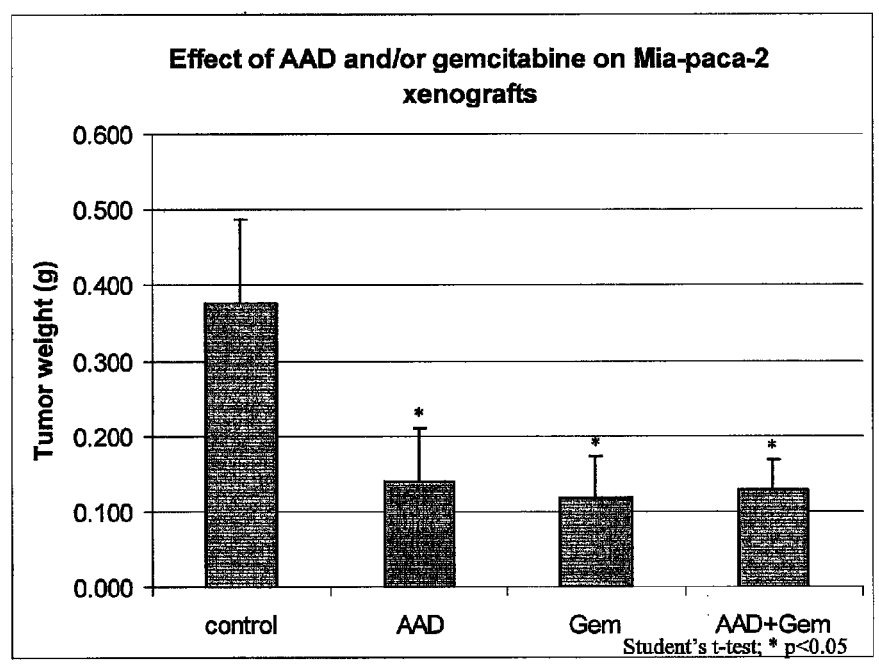
(B)
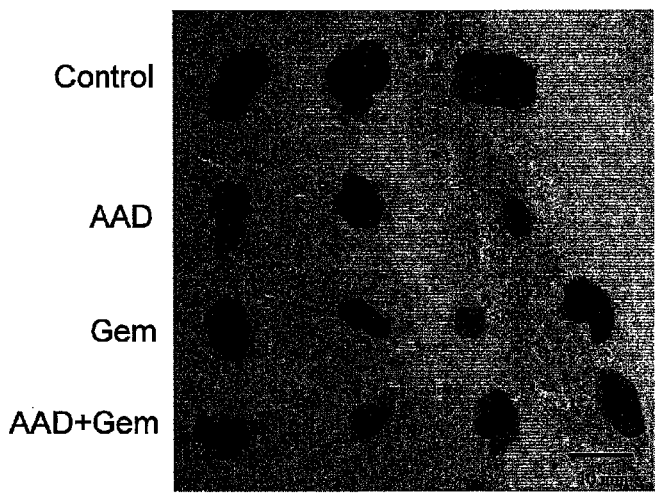
FIG. 12

(C)
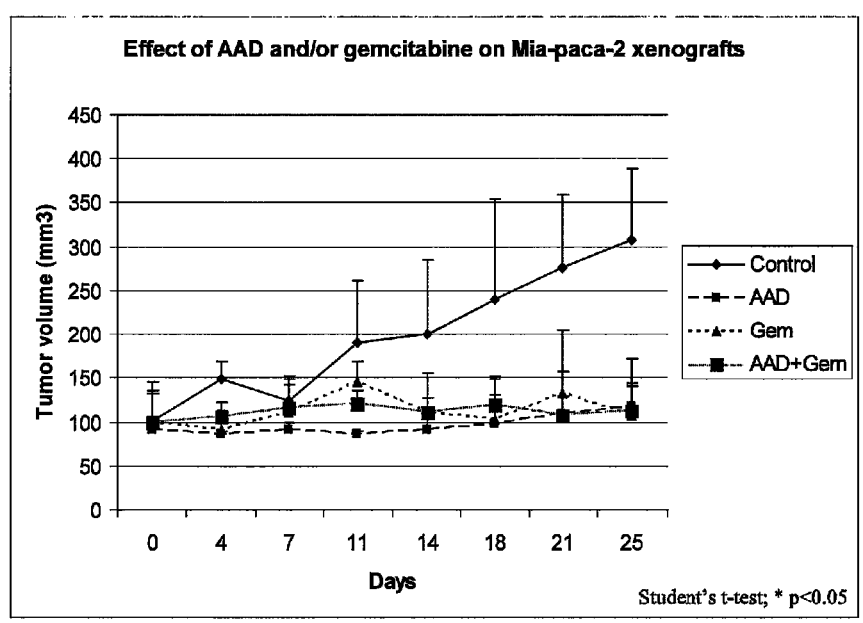
(D)
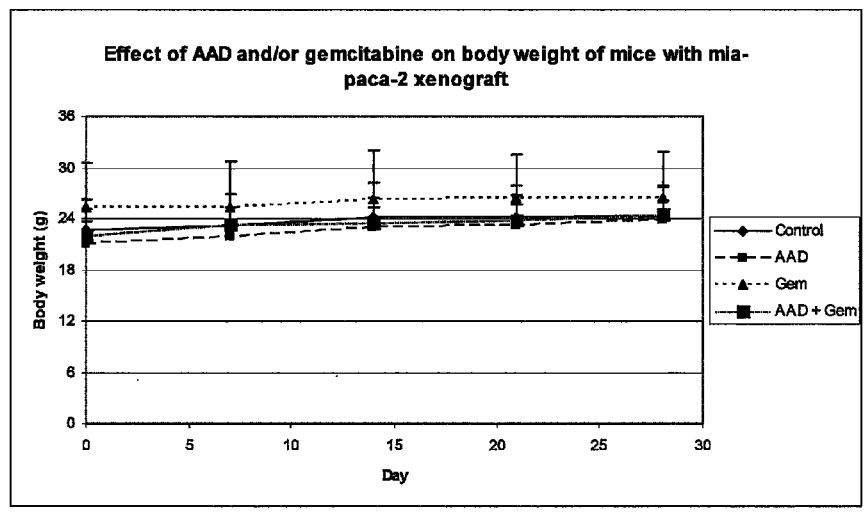
FIG. 12 (continued)

(A)
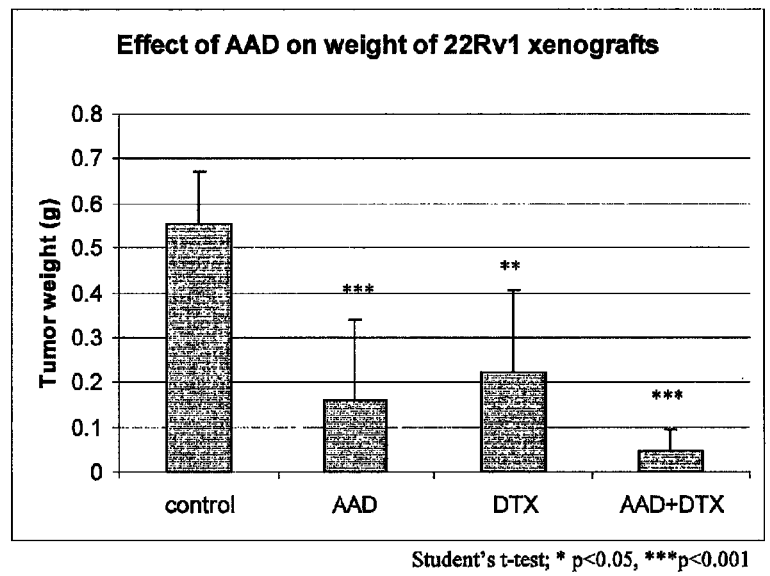
(B)
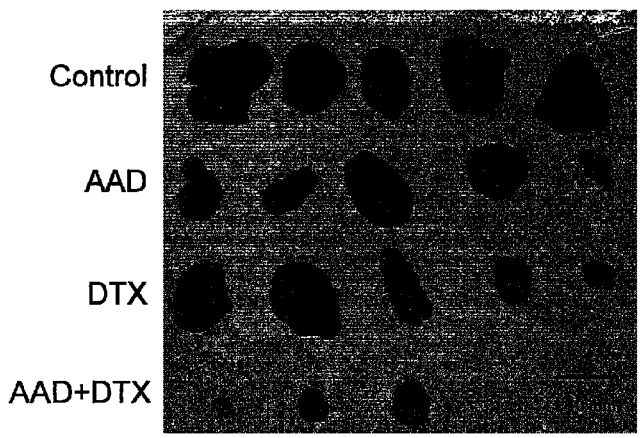
FIG. 13

(C)

```
                         SEQUENCE LISTING

<160> NUMBER OF SEQ ID NOS: 53

<210> SEQ ID NO 1
<211> LENGTH: 50
<212> TYPE: DNA
<213> ORGANISM: Artificial Sequence
<220> FEATURE:
<223> OTHER INFORMATION: the sequence is synthesized

<400> SEQUENCE: 1
catgatgcga attccttagc tgaagctaaa gtcttagcta acagagaact            50

<210> SEQ ID NO 2
<211> LENGTH: 50
<212> TYPE: DNA
<213> ORGANISM: Artificial Sequence
<220> FEATURE:
<223> OTHER INFORMATION: the sequence is synthesized

<400> SEQUENCE: 2
tagtcactta ctccatattt gtcaagttct ctgttagcta agactttagc            50

<210> SEQ ID NO 3
<211> LENGTH: 50
<212> TYPE: DNA
<213> ORGANISM: Artificial Sequence
<220> FEATURE:
<223> OTHER INFORMATION: the sequence is synthesized

<400> SEQUENCE: 3
gaacttgaca aatatggagt aagtgactat tacaagaacc taatcaacaa            50

<210> SEQ ID NO 4
<211> LENGTH: 50
<212> TYPE: DNA
<213> ORGANISM: Artificial Sequence
<220> FEATURE:
<223> OTHER INFORMATION: the sequence is synthesized
```

```
<400> SEQUENCE: 4
tacaccttca acagttttgg cattgttgat taggttcttg taatagtcac         50

<210> SEQ ID NO 5
<211> LENGTH: 50
<212> TYPE: DNA
<213> ORGANISM: Artificial Sequence
<220> FEATURE:
<223> OTHER INFORMATION: the sequence is synthesized

<400> SEQUENCE: 5
gccaaaactg ttgaaggtgt aaaagcactg atagatgaaa ttttagctgc         50

<210> SEQ ID NO 6
<211> LENGTH: 48
<212> TYPE: DNA
<213> ORGANISM: Artificial Sequence
<220> FEATURE:
<223> OTHER INFORMATION: the sequence is synthesized

<400> SEQUENCE: 6
agctacgata agcttaaggt aatgcagcta aaatttcatc tatcagtg           48

<210> SEQ ID NO 7
<211> LENGTH: 50
<212> TYPE: DNA
<213> ORGANISM: Artificial Sequence
<220> FEATURE:
<223> OTHER INFORMATION: the sequence is synthesized

<400> SEQUENCE: 7
catgatgcga attccttagc tgaagctaaa gtcttagcta acagagaact         50

<210> SEQ ID NO 8
<211> LENGTH: 48
<212> TYPE: DNA
<213> ORGANISM: Artificial Sequence
<220> FEATURE:
<223> OTHER INFORMATION: the sequence is synthesized

<400> SEQUENCE: 8
agctacgata agcttaaggt aatgcagcta aaatttcatc tatcagtg           48

<210> SEQ ID NO 9
<211> LENGTH: 37
<212> TYPE: DNA
<213> ORGANISM: Artificial Sequence
<220> FEATURE:
<223> OTHER INFORMATION: the sequence is synthesized

<400> SEQUENCE: 9
atcgatcgat gtctgtattt gacagtaaat ttaaagg                       37

<210> SEQ ID NO 10
<211> LENGTH: 51
<212> TYPE: DNA
<213> ORGANISM: Artificial Sequence
<220> FEATURE:
<223> OTHER INFORMATION: the sequence is synthesized

<400> SEQUENCE: 10
agctaaggaa ttcgcatcat gatggtgatg gtggtggcta ccccacttaa c       51
```

<210> SEQ ID NO 11
<211> LENGTH: 37
<212> TYPE: DNA
<213> ORGANISM: Artificial Sequence
<220> FEATURE:
<223> OTHER INFORMATION: the sequence is synthesized

<400> SEQUENCE: 11
atcgatcgat gtctgtattt gacagtaaat ttaaagg                         37

<210> SEQ ID NO 12
<211> LENGTH: 48
<212> TYPE: DNA
<213> ORGANISM: Artificial Sequence
<220> FEATURE:
<223> OTHER INFORMATION: the sequence is synthesized

<400> SEQUENCE: 12
agctacgata agcttaaggt aatgcagcta aaatttcatc tatcagtg             48

<210> SEQ ID NO 13
<211> LENGTH: 49
<212> TYPE: DNA
<213> ORGANISM: Artificial Sequence
<220> FEATURE:
<223> OTHER INFORMATION: the sequence is synthesized

<400> SEQUENCE: 13
ggagatatac atatgcatca tcaccatcac catgatgaag ccgtggatg            49

<210> SEQ ID NO 14
<211> LENGTH: 50
<212> TYPE: DNA
<213> ORGANISM: Artificial Sequence
<220> FEATURE:
<223> OTHER INFORMATION: the sequence is synthesized

<400> SEQUENCE: 14
ttgttattat tgttgttact acccgaaggt aatgcagcta aaatttcatc           50

<210> SEQ ID NO 15
<211> LENGTH: 42
<212> TYPE: DNA
<213> ORGANISM: Artificial Sequence
<220> FEATURE:
<223> OTHER INFORMATION: the sequence is synthesized

<400> SEQUENCE: 15
agaaccgccg ctaccattgt tattattgtt gttactaccc ga                   42

<210> SEQ ID NO 16
<211> LENGTH: 50
<212> TYPE: DNA
<213> ORGANISM: Artificial Sequence
<220> FEATURE:
<223> OTHER INFORMATION: the sequence is synthesized

<400> SEQUENCE: 16
aataataaca atggtagcgg cggttctgta tttgacagta aatttaaagg           50

<210> SEQ ID NO 17
<211> LENGTH: 44
<212> TYPE: DNA
<213> ORGANISM: Artificial Sequence
<220> FEATURE:
<223> OTHER INFORMATION: the sequence is synthesized

<400> SEQUENCE: 17
tagatcaatg gatccttacc acttaacatc tttacgtgat aaag                    44

<210> SEQ ID NO 18
<211> LENGTH: 49
<212> TYPE: DNA
<213> ORGANISM: Artificial Sequence
<220> FEATURE:
<223> OTHER INFORMATION: the sequence is synthesized

<400> SEQUENCE: 18
ggagatatac atatgcatca tcaccatcac catgatgaag ccgtggatg               49

<210> SEQ ID NO 19
<211> LENGTH: 50
<212> TYPE: DNA
<213> ORGANISM: Artificial Sequence
<220> FEATURE:
<223> OTHER INFORMATION: the sequence is synthesized

<400> SEQUENCE: 19
ttgttattat tgttgttact acccgaaggt aatgcagcta aaatttcatc              50

<210> SEQ ID NO 20
<211> LENGTH: 42
<212> TYPE: DNA
<213> ORGANISM: Artificial Sequence
<220> FEATURE:
<223> OTHER INFORMATION: the sequence is synthesized

<400> SEQUENCE: 20
tttaccgccg ctaccattgt tattattgtt gttactaccc ga                      42

<210> SEQ ID NO 21
<211> LENGTH: 50
<212> TYPE: DNA
<213> ORGANISM: Artificial Sequence
<220> FEATURE:
<223> OTHER INFORMATION: the sequence is synthesized

<400> SEQUENCE: 21
aataataaca atggtagcgg cggtaaacat ccgatacatg ttacttcaga              50

<210> SEQ ID NO 22
<211> LENGTH: 44
<212> TYPE: DNA
<213> ORGANISM: Artificial Sequence
<220> FEATURE:
<223> OTHER INFORMATION: the sequence is synthesized

<400> SEQUENCE: 22
tagatcaatg gatccctaaa tatctttacg aacaattggc atac                    44

<210> SEQ ID NO 23
<211> LENGTH: 410
<212> TYPE: PRT
<213> ORGANISM: Mycoplasma arginini

<400> SEQUENCE: 23

Met Ser Val Phe Asp Ser Lys Phe Lys Gly Ile His Val Tyr Ser Glu
1               5                   10                  15

Ile Gly Glu Leu Glu Ser Val Leu Val His Glu Pro Gly Arg Glu Ile
            20                  25                  30

```
Asp Tyr Ile Thr Pro Ala Arg Leu Asp Glu Leu Leu Phe Ser Ala Ile
             35                  40                  45

Leu Glu Ser His Asp Ala Arg Lys Glu His Lys Gln Phe Val Ala Glu
 50                  55                  60

Leu Lys Ala Asn Asp Ile Asn Val Val Glu Leu Ile Asp Leu Val Ala
 65                  70                  75                  80

Glu Thr Tyr Asp Leu Ala Ser Gln Glu Ala Lys Asp Lys Leu Ile Glu
                 85                  90                  95

Glu Phe Leu Glu Asp Ser Glu Pro Val Leu Ser Glu Glu His Lys Val
            100                 105                 110

Val Val Arg Asn Phe Leu Lys Ala Lys Lys Thr Ser Arg Glu Leu Val
            115                 120                 125

Glu Ile Met Met Ala Gly Ile Thr Lys Tyr Asp Leu Gly Ile Glu Ala
            130                 135                 140

Asp His Glu Leu Ile Val Asp Pro Met Pro Asn Leu Tyr Phe Thr Arg
145                 150                 155                 160

Asp Pro Phe Ala Ser Val Gly Asn Gly Val Thr Ile His Tyr Met Arg
                165                 170                 175

Tyr Lys Val Arg Gln Arg Glu Thr Leu Phe Ser Arg Phe Val Phe Ser
            180                 185                 190

Asn His Pro Lys Leu Ile Asn Thr Pro Trp Tyr Tyr Asp Pro Ser Leu
            195                 200                 205

Lys Leu Ser Ile Glu Gly Gly Asp Val Phe Ile Tyr Asn Asn Asp Thr
        210                 215                 220

Leu Val Val Gly Val Ser Glu Arg Thr Asp Leu Gln Thr Val Thr Leu
225                 230                 235                 240

Leu Ala Lys Asn Ile Val Asn Lys Glu Cys Glu Phe Lys Arg Ile
                245                 250                 255

Val Ala Ile Asn Val Pro Lys Trp Thr Asn Leu Met His Leu Asp Thr
            260                 265                 270

Trp Leu Thr Met Leu Asp Lys Asp Lys Phe Leu Tyr Ser Pro Ile Ala
        275                 280                 285

Asn Asp Val Phe Lys Phe Trp Asp Tyr Asp Leu Val Asn Gly Gly Ala
        290                 295                 300

Glu Pro Gln Pro Val Glu Asn Gly Leu Pro Leu Glu Gly Leu Leu Gln
305                 310                 315                 320

Ser Ile Ile Asn Lys Lys Pro Val Leu Ile Pro Ile Ala Gly Glu Gly
                325                 330                 335

Ala Ser Gln Met Glu Ile Glu Arg Glu Thr His Phe Asp Gly Thr Asn
            340                 345                 350

Tyr Leu Ala Ile Arg Pro Gly Val Val Ile Gly Tyr Ser Arg Asn Glu
            355                 360                 365

Lys Thr Asn Ala Ala Leu Glu Ala Ala Gly Ile Lys Val Leu Pro Phe
            370                 375                 380

His Gly Asn Gln Leu Ser Leu Gly Met Gly Asn Ala Arg Cys Met Ser
385                 390                 395                 400

Met Pro Leu Ser Arg Lys Asp Val Lys Trp
                405                 410

<210> SEQ ID NO 24
<211> LENGTH: 410
<212> TYPE: PRT
<213> ORGANISM: Lactococcus lactis
```

<400> SEQUENCE: 24

```
Met Asn Gly Ile Asn Val Asn Ser Glu Ile Gly Lys Leu Lys Ser
1               5                   10                  15

Val Leu Leu His Arg Pro Gly Ala Glu Val Glu Asn Ile Thr Pro Asp
            20                  25                  30

Thr Met Lys Gln Leu Leu Phe Asp Asp Ile Pro Tyr Leu Lys Ile Ala
        35                  40                  45

Gln Lys Glu His Asp Phe Phe Ala Gln Thr Leu Arg Asp Asn Gly Ala
    50                  55                  60

Glu Thr Val Tyr Ile Glu Asn Leu Ala Thr Glu Val Phe Glu Lys Ser
65                  70                  75                  80

Ser Glu Thr Lys Glu Glu Phe Leu Ser His Leu Leu His Glu Ala Gly
                85                  90                  95

Tyr Arg Pro Gly Arg Thr Tyr Asp Gly Leu Thr Glu Tyr Leu Thr Ser
            100                 105                 110

Met Pro Thr Lys Asp Met Val Glu Lys Val Tyr Ala Gly Val Arg Lys
        115                 120                 125

Asn Glu Leu Asp Ile Lys Arg Thr Ala Leu Ser Asp Met Ala Gly Ser
130                 135                 140

Asp Ala Glu Asn Tyr Phe Tyr Leu Asn Pro Leu Pro Asn Ala Tyr Phe
145                 150                 155                 160

Thr Arg Asp Pro Gln Ala Ser Met Gly Val Gly Met Thr Ile Asn Lys
                165                 170                 175

Met Thr Phe Pro Ala Arg Gln Pro Glu Ser Leu Ile Thr Glu Tyr Val
        180                 185                 190

Met Ala Asn His Pro Arg Phe Lys Asp Thr Pro Ile Trp Arg Asp Arg
    195                 200                 205

Asn His Thr Thr Arg Ile Glu Gly Gly Asp Glu Leu Ile Leu Asn Lys
210                 215                 220

Thr Thr Val Ala Ile Gly Val Ser Glu Arg Thr Ser Ser Lys Thr Ile
225                 230                 235                 240

Gln Asn Leu Ala Lys Glu Leu Phe Ala Asn Pro Leu Ser Thr Phe Asp
                245                 250                 255

Thr Val Leu Ala Val Glu Ile Pro His Asn His Ala Met Met His Leu
            260                 265                 270

Asp Thr Val Phe Thr Met Ile Asn His Asp Gln Phe Thr Val Phe Pro
        275                 280                 285

Gly Ile Met Asp Gly Ala Gly Asn Ile Asn Val Phe Ile Leu Arg Pro
    290                 295                 300

Gly Gln Asp Gly Glu Val Glu Ile Glu His Leu Thr Asp Leu Lys Ala
305                 310                 315                 320

Ala Leu Lys Lys Val Leu Asn Leu Ser Glu Leu Asp Leu Ile Glu Cys
                325                 330                 335

Gly Ala Gly Asp Pro Ile Ala Ala Pro Arg Glu Gln Trp Asn Asp Gly
            340                 345                 350

Ser Asn Thr Leu Ala Ile Ala Pro Gly Glu Ile Val Thr Tyr Asp Arg
        355                 360                 365

Asn Tyr Val Thr Val Glu Leu Leu Lys Glu His Gly Ile Lys Val His
    370                 375                 380

Glu Ile Leu Ser Ser Glu Leu Gly Arg Gly Arg Gly Ala Arg Cys
385                 390                 395                 400

Met Ser Gln Pro Leu Trp Arg Glu Asp Leu
                405                 410
```

-continued

<210> SEQ ID NO 25
<211> LENGTH: 410
<212> TYPE: PRT
<213> ORGANISM: Bacillus cereus

<400> SEQUENCE: 25

```
Met Lys His Pro Ile His Val Thr Ser Glu Ile Gly Glu Leu Gln Thr
1               5                   10                  15

Val Leu Leu Lys Arg Pro Gly Lys Glu Val Glu Asn Leu Thr Pro Asp
            20                  25                  30

Tyr Leu Gln Gln Leu Leu Phe Asp Asp Ile Pro Tyr Leu Pro Ile Ile
        35                  40                  45

Gln Lys Glu His Asp Tyr Phe Ala Gln Thr Leu Arg Asn Arg Gly Val
    50                  55                  60

Glu Val Leu Tyr Leu Glu Lys Leu Ala Ala Glu Ala Leu Val Asp Lys
65                  70                  75                  80

Lys Leu Arg Glu Glu Phe Val Asp Arg Ile Leu Lys Glu Gly Gln Ala
                85                  90                  95

Asp Val Asn Val Ala His Gln Thr Leu Lys Glu Tyr Leu Leu Ser Phe
            100                 105                 110

Ser Asn Glu Glu Leu Ile Gln Lys Ile Met Gly Gly Val Arg Lys Asn
        115                 120                 125

Glu Ile Glu Thr Ser Lys Lys Thr His Leu Tyr Glu Leu Met Glu Asp
    130                 135                 140

His Tyr Pro Phe Tyr Leu Asp Pro Met Pro Asn Leu Tyr Phe Thr Arg
145                 150                 155                 160

Asp Pro Ala Ala Ser Val Gly Asp Gly Leu Thr Ile Asn Lys Met Arg
                165                 170                 175

Glu Pro Ala Arg Arg Arg Glu Ser Leu Phe Met Glu Tyr Ile Ile Lys
            180                 185                 190

Tyr His Pro Arg Phe Ala Lys His Asn Val Pro Ile Trp Leu Asp Arg
        195                 200                 205

Asp Tyr Lys Phe Pro Ile Glu Gly Gly Asp Glu Leu Ile Leu Asn Glu
    210                 215                 220

Glu Thr Ile Ala Ile Gly Val Ser Ala Arg Thr Ser Ala Lys Ala Ile
225                 230                 235                 240

Glu Arg Leu Ala Lys Asn Leu Phe Ser Arg Gln Asn Lys Ile Lys Lys
                245                 250                 255

Val Leu Ala Ile Glu Ile Pro Lys Cys Arg Ala Phe Met His Leu Asp
            260                 265                 270

Thr Val Phe Thr Met Val Asp Tyr Asp Lys Phe Thr Ile His Pro Ala
        275                 280                 285

Ile Gln Gly Pro Lys Gly Asn Met Asn Ile Tyr Ile Leu Glu Lys Gly
    290                 295                 300

Ala Asp Glu Glu Thr Leu Lys Ile Thr His Arg Thr Ser Leu Met Glu
305                 310                 315                 320

Ala Leu Lys Glu Val Leu Asp Leu Ser Glu Leu Val Leu Ile Pro Cys
                325                 330                 335

Gly Gly Gly Asp Val Ile Ala Ser Ala Arg Glu Gln Trp Asn Asp Gly
            340                 345                 350

Ser Asn Thr Leu Ala Ile Ala Pro Gly Val Val Val Thr Tyr Asp Arg
        355                 360                 365

Asn Tyr Val Ser Asn Thr Leu Leu Arg Glu His Gly Ile Glu Val Ile
    370                 375                 380
```

Glu Val Leu Ser Ser Glu Leu Ser Arg Gly Arg Gly Gly Pro Arg Cys
385                 390                 395                 400

Met Ser Met Pro Ile Val Arg Lys Asp Ile
            405                 410

<210> SEQ ID NO 26
<211> LENGTH: 413
<212> TYPE: PRT
<213> ORGANISM: Bacillus licheniformis

<400> SEQUENCE: 26

Met Ile Met Thr Thr Pro Ile His Val Tyr Ser Glu Ile Gly Pro Leu
1               5                   10                  15

Lys Thr Val Met Leu Lys Arg Pro Gly Arg Glu Leu Glu Asn Leu Thr
            20                  25                  30

Pro Glu Tyr Leu Glu Arg Leu Leu Phe Asp Asp Ile Pro Phe Leu Pro
        35                  40                  45

Ala Val Gln Lys Glu His Asp Gln Phe Ala Glu Thr Leu Lys Gln Gln
    50                  55                  60

Gly Ala Glu Val Leu Tyr Leu Glu Lys Leu Thr Ala Glu Ala Leu Asp
65                  70                  75                  80

Asp Ala Leu Val Arg Glu Gln Phe Ile Asp Glu Leu Leu Thr Glu Ser
                85                  90                  95

Lys Ala Asp Ile Asn Gly Ala Tyr Asp Arg Leu Lys Glu Phe Leu Leu
            100                 105                 110

Thr Phe Asp Ala Asp Ser Met Val Glu Gln Val Met Ser Gly Ile Arg
        115                 120                 125

Lys Asn Glu Leu Glu Arg Glu Lys Lys Ser His Leu His Glu Leu Met
130                 135                 140

Glu Asp His Tyr Pro Phe Tyr Leu Asp Pro Met Pro Asn Leu Tyr Phe
145                 150                 155                 160

Thr Arg Asp Pro Ala Ala Ala Ile Gly Ser Gly Leu Thr Ile Asn Lys
                165                 170                 175

Met Lys Glu Pro Ala Arg Arg Glu Ser Leu Phe Met Arg Tyr Ile
            180                 185                 190

Ile Asn His His Pro Arg Phe Lys Gly His Glu Ile Pro Val Trp Leu
        195                 200                 205

Asp Arg Asp Phe Lys Phe Asn Ile Glu Gly Gly Asp Glu Leu Val Leu
210                 215                 220

Asn Glu Glu Thr Val Ala Ile Gly Val Ser Glu Arg Thr Thr Ala Gln
225                 230                 235                 240

Ala Ile Glu Arg Leu Val Arg Asn Leu Phe Gln Arg Gln Ser Arg Ile
                245                 250                 255

Arg Arg Val Leu Ala Val Glu Ile Pro Lys Ser Arg Ala Phe Met His
            260                 265                 270

Leu Asp Thr Val Phe Thr Met Val Asp Arg Asp Gln Phe Thr Ile His
        275                 280                 285

Pro Ala Ile Gln Gly Pro Glu Gly Asp Met Arg Ile Phe Val Leu Glu
    290                 295                 300

Arg Gly Lys Thr Ala Asp Glu Ile His Thr Thr Glu Glu His Asn Leu
305                 310                 315                 320

Pro Glu Val Leu Lys Arg Thr Leu Gly Leu Ser Asp Val Asn Leu Ile
                325                 330                 335

Phe Cys Gly Gly Gly Asp Glu Ile Ala Ser Ala Arg Glu Gln Trp Asn
            340                 345                 350

```
Asp Gly Ser Asn Thr Leu Ala Ile Ala Pro Gly Val Val Thr Tyr
            355                 360                 365

Asp Arg Asn Tyr Ile Ser Asn Glu Cys Leu Arg Glu Gln Gly Ile Lys
370                 375                 380

Val Ile Glu Ile Pro Ser Gly Glu Leu Ser Arg Gly Arg Gly Pro
385                 390                 395                 400

Arg Cys Met Ser Met Pro Leu Tyr Arg Glu Asp Val Lys
                405                 410

<210> SEQ ID NO 27
<211> LENGTH: 409
<212> TYPE: PRT
<213> ORGANISM: Mycoplasma arthritidis

<400> SEQUENCE: 27

Met Ser Val Phe Asp Ser Lys Phe Lys Gly Ile His Val Tyr Ser Glu
1               5                   10                  15

Ile Gly Glu Leu Glu Thr Val Leu Val His Glu Pro Gly Lys Glu Ile
            20                  25                  30

Asp Tyr Ile Thr Pro Ala Arg Leu Asp Glu Leu Leu Phe Ser Ala Ile
        35                  40                  45

Leu Glu Ser His Asp Ala Arg Lys Glu His Lys Glu Phe Val Ala Glu
    50                  55                  60

Leu Lys Lys Arg Gly Ile Asn Val Val Glu Leu Val Asp Leu Ile Val
65                  70                  75                  80

Glu Thr Tyr Asp Leu Ala Ser Lys Glu Ala Lys Glu Lys Leu Leu Glu
                85                  90                  95

Glu Phe Leu Asp Asp Ser Val Pro Val Leu Ser Asp Glu His Arg Ala
            100                 105                 110

Ala Val Lys Lys Phe Leu Gln Ser Gln Lys Ser Thr Arg Ser Leu Val
        115                 120                 125

Glu Tyr Met Ile Ala Gly Ile Thr Lys His Asp Leu Lys Ile Glu Ser
    130                 135                 140

Asp Leu Glu Leu Ile Val Asp Pro Met Pro Asn Leu Tyr Phe Thr Arg
145                 150                 155                 160

Asp Pro Phe Ala Ser Val Gly Asn Gly Val Thr Ile His Tyr Met Arg
                165                 170                 175

Tyr Lys Val Arg Gln Arg Glu Thr Leu Phe Ser Arg Phe Val Phe Ser
            180                 185                 190

Asn His Pro Lys Leu Val Asn Thr Pro Trp Tyr Tyr Asp Pro Ala Glu
        195                 200                 205

Gly Leu Ser Ile Glu Gly Gly Asp Val Phe Ile Tyr Asn Asn Asp Thr
    210                 215                 220

Leu Val Val Gly Val Ser Glu Arg Thr Asp Leu Gln Thr Ile Thr Leu
225                 230                 235                 240

Leu Ala Lys Asn Ile Lys Ala Asn Lys Glu Cys Glu Phe Lys Arg Ile
                245                 250                 255

Val Ala Ile Asn Val Pro Lys Trp Thr Asn Leu Met His Leu Asp Thr
            260                 265                 270

Trp Leu Thr Met Leu Asp Lys Asp Lys Phe Leu Tyr Ser Pro Ile Ala
        275                 280                 285

Asn Asp Val Phe Lys Phe Trp Asp Tyr Asp Leu Val Asn Gly Gly Asp
    290                 295                 300

Ala Pro Gln Pro Val Asp Asn Gly Leu Pro Leu Glu Asp Leu Leu Lys
305                 310                 315                 320
```

```
Ser Ile Ile Gly Lys Lys Pro Thr Leu Ile Pro Ile Ala Gly Ala Gly
            325                 330                 335

Ala Ser Gln Ile Asp Ile Glu Arg Glu Thr His Phe Asp Gly Thr Asn
            340                 345                 350

Tyr Leu Ala Val Ala Pro Gly Ile Val Ile Gly Tyr Ala Arg Asn Glu
            355                 360                 365

Lys Thr Asn Ala Ala Leu Glu Ala Ala Gly Ile Thr Val Leu Pro Phe
370                 375                 380

Arg Gly Asn Gln Leu Ser Leu Gly Met Gly Asn Ala Arg Cys Met Ser
385                 390                 395                 400

Met Pro Leu Ser Arg Lys Asp Val Lys
            405
```

<210> SEQ ID NO 28
<211> LENGTH: 409
<212> TYPE: PRT
<213> ORGANISM: Mycoplasma hominis

<400> SEQUENCE: 28

```
Met Ser Val Phe Asp Ser Lys Phe Asn Gly Ile His Val Tyr Ser Glu
1               5                   10                  15

Ile Gly Glu Leu Glu Thr Val Leu Val His Glu Pro Gly Arg Glu Ile
            20                  25                  30

Asp Tyr Ile Thr Pro Ala Arg Leu Asp Glu Leu Leu Phe Ser Ala Ile
            35                  40                  45

Leu Glu Ser His Asp Ala Arg Lys Glu His Gln Ser Phe Val Lys Ile
        50                  55                  60

Met Lys Asp Arg Gly Ile Asn Val Val Glu Leu Thr Asp Leu Val Ala
65                  70                  75                  80

Glu Thr Tyr Asp Leu Ala Ser Lys Ala Ala Lys Glu Glu Phe Ile Glu
            85                  90                  95

Thr Phe Leu Glu Glu Thr Val Pro Val Leu Thr Glu Ala Asn Lys Lys
            100                 105                 110

Ala Val Arg Ala Phe Leu Leu Ser Lys Pro Thr His Glu Met Val Glu
            115                 120                 125

Phe Met Met Ser Gly Ile Thr Lys Tyr Glu Leu Gly Val Glu Ser Glu
            130                 135                 140

Asn Glu Leu Ile Val Asp Pro Met Pro Asn Leu Tyr Phe Thr Arg Asp
145                 150                 155                 160

Pro Phe Ala Ser Val Gly Asn Gly Val Thr Ile His Phe Met Arg Tyr
            165                 170                 175

Ile Val Arg Arg Arg Glu Thr Leu Phe Ala Arg Phe Val Phe Arg Asn
            180                 185                 190

His Pro Lys Leu Val Lys Thr Pro Trp Tyr Tyr Asp Pro Ala Met Lys
            195                 200                 205

Met Ser Ile Glu Gly Gly Asp Val Phe Ile Tyr Asn Asn Glu Thr Leu
            210                 215                 220

Val Val Gly Val Ser Glu Arg Thr Asp Leu Asp Thr Ile Thr Leu Leu
225                 230                 235                 240

Ala Lys Asn Ile Lys Ala Asn Lys Glu Val Glu Phe Lys Arg Ile Val
            245                 250                 255

Ala Ile Asn Val Pro Lys Trp Thr Asn Leu Met His Leu Asp Thr Trp
            260                 265                 270

Leu Thr Met Leu Asp Lys Asn Lys Phe Leu Tyr Ser Pro Ile Ala Asn
            275                 280                 285
```

```
Asp Val Phe Lys Phe Trp Asp Tyr Asp Leu Val Asn Gly Gly Ala Glu
290                 295                 300
Pro Gln Pro Gln Leu Asn Gly Leu Pro Leu Asp Lys Leu Leu Ala Ser
305                 310                 315                 320
Ile Ile Asn Lys Glu Pro Val Leu Ile Pro Ile Gly Gly Ala Gly Ala
                325                 330                 335
Thr Glu Met Glu Ile Ala Arg Glu Thr Asn Phe Asp Gly Thr Asn Tyr
            340                 345                 350
Leu Ala Ile Lys Pro Gly Leu Val Ile Gly Tyr Asp Arg Asn Glu Lys
        355                 360                 365
Thr Asn Ala Ala Leu Lys Ala Ala Gly Ile Thr Val Leu Pro Phe His
370                 375                 380
Gly Asn Gln Leu Ser Leu Gly Met Gly Asn Ala Arg Cys Met Ser Met
385                 390                 395                 400
Pro Leu Ser Arg Lys Asp Val Lys Trp
                405
```

<210> SEQ ID NO 29
<211> LENGTH: 411
<212> TYPE: PRT
<213> ORGANISM: Streptococcus pyogenes

<400> SEQUENCE: 29

```
Met Thr Ala Gln Thr Pro Ile His Val Tyr Ser Glu Ile Gly Lys Leu
1               5                   10                  15
Lys Lys Val Leu Leu His Arg Pro Gly Lys Glu Ile Glu Asn Leu Met
            20                  25                  30
Pro Asp Tyr Leu Glu Arg Leu Leu Phe Asp Asp Ile Pro Phe Leu Glu
        35                  40                  45
Asp Ala Gln Lys Glu His Asp Ala Phe Ala Gln Ala Leu Arg Asp Glu
    50                  55                  60
Gly Ile Glu Val Leu Tyr Leu Glu Thr Leu Ala Ala Glu Ser Leu Val
65                  70                  75                  80
Thr Pro Glu Ile Arg Glu Ala Phe Ile Asp Glu Tyr Leu Ser Glu Ala
                85                  90                  95
Asn Ile Arg Gly Arg Ala Thr Lys Lys Ala Ile Arg Glu Leu Leu Met
            100                 105                 110
Ala Ile Glu Asp Asn Gln Glu Leu Ile Glu Lys Thr Met Ala Gly Val
        115                 120                 125
Gln Lys Ser Glu Leu Pro Glu Ile Pro Ala Ser Glu Lys Gly Leu Thr
    130                 135                 140
Asp Leu Val Glu Ser Ser Tyr Pro Phe Ala Ile Asp Pro Met Pro Asn
145                 150                 155                 160
Leu Tyr Phe Thr Arg Asp Pro Phe Ala Thr Ile Gly Thr Gly Val Ser
                165                 170                 175
Leu Asn His Met Phe Ser Glu Thr Arg Asn Arg Glu Thr Leu Tyr Gly
            180                 185                 190
Lys Tyr Ile Phe Thr His His Pro Ile Tyr Gly Gly Gly Lys Val Pro
        195                 200                 205
Met Val Tyr Asp Arg Asn Glu Thr Thr Arg Ile Glu Gly Gly Asp Glu
    210                 215                 220
Leu Val Leu Ser Lys Asp Val Leu Ala Val Gly Ile Ser Gln Arg Thr
225                 230                 235                 240
Asp Ala Ala Ser Ile Glu Lys Leu Leu Val Asn Ile Phe Lys Gln Asn
                245                 250                 255
```

```
Leu Gly Phe Lys Lys Val Leu Ala Phe Glu Phe Ala Asn Asn Arg Lys
                260                 265                 270

Phe Met His Leu Asp Thr Val Phe Thr Met Val Asp Tyr Asp Lys Phe
            275                 280                 285

Thr Ile His Pro Glu Ile Glu Gly Asp Leu Arg Val Tyr Ser Val Thr
        290                 295                 300

Tyr Asp Asn Glu Glu Leu His Ile Val Glu Glu Lys Gly Asp Leu Ala
305                 310                 315                 320

Asp Leu Leu Ala Ala Asn Leu Gly Val Glu Lys Val Asp Leu Ile Arg
                325                 330                 335

Cys Gly Gly Asp Asn Leu Val Ala Ala Gly Arg Glu Gln Trp Asn Asp
            340                 345                 350

Gly Ser Asn Thr Leu Thr Ile Ala Pro Gly Val Val Val Tyr Asn
        355                 360                 365

Arg Asn Thr Ile Thr Asn Ala Ile Leu Glu Ser Lys Gly Leu Lys Leu
        370                 375                 380

Ile Lys Ile His Gly Ser Glu Leu Val Arg Gly Arg Gly Gly Pro Arg
385                 390                 395                 400

Cys Met Ser Met Pro Phe Glu Arg Glu Asp Ile
                405                 410

<210> SEQ ID NO 30
<211> LENGTH: 409
<212> TYPE: PRT
<213> ORGANISM: Streptococcus pneumonia

<400> SEQUENCE: 30

Met Ser Ser His Pro Ile Gln Val Phe Ser Glu Ile Gly Lys Leu Lys
1               5                   10                  15

Lys Val Met Leu His Arg Pro Gly Lys Glu Leu Glu Asn Leu Leu Pro
            20                  25                  30

Asp Tyr Leu Glu Arg Leu Leu Phe Asp Asp Ile Pro Phe Leu Glu Asp
        35                  40                  45

Ala Gln Lys Glu His Asp Ala Phe Ala Gln Ala Leu Arg Asp Glu Gly
    50                  55                  60

Ile Glu Val Leu Tyr Leu Gln Leu Ala Ala Glu Ser Leu Thr Ser
65              70                  75                  80

Pro Glu Ile Arg Asp Gln Phe Ile Glu Glu Tyr Leu Asp Glu Ala Asn
                85                  90                  95

Ile Arg Asp Arg Gln Thr Lys Val Ala Ile Arg Glu Leu Leu His Gly
            100                 105                 110

Ile Lys Asp Asn Gln Glu Leu Val Glu Lys Thr Met Ala Gly Ile Gln
        115                 120                 125

Lys Val Glu Leu Pro Glu Ile Pro Asp Glu Ala Lys Asp Leu Thr Asp
    130                 135                 140

Leu Val Glu Ser Asp Tyr Pro Phe Ala Ile Asp Pro Met Pro Asn Leu
145                 150                 155                 160

Tyr Phe Thr Arg Asp Pro Phe Ala Thr Ile Gly Asn Ala Val Ser Leu
                165                 170                 175

Asn His Met Phe Ala Asp Thr Arg Asn Arg Glu Thr Leu Tyr Gly Lys
            180                 185                 190

Tyr Ile Phe Lys Tyr His Pro Ile Tyr Gly Gly Lys Val Asp Leu Val
        195                 200                 205

Tyr Asn Arg Glu Glu Asp Thr Arg Ile Glu Gly Gly Asp Glu Leu Val
    210                 215                 220
```

-continued

```
Leu Ser Lys Asp Val Leu Ala Val Gly Ile Ser Gln Arg Thr Asp Ala
225                 230                 235                 240

Ala Ser Ile Glu Lys Leu Leu Val Asn Ile Phe Lys Lys Asn Val Gly
            245                 250                 255

Phe Lys Lys Val Leu Ala Phe Glu Phe Ala Asn Asn Arg Lys Phe Met
                260                 265                 270

His Leu Asp Thr Val Phe Thr Met Val Asp Tyr Asp Lys Phe Thr Ile
            275                 280                 285

His Pro Glu Ile Glu Gly Asp Leu His Val Tyr Ser Val Thr Tyr Glu
        290                 295                 300

Asn Glu Lys Leu Lys Ile Val Glu Glu Lys Gly Asp Leu Ala Glu Leu
305                 310                 315                 320

Leu Ala Gln Asn Leu Gly Val Glu Lys Val His Leu Ile Arg Cys Gly
                325                 330                 335

Gly Gly Asn Ile Val Ala Ala Ala Arg Glu Gln Trp Asn Asp Gly Ser
            340                 345                 350

Asn Thr Leu Thr Ile Ala Pro Gly Val Val Val Tyr Asp Arg Asn
                355                 360                 365

Thr Val Thr Asn Lys Ile Leu Glu Glu Tyr Gly Leu Arg Leu Ile Lys
    370                 375                 380

Ile Arg Gly Ser Glu Leu Val Arg Gly Arg Gly Pro Arg Cys Met
385                 390                 395                 400

Ser Met Pro Phe Glu Arg Glu Val
                405

<210> SEQ ID NO 31
<211> LENGTH: 402
<212> TYPE: PRT
<213> ORGANISM: Mycobacterium tuberculosis

<400> SEQUENCE: 31

Met Gly Val Glu Leu Gly Ser Asn Ser Glu Val Gly Ala Leu Arg Val
1               5                   10                  15

Val Ile Leu His Arg Pro Gly Ala Glu Leu Arg Arg Leu Thr Pro Arg
            20                  25                  30

Asn Thr Asp Gln Leu Leu Phe Asp Gly Leu Pro Trp Val Ser Arg Ala
        35                  40                  45

Gln Asp Glu His Asp Glu Phe Ala Glu Leu Leu Ala Ser Arg Gly Ala
    50                  55                  60

Glu Val Leu Leu Leu Ser Asp Leu Leu Thr Glu Ala Leu His His Ser
65                  70                  75                  80

Gly Ala Ala Arg Met Gln Gly Ile Ala Ala Ala Val Asp Ala Pro Arg
                85                  90                  95

Leu Gly Leu Pro Leu Ala Gln Glu Leu Ser Ala Tyr Leu Arg Ser Leu
            100                 105                 110

Asp Pro Gly Arg Leu Ala His Val Leu Thr Ala Gly Met Thr Phe Asn
        115                 120                 125

Glu Leu Pro Ser Asp Thr Arg Thr Asp Val Ser Leu Val Leu Arg Met
    130                 135                 140

His His Gly Gly Asp Phe Val Ile Glu Pro Leu Pro Asn Leu Val Phe
145                 150                 155                 160

Thr Arg Asp Ser Ser Ile Trp Ile Gly Pro Arg Val Val Ile Pro Ser
                165                 170                 175

Leu Ala Leu Arg Ala Arg Val Arg Glu Ala Ser Leu Thr Asp Leu Ile
            180                 185                 190
```

Tyr Ala His His Pro Arg Phe Thr Gly Val Arg Ala Tyr Glu Ser
            195                 200                 205

Arg Thr Ala Pro Val Glu Gly Gly Asp Val Leu Leu Ala Pro Gly
210                 215                 220

Val Val Ala Val Gly Val Gly Glu Arg Thr Thr Pro Ala Gly Ala Glu
225                 230                 235                 240

Ala Leu Ala Arg Ser Leu Phe Asp Asp Leu Ala His Thr Val Leu
            245                 250                 255

Ala Val Pro Ile Ala Gln Gln Arg Ala Gln Met His Leu Asp Thr Val
            260                 265                 270

Cys Thr Met Val Asp Thr Asp Thr Met Val Met Tyr Ala Asn Val Val
        275                 280                 285

Asp Thr Leu Glu Ala Phe Thr Ile Gln Arg Thr Pro Asp Gly Val Thr
290                 295                 300

Ile Gly Asp Ala Ala Pro Phe Ala Glu Ala Ala Lys Ala Met Gly
305                 310                 315                 320

Ile Asp Lys Leu Arg Val Ile His Thr Gly Met Asp Pro Val Val Ala
            325                 330                 335

Glu Arg Glu Gln Trp Asp Asp Gly Asn Asn Thr Leu Ala Leu Ala Pro
        340                 345                 350

Gly Val Val Ala Tyr Glu Arg Asn Val Gln Thr Asn Ala Arg Leu
            355                 360                 365

Gln Asp Ala Gly Ile Glu Val Leu Thr Ile Ala Gly Ser Glu Leu Gly
        370                 375                 380

Thr Gly Arg Gly Gly Pro Arg Cys Met Ser Cys Pro Ala Ala Arg Asp
385                 390                 395                 400

Pro Leu

<210> SEQ ID NO 32
<211> LENGTH: 417
<212> TYPE: PRT
<213> ORGANISM: Pseudomonas plecoglossicida

<400> SEQUENCE: 32

Met Ser Thr Glu Lys Gln Lys Tyr Gly Val His Ser Glu Ala Gly Lys
1               5                   10                  15

Leu Arg Lys Val Met Val Cys Ser Pro Gly Leu Ala His Lys Arg Leu
            20                  25                  30

Thr Pro Ser Asn Cys Asp Glu Leu Leu Phe Asp Asp Val Ile Trp Val
        35                  40                  45

Asp Gln Ala Lys Arg Asp His Phe Asp Phe Val Thr Lys Met Arg Glu
50                  55                  60

Arg Gly Val Asp Val Leu Glu Met His Asn Leu Leu Thr Asp Ile Val
65                  70                  75                  80

Gln Asp Lys Asn Ala Leu Lys Trp Ile Leu Asp Arg Lys Leu Thr Asp
            85                  90                  95

Asp Thr Val Gly Val Gly Leu Lys Asn Glu Val Arg Ser Trp Leu Glu
        100                 105                 110

Gly Gln Asp Pro Arg His Leu Ala Glu Phe Leu Ile Gly Gly Val Ala
    115                 120                 125

Gly Gln Asp Leu Pro Gln Ser Glu Gly Ala Asp Val Val Lys Met Tyr
130                 135                 140

Asn Asp Tyr Leu Gly His Ser Ser Phe Ile Leu Pro Pro Leu Pro Asn
145                 150                 155                 160

```
Thr Gln Phe Thr Arg Asp Thr Thr Cys Trp Ile Tyr Gly Gly Val Thr
                165                 170                 175

Leu Asn Pro Met Tyr Trp Pro Ala Arg Arg Gln Glu Thr Leu Leu Thr
            180                 185                 190

Thr Ala Ile Tyr Lys Phe His Lys Glu Phe Thr Asn Ala Glu Phe Glu
        195                 200                 205

Val Trp Tyr Gly Asp Pro Asp Lys Glu His Gly Ser Ser Thr Leu Glu
    210                 215                 220

Gly Gly Asp Val Met Pro Ile Gly Lys Gly Ile Val Leu Ile Gly Met
225                 230                 235                 240

Gly Glu Arg Thr Ser Arg Gln Ala Ile Gly Gln Leu Ala Arg Asn Leu
                245                 250                 255

Phe Glu Lys Gly Ala Ala Thr Glu Val Ile Val Ala Gly Leu Pro Lys
            260                 265                 270

Ser Arg Ala Ala Met His Leu Asp Thr Val Phe Ser Phe Cys Asp Arg
        275                 280                 285

Asp Leu Val Thr Val Phe Pro Glu Val Val Asn Glu Ile Val Pro Phe
    290                 295                 300

Ile Ile Arg Pro Asp Glu Lys Lys Pro Tyr Gly Met Asp Val Arg Arg
305                 310                 315                 320

Ile Asn Lys Ser Phe Ile Glu Val Val Gly Glu Gln Leu Gly Val Lys
                325                 330                 335

Leu Arg Val Val Glu Thr Gly Gly Asn Ser Phe Ala Ala Glu Arg Glu
            340                 345                 350

Gln Trp Asp Asp Gly Asn Asn Val Val Ala Ile Glu Pro Gly Val Val
        355                 360                 365

Ile Gly Tyr Asp Arg Asn Thr Tyr Thr Asn Thr Leu Leu Arg Lys Ala
    370                 375                 380

Gly Ile Glu Val Ile Thr Ile Ser Ala Gly Glu Leu Gly Arg Gly Arg
385                 390                 395                 400

Gly Gly Gly His Cys Met Thr Cys Pro Ile Val Arg Asp Pro Ile Asp
                405                 410                 415

Tyr

<210> SEQ ID NO 33
<211> LENGTH: 420
<212> TYPE: PRT
<213> ORGANISM: Pseudomonas putida

<400> SEQUENCE: 33

Met Ser Ala Glu Lys Gln Lys Tyr Gly Val His Ser Glu Ala Gly Lys
1               5                   10                  15

Leu Arg Lys Val Met Val Cys Ser Pro Gly Leu Ala His Lys Arg Leu
            20                  25                  30

Thr Pro Ser Asn Cys Asp Glu Leu Leu Phe Asp Asp Val Ile Trp Val
        35                  40                  45

Asp Gln Ala Lys Arg Asp His Phe Asp Phe Val Thr Lys Met Arg Glu
    50                  55                  60

Arg Gly Val Asp Val Leu Glu Met His Asn Leu Leu Thr Asp Ile Val
65                  70                  75                  80

Gln Gln Pro Glu Ala Leu Lys Trp Ile Leu Asp Arg Lys Ile Thr Ser
                85                  90                  95

Asp Thr Val Gly Val Gly Leu Thr Asn Glu Val Arg Ser Trp Leu Glu
            100                 105                 110
```

```
Gly Leu Glu Pro Arg His Leu Ala Glu Phe Leu Ile Gly Gly Val Ala
            115                 120                 125

Gly Gln Asp Leu Pro Val Ser Glu Gly Ala Glu Val Ile Lys Met Tyr
        130                 135                 140

Asn Lys Tyr Leu Gly His Ser Ser Phe Ile Leu Pro Leu Pro Leu Asn
145                 150                 155                 160

Thr Gln Phe Thr Arg Asp Thr Thr Cys Trp Ile Tyr Gly Gly Val Thr
                165                 170                 175

Leu Asn Pro Met Tyr Trp Pro Ala Arg Arg Gln Glu Thr Leu Leu Thr
            180                 185                 190

Thr Ala Ile Tyr Lys Phe His Lys Glu Phe Thr Gly Ala Asp Phe Gln
        195                 200                 205

Val Trp Tyr Gly Asp Pro Asp Lys Asp His Gly Asn Ala Thr Leu Glu
    210                 215                 220

Gly Gly Asp Val Met Pro Val Gly Lys Gly Ile Val Leu Ile Gly Met
225                 230                 235                 240

Gly Glu Arg Thr Ser Arg His Ala Ile Gly Gln Leu Ala Gln Asn Leu
                245                 250                 255

Phe Glu Lys Gly Ala Ala Glu Lys Ile Ile Val Ala Gly Leu Pro Lys
            260                 265                 270

Ser Arg Ala Ala Met His Leu Asp Thr Val Phe Ser Phe Cys Asp Arg
        275                 280                 285

Asp Leu Val Thr Val Phe Pro Glu Val Val Lys Glu Ile Lys Pro Phe
    290                 295                 300

Ile Ile Thr Pro Asp Ser Ser Lys Pro Tyr Gly Met Asn Ile Ala Pro
305                 310                 315                 320

Gln Asp Ala Ser Phe Leu Glu Val Val Ser Glu Gln Leu Leu Gly Lys
                325                 330                 335

Lys Asp Lys Leu Arg Val Val Glu Thr Gly Gly Asn Ser Phe Ala Ala
            340                 345                 350

Glu Arg Glu Gln Trp Asp Gly Asn Asn Val Ala Leu Glu Pro
        355                 360                 365

Gly Val Val Ile Gly Tyr Asp Arg Asn Thr Tyr Thr Asn Thr Leu Leu
    370                 375                 380

Arg Lys Ala Gly Ile Glu Val Ile Thr Ile Ser Ala Gly Glu Leu Gly
385                 390                 395                 400

Arg Gly Arg Gly Gly His Cys Met Thr Cys Pro Ile Val Arg Asp
                405                 410                 415

Pro Ile Asp Tyr
            420

<210> SEQ ID NO 34
<211> LENGTH: 418
<212> TYPE: PRT
<213> ORGANISM: Pseudomonas aeruginosa

<400> SEQUENCE: 34

Met Ser Thr Glu Lys Thr Lys Leu Gly Val His Ser Glu Ala Gly Lys
1               5                   10                  15

Leu Arg Lys Val Met Val Cys Ser Pro Gly Leu Ala His Gln Arg Leu
            20                  25                  30

Thr Pro Ser Asn Cys Asp Glu Leu Leu Phe Asp Asp Val Ile Trp Val
        35                  40                  45

Asn Gln Ala Lys Arg Asp His Phe Asp Phe Val Thr Lys Met Arg Glu
    50                  55                  60
```

```
Arg Gly Ile Asp Val Leu Glu Met His Asn Leu Leu Thr Glu Thr Ile
 65                  70                  75                  80

Gln Asn Pro Glu Ala Leu Lys Trp Ile Leu Asp Arg Lys Ile Thr Ala
                 85                  90                  95

Asp Ser Val Gly Leu Gly Leu Thr Ser Glu Leu Arg Ser Trp Leu Glu
            100                 105                 110

Ser Leu Glu Pro Arg Lys Leu Ala Glu Tyr Leu Ile Gly Gly Val Ala
        115                 120                 125

Ala Asp Asp Leu Pro Ala Ser Glu Gly Ala Asn Ile Leu Lys Met Tyr
    130                 135                 140

Arg Glu Tyr Leu Gly His Ser Ser Phe Leu Leu Pro Pro Leu Pro Asn
145                 150                 155                 160

Thr Gln Phe Thr Arg Asp Thr Thr Cys Trp Ile Tyr Gly Gly Val Thr
                165                 170                 175

Leu Asn Pro Met Tyr Trp Pro Ala Arg Arg Gln Glu Thr Leu Leu Thr
            180                 185                 190

Thr Ala Ile Tyr Lys Phe His Pro Glu Phe Ala Asn Ala Glu Phe Glu
        195                 200                 205

Ile Trp Tyr Gly Asp Pro Asp Lys Asp His Gly Ser Ser Thr Leu Glu
    210                 215                 220

Gly Gly Asp Val Met Pro Ile Gly Asn Gly Val Val Leu Ile Gly Met
225                 230                 235                 240

Gly Glu Arg Ser Ser Arg Gln Ala Ile Gly Gln Val Ala Gln Ser Leu
                245                 250                 255

Phe Ala Lys Gly Ala Ala Glu Arg Val Ile Val Ala Gly Leu Pro Lys
            260                 265                 270

Ser Arg Ala Ala Met His Leu Asp Thr Val Phe Ser Phe Cys Asp Arg
        275                 280                 285

Asp Leu Val Thr Val Phe Pro Glu Val Val Lys Glu Ile Val Pro Phe
    290                 295                 300

Ser Leu Arg Pro Asp Pro Ser Ser Pro Tyr Gly Met Asn Ile Arg Arg
305                 310                 315                 320

Glu Glu Lys Thr Phe Leu Glu Val Val Ala Glu Ser Leu Gly Leu Lys
                325                 330                 335

Lys Leu Arg Val Val Glu Thr Gly Gly Asn Ser Phe Ala Ala Glu Arg
            340                 345                 350

Glu Gln Trp Asp Asp Gly Asn Asn Val Val Cys Leu Glu Pro Gly Val
        355                 360                 365

Val Val Gly Tyr Asp Arg Asn Thr Tyr Thr Asn Thr Leu Leu Arg Lys
    370                 375                 380

Ala Gly Val Glu Val Ile Thr Ile Ser Ala Ser Glu Leu Gly Arg Gly
385                 390                 395                 400

Arg Gly Gly Gly His Cys Met Thr Cys Pro Ile Val Arg Asp Pro Ile
                405                 410                 415

Asp Tyr
```

<210> SEQ ID NO 35
<211> LENGTH: 409
<212> TYPE: PRT
<213> ORGANISM: Streptococcus pneumoniae

```
<400> SEQUENCE: 35

Met Ser Ser His Pro Ile Gln Val Phe Ser Glu Ile Gly Lys Leu Lys
1               5                   10                  15

Lys Val Met Leu His Arg Pro Gly Lys Glu Leu Glu Asn Leu Leu Pro
            20                  25                  30

Asp Tyr Leu Glu Arg Leu Leu Phe Asp Asp Ile Pro Phe Leu Glu Asp
        35                  40                  45

Ala Gln Lys Glu His Asp Ala Phe Ala Gln Ala Leu Arg Asp Glu Gly
    50                  55                  60

Ile Glu Val Leu Tyr Leu Glu Gln Leu Ala Ala Glu Ser Leu Thr Ser
65                  70                  75                  80

Pro Glu Ile Arg Asp Gln Phe Ile Glu Glu Tyr Leu Asp Glu Ala Asn
                85                  90                  95

Ile Arg Asp Arg Gln Thr Lys Val Ala Ile Arg Glu Leu Leu His Gly
            100                 105                 110

Ile Lys Asp Asn Gln Glu Leu Val Glu Lys Thr Met Ala Gly Ile Gln
        115                 120                 125

Lys Val Glu Leu Pro Glu Ile Pro Asp Glu Ala Lys Asp Leu Thr Asp
    130                 135                 140

Leu Val Glu Ser Asp Tyr Pro Phe Ala Ile Asp Pro Met Pro Asn Leu
145                 150                 155                 160

Tyr Phe Thr Arg Asp Pro Phe Ala Thr Ile Gly Asn Ala Val Ser Leu
                165                 170                 175

Asn His Met Phe Ala Asp Thr Arg Asn Arg Glu Thr Leu Tyr Gly Lys
            180                 185                 190

Tyr Ile Phe Lys Tyr His Pro Ile Tyr Gly Gly Lys Val Asp Leu Val
        195                 200                 205

Tyr Asn Arg Glu Glu Asp Thr Arg Ile Glu Gly Asp Glu Leu Val
    210                 215                 220

Leu Ser Lys Asp Val Leu Ala Val Gly Ile Ser Gln Arg Thr Asp Ala
225                 230                 235                 240

Ala Ser Ile Glu Lys Leu Leu Val Asn Ile Phe Lys Lys Asn Val Gly
                245                 250                 255

Phe Lys Lys Val Leu Ala Phe Glu Phe Ala Asn Asn Arg Lys Phe Met
            260                 265                 270

His Leu Asp Thr Val Phe Thr Met Val Asp Tyr Asp Lys Phe Thr Ile
        275                 280                 285

His Pro Glu Ile Glu Gly Asp Leu His Val Tyr Ser Val Thr Tyr Glu
    290                 295                 300

Asn Glu Lys Leu Lys Ile Val Glu Glu Lys Gly Asp Leu Ala Glu Leu
305                 310                 315                 320

Leu Ala Gln Asn Leu Gly Val Glu Lys Val His Leu Ile Arg Cys Gly
                325                 330                 335

Gly Gly Asn Ile Val Ala Ala Ala Arg Glu Gln Trp Asn Asp Gly Ser
            340                 345                 350

Asn Thr Leu Thr Ile Ala Pro Gly Val Val Val Tyr Asp Arg Asn
        355                 360                 365

Thr Val Thr Asn Lys Ile Leu Glu Glu Tyr Gly Leu Arg Leu Ile Lys
    370                 375                 380

Ile Arg Gly Ser Glu Leu Val Arg Gly Arg Gly Pro Arg Cys Met
385                 390                 395                 400

Ser Met Pro Phe Glu Arg Glu Glu Val
                405
```

<210> SEQ ID NO 36
<211> LENGTH: 467
<212> TYPE: PRT
<213> ORGANISM: Artificial Sequence
<220> FEATURE:
<223> OTHER INFORMATION: the sequence is synthesized

<400> SEQUENCE: 36

```
Met Ser Val Phe Asp Ser Lys Phe Lys Gly Ile His Val Tyr Ser Glu
1               5                   10                  15

Ile Gly Glu Leu Glu Ser Val Leu His Glu Pro Gly Arg Glu Ile
            20                  25                  30

Asp Tyr Ile Thr Pro Ala Arg Leu Asp Glu Leu Leu Phe Ser Ala Ile
            35                  40                  45

Leu Glu Ser His Asp Ala Arg Lys Glu His Lys Gln Phe Val Ala Glu
50                  55                  60

Leu Lys Ala Asn Asp Ile Asn Val Val Glu Leu Ile Asp Leu Val Ala
65                  70                  75                  80

Glu Thr Tyr Asp Leu Ala Ser Gln Glu Ala Lys Asp Lys Leu Ile Glu
                85                  90                  95

Glu Phe Leu Glu Asp Ser Glu Pro Val Leu Ser Glu Glu His Lys Val
            100                 105                 110

Val Val Arg Asn Phe Leu Lys Ala Lys Lys Thr Ser Arg Glu Leu Val
        115                 120                 125

Glu Ile Met Met Ala Gly Ile Thr Lys Tyr Asp Leu Gly Ile Glu Ala
    130                 135                 140

Asp His Glu Leu Ile Val Asp Pro Met Pro Asn Leu Tyr Phe Thr Arg
145                 150                 155                 160

Asp Pro Phe Ala Ser Val Gly Asn Gly Val Thr Ile His Tyr Met Arg
                165                 170                 175

Tyr Lys Val Arg Gln Arg Glu Thr Leu Phe Ser Arg Phe Val Phe Ser
            180                 185                 190

Asn His Pro Lys Leu Ile Asn Thr Pro Trp Tyr Tyr Asp Pro Ser Leu
        195                 200                 205

Lys Leu Ser Ile Glu Gly Gly Asp Val Phe Ile Tyr Asn Asn Asp Thr
    210                 215                 220

Leu Val Val Gly Val Ser Glu Arg Thr Asp Leu Gln Thr Val Thr Leu
225                 230                 235                 240

Leu Ala Lys Asn Ile Val Ala Asn Lys Glu Cys Glu Phe Lys Arg Ile
                245                 250                 255

Val Ala Ile Asn Val Pro Lys Trp Thr Asn Leu Met His Leu Asp Thr
            260                 265                 270

Trp Leu Thr Met Leu Asp Lys Asp Lys Phe Leu Tyr Ser Pro Ile Ala
        275                 280                 285

Asn Asp Val Phe Lys Phe Trp Asp Tyr Asp Leu Val Asn Gly Gly Ala
    290                 295                 300

Glu Pro Gln Pro Val Glu Asn Gly Leu Pro Leu Glu Gly Leu Leu Gln
305                 310                 315                 320

Ser Ile Ile Asn Lys Lys Pro Val Leu Ile Pro Ile Ala Gly Glu Gly
                325                 330                 335

Ala Ser Gln Met Glu Ile Glu Arg Glu Thr His Phe Asp Gly Thr Asn
            340                 345                 350

Tyr Leu Ala Ile Arg Pro Gly Val Val Ile Gly Tyr Ser Arg Asn Glu
        355                 360                 365
```

```
Lys Thr Asn Ala Ala Leu Glu Ala Ala Gly Ile Lys Val Leu Pro Phe
370                 375                 380

His Gly Asn Gln Leu Ser Leu Gly Met Gly Asn Ala Arg Cys Met Ser
385                 390                 395                 400

Met Pro Leu Ser Arg Lys Asp Val Lys Trp Gly Ser His His His His
                405                 410                 415

His His Ala Asn Ser Leu Ala Glu Ala Lys Val Leu Ala Asn Arg Glu
            420                 425                 430

Leu Asp Lys Tyr Gly Val Ser Asp Phe Tyr Lys Arg Leu Ile Asn Lys
            435                 440                 445

Ala Lys Thr Val Glu Gly Val Glu Ala Leu Lys Leu His Ile Leu Ala
450                 455                 460

Ala Leu Pro
465

<210> SEQ ID NO 37
<211> LENGTH: 467
<212> TYPE: PRT
<213> ORGANISM: Artificial Sequence
<220> FEATURE:
<223> OTHER INFORMATION: the sequence is synthesized

<400> SEQUENCE: 37

Met Ser Val Phe Asp Ser Lys Phe Lys Gly Ile His Val Tyr Ser Glu
1               5                   10                  15

Ile Gly Glu Leu Glu Ser Val Leu Val His Glu Pro Gly Arg Glu Ile
                20                  25                  30

Asp Tyr Ile Thr Pro Ala Arg Leu Asp Glu Leu Leu Phe Ser Ala Ile
            35                  40                  45

Leu Glu Ser His Asp Ala Arg Lys Glu His Lys Gln Phe Val Ala Glu
        50                  55                  60

Leu Lys Ala Asn Asp Ile Asn Val Val Glu Leu Ile Asp Leu Val Ala
65                  70                  75                  80

Glu Thr Tyr Asp Leu Ala Ser Gln Glu Ala Lys Asp Lys Leu Ile Glu
                85                  90                  95

Glu Phe Leu Glu Asp Ser Glu Pro Val Leu Ser Glu Glu His Lys Val
            100                 105                 110

Val Val Arg Asn Phe Leu Lys Ala Lys Lys Thr Ser Arg Glu Leu Val
        115                 120                 125

Glu Ile Met Met Ala Gly Ile Thr Lys Tyr Asp Leu Gly Ile Glu Ala
130                 135                 140

Asp His Glu Leu Ile Val Asp Pro Met Pro Asn Leu Tyr Phe Thr Arg
145                 150                 155                 160

Asp Pro Phe Ala Ser Val Gly Asn Gly Val Thr Ile His Tyr Met Arg
                165                 170                 175

Tyr Lys Val Arg Gln Arg Glu Thr Leu Phe Ser Arg Phe Val Phe Ser
            180                 185                 190

Asn His Pro Lys Leu Ile Asn Thr Pro Trp Tyr Tyr Asp Pro Ser Leu
        195                 200                 205

Lys Leu Ser Ile Glu Gly Gly Asp Val Phe Ile Tyr Asn Asn Asp Thr
210                 215                 220

Leu Val Val Gly Val Ser Glu Arg Thr Asp Leu Gln Thr Val Thr Leu
225                 230                 235                 240

Leu Ala Lys Asn Ile Val Ala Asn Lys Glu Cys Glu Phe Lys Arg Ile
                245                 250                 255
```

Val Ala Ile Asn Val Pro Lys Trp Thr Asn Leu Met His Leu Asp Thr
            260                 265                 270

Trp Leu Thr Met Leu Asp Lys Asp Lys Phe Leu Tyr Ser Pro Ile Ala
        275                 280                 285

Asn Asp Val Phe Lys Phe Trp Asp Tyr Asp Leu Val Asn Gly Gly Ala
    290                 295                 300

Glu Pro Gln Pro Val Glu Asn Gly Leu Pro Leu Glu Gly Leu Leu Gln
305                 310                 315                 320

Ser Ile Ile Asn Lys Lys Pro Val Leu Ile Pro Ile Ala Gly Glu Gly
                325                 330                 335

Ala Ser Gln Met Glu Ile Glu Arg Glu Thr His Phe Asp Gly Thr Asn
            340                 345                 350

Tyr Leu Ala Ile Arg Pro Gly Val Val Ile Gly Tyr Ser Arg Asn Glu
        355                 360                 365

Lys Thr Asn Ala Ala Leu Glu Ala Ala Gly Ile Lys Val Leu Pro Phe
    370                 375                 380

His Gly Asn Gln Leu Ser Leu Gly Met Gly Asn Ala Arg Cys Met Ser
385                 390                 395                 400

Met Pro Leu Ser Arg Lys Asp Val Lys Trp Ala Gln His Asp Glu Ala
                405                 410                 415

Val Asp Ala Asn Ser Leu Ala Glu Ala Lys Val Leu Ala Asn Arg Glu
            420                 425                 430

Leu Asp Lys Tyr Gly Val Ser Asp Tyr Tyr Lys Asn Leu Ile Asn Asn
        435                 440                 445

Ala Lys Thr Val Glu Gly Val Lys Ala Leu Ile Asp Glu Ile Leu Ala
    450                 455                 460

Ala Leu Pro
465

<210> SEQ ID NO 38
<211> LENGTH: 473
<212> TYPE: PRT
<213> ORGANISM: Artificial Sequence
<220> FEATURE:
<223> OTHER INFORMATION: the sequence is synthesized

<400> SEQUENCE: 38

Met Ser Val Phe Asp Ser Lys Phe Lys Gly Ile His Val Tyr Ser Glu
1               5                   10                  15

Ile Gly Glu Leu Glu Ser Val Leu Val His Pro Gly Arg Glu Ile
            20                  25                  30

Asp Tyr Ile Thr Pro Ala Arg Leu Asp Glu Leu Leu Phe Ser Ala Ile
        35                  40                  45

Leu Glu Ser His Asp Ala Arg Lys Glu His Lys Gln Phe Val Ala Glu
    50                  55                  60

Leu Lys Ala Asn Asp Ile Asn Val Val Glu Leu Ile Asp Leu Val Ala
65                  70                  75                  80

Glu Thr Tyr Asp Leu Ala Ser Gln Glu Ala Lys Asp Lys Leu Ile Glu
                85                  90                  95

Glu Phe Leu Glu Asp Ser Glu Pro Val Leu Ser Glu Glu His Lys Val
            100                 105                 110

Val Val Arg Asn Phe Leu Lys Ala Lys Lys Thr Ser Arg Glu Leu Val
        115                 120                 125

Glu Ile Met Met Ala Gly Ile Thr Lys Tyr Asp Leu Gly Ile Glu Ala
    130                 135                 140

Asp His Glu Leu Ile Val Asp Pro Met Pro Asn Leu Tyr Phe Thr Arg
145                 150                 155                 160

Asp Pro Phe Ala Ser Val Gly Asn Gly Val Thr Ile His Tyr Met Arg
                165                 170                 175

Tyr Lys Val Arg Gln Arg Glu Thr Leu Phe Ser Arg Phe Val Phe Ser
            180                 185                 190

Asn His Pro Lys Leu Ile Asn Thr Pro Trp Tyr Tyr Asp Pro Ser Leu
        195                 200                 205

Lys Leu Ser Ile Glu Gly Gly Asp Val Phe Ile Tyr Asn Asn Asp Thr
    210                 215                 220

Leu Val Val Gly Val Ser Glu Arg Thr Asp Leu Gln Thr Val Thr Leu
225                 230                 235                 240

Leu Ala Lys Asn Ile Val Ala Asn Lys Glu Cys Glu Phe Lys Arg Ile
                245                 250                 255

Val Ala Ile Asn Val Pro Lys Trp Thr Asn Leu Met His Leu Asp Thr
            260                 265                 270

Trp Leu Thr Met Leu Asp Lys Asp Lys Phe Leu Tyr Ser Pro Ile Ala
        275                 280                 285

Asn Asp Val Phe Lys Phe Trp Asp Tyr Asp Leu Val Asn Gly Gly Ala
    290                 295                 300

Glu Pro Gln Pro Val Glu Asn Gly Leu Pro Leu Gly Leu Leu Gln
305                 310                 315                 320

Ser Ile Ile Asn Lys Lys Pro Val Leu Ile Pro Ile Ala Gly Glu Gly
                325                 330                 335

Ala Ser Gln Met Glu Ile Glu Arg Glu Thr His Phe Asp Gly Thr Asn
            340                 345                 350

Tyr Leu Ala Ile Arg Pro Gly Val Val Ile Gly Tyr Ser Arg Asn Glu
        355                 360                 365

Lys Thr Asn Ala Ala Leu Glu Ala Ala Gly Ile Lys Val Leu Pro Phe
    370                 375                 380

His Gly Asn Gln Leu Ser Leu Gly Met Gly Asn Ala Arg Cys Met Ser
385                 390                 395                 400

Met Pro Leu Ser Arg Lys Asp Val Lys Trp His His His His His
                405                 410                 415

Ala Gln His Asp Glu Ala Val Asp Ala Asn Ser Leu Ala Glu Ala Lys
            420                 425                 430

Val Leu Ala Asn Arg Glu Leu Asp Lys Tyr Gly Val Ser Asp Tyr Tyr
        435                 440                 445

Lys Asn Leu Ile Asn Asn Ala Lys Thr Val Glu Gly Val Lys Ala Leu
    450                 455                 460

Ile Asp Glu Ile Leu Ala Ala Leu Pro
465                 470

<210> SEQ ID NO 39
<211> LENGTH: 473
<212> TYPE: PRT
<213> ORGANISM: Artificial Sequence
<220> FEATURE:
<223> OTHER INFORMATION: the sequence is synthesized

<400> SEQUENCE: 39

Met Ser Val Phe Asp Ser Lys Phe Lys Gly Ile His Val Tyr Ser Glu
1               5                   10                  15

Ile Gly Glu Leu Glu Ser Val Leu Val His Glu Pro Gly Arg Glu Ile
            20                  25                  30

-continued

```
Asp Tyr Ile Thr Pro Ala Arg Leu Asp Glu Leu Leu Phe Ser Ala Ile
         35                  40                  45
Leu Glu Ser His Asp Ala Arg Lys Glu His Lys Gln Phe Val Ala Glu
 50                  55                  60
Leu Lys Ala Asn Asp Ile Asn Val Val Glu Leu Ile Asp Leu Val Ala
 65                  70                  75                  80
Glu Thr Tyr Asp Leu Ala Ser Gln Glu Ala Lys Asp Lys Leu Ile Glu
             85                  90                  95
Glu Phe Leu Glu Asp Ser Glu Pro Val Leu Ser Glu Glu His Lys Val
            100                 105                 110
Val Val Arg Asn Phe Leu Lys Ala Lys Lys Thr Ser Arg Glu Leu Val
            115                 120                 125
Glu Ile Met Met Ala Gly Ile Thr Lys Tyr Asp Leu Gly Ile Glu Ala
            130                 135                 140
Asp His Glu Leu Ile Val Asp Pro Met Pro Asn Leu Tyr Phe Thr Arg
145                 150                 155                 160
Asp Pro Phe Ala Ser Val Gly Asn Gly Val Thr Ile His Tyr Met Arg
                165                 170                 175
Tyr Lys Val Arg Gln Arg Glu Thr Leu Phe Ser Arg Phe Val Phe Ser
                180                 185                 190
Asn His Pro Lys Leu Ile Asn Thr Pro Trp Tyr Tyr Asp Pro Ser Leu
        195                 200                 205
Lys Leu Ser Ile Glu Gly Gly Asp Val Phe Ile Tyr Asn Asn Asp Thr
    210                 215                 220
Leu Val Val Gly Val Ser Glu Arg Thr Asp Leu Gln Thr Val Thr Leu
225                 230                 235                 240
Leu Ala Lys Asn Ile Val Ala Asn Lys Glu Cys Glu Phe Lys Arg Ile
                245                 250                 255
Val Ala Ile Asn Val Pro Lys Trp Thr Asn Leu Met His Leu Asp Thr
                260                 265                 270
Trp Leu Thr Met Leu Asp Lys Asp Lys Phe Leu Tyr Ser Pro Ile Ala
        275                 280                 285
Asn Asp Val Phe Lys Phe Trp Asp Tyr Asp Leu Val Asn Gly Gly Ala
    290                 295                 300
Glu Pro Gln Pro Val Glu Asn Gly Leu Pro Leu Glu Gly Leu Leu Gln
305                 310                 315                 320
Ser Ile Ile Asn Lys Lys Pro Val Leu Ile Pro Ile Ala Gly Glu Gly
                325                 330                 335
Ala Ser Gln Met Glu Ile Glu Arg Glu Thr His Phe Asp Gly Thr Asn
            340                 345                 350
Tyr Leu Ala Ile Arg Pro Gly Val Val Ile Gly Tyr Ser Arg Asn Glu
        355                 360                 365
Lys Thr Asn Ala Ala Leu Glu Ala Ala Gly Ile Lys Val Leu Pro Phe
    370                 375                 380
His Gly Asn Gln Leu Ser Leu Gly Met Gly Asn Ala Arg Cys Met Ser
385                 390                 395                 400
Met Pro Leu Ser Arg Lys Asp Val Lys Trp Ala Gln His Asp Glu Ala
                405                 410                 415
Val Asp Ala Asn Ser Leu Ala Glu Ala Lys Val Leu Ala Asn Arg Glu
            420                 425                 430
Leu Asp Lys Tyr Gly Val Ser Asp Tyr Tyr Lys Asn Leu Ile Asn Asn
        435                 440                 445
```

Ala Lys Thr Val Glu Gly Val Lys Ala Leu Ile Asp Glu Ile Leu Ala
    450                 455                 460

Ala Leu Pro His His His His His
465                 470

<210> SEQ ID NO 40
<211> LENGTH: 483
<212> TYPE: PRT
<213> ORGANISM: Artificial Sequence
<220> FEATURE:
<223> OTHER INFORMATION: the sequence is synthesized

<400> SEQUENCE: 40

Met His His His His His His Asp Glu Ala Val Asp Ala Asn Ser Leu
1               5                   10                  15

Ala Glu Ala Lys Val Leu Ala Asn Arg Glu Leu Asp Lys Tyr Gly Val
            20                  25                  30

Ser Asp Tyr Tyr Lys Asn Leu Ile Asn Asn Ala Lys Thr Val Glu Gly
        35                  40                  45

Val Lys Ala Leu Ile Asp Glu Ile Leu Ala Ala Leu Pro Ser Gly Ser
    50                  55                  60

Asn Asn Asn Asn Asn Asn Gly Ser Gly Gly Ser Val Phe Asp Ser Lys
65                  70                  75                  80

Phe Lys Gly Ile His Val Tyr Ser Glu Ile Gly Glu Leu Glu Ser Val
                85                  90                  95

Leu Val His Glu Pro Gly Arg Glu Ile Asp Tyr Ile Thr Pro Ala Arg
            100                 105                 110

Leu Asp Glu Leu Leu Phe Ser Ala Ile Leu Glu Ser His Asp Ala Arg
        115                 120                 125

Lys Glu His Lys Gln Phe Val Ala Glu Leu Lys Ala Asn Asp Ile Asn
    130                 135                 140

Val Val Glu Leu Ile Asp Leu Val Ala Glu Thr Tyr Asp Leu Ala Ser
145                 150                 155                 160

Gln Glu Ala Lys Asp Lys Leu Ile Glu Glu Phe Leu Glu Asp Ser Glu
                165                 170                 175

Pro Val Leu Ser Glu Glu His Lys Val Val Arg Asn Phe Leu Lys
            180                 185                 190

Ala Lys Lys Thr Ser Arg Glu Leu Val Glu Ile Met Met Ala Gly Ile
        195                 200                 205

Thr Lys Tyr Asp Leu Gly Ile Glu Ala Asp His Glu Leu Ile Val Asp
    210                 215                 220

Pro Met Pro Asn Leu Tyr Phe Thr Arg Asp Pro Phe Ala Ser Val Gly
225                 230                 235                 240

Asn Gly Val Thr Ile His Tyr Met Arg Tyr Lys Val Arg Gln Arg Glu
                245                 250                 255

Thr Leu Phe Ser Arg Phe Val Phe Ser Asn His Pro Lys Leu Ile Asn
            260                 265                 270

Thr Pro Trp Tyr Tyr Asp Pro Ser Leu Lys Leu Ser Ile Glu Gly Gly
        275                 280                 285

Asp Val Phe Ile Tyr Asn Asn Asp Thr Leu Val Gly Val Ser Glu
    290                 295                 300

Arg Thr Asp Leu Gln Thr Val Thr Leu Leu Ala Lys Asn Ile Val Ala
305                 310                 315                 320

Asn Lys Glu Cys Glu Phe Lys Arg Ile Val Ala Ile Asn Val Pro Lys
                325                 330                 335

```
Trp Thr Asn Leu Met His Leu Asp Thr Trp Leu Thr Met Leu Asp Lys
                340                 345                 350

Asp Lys Phe Leu Tyr Ser Pro Ile Ala Asn Asp Val Phe Lys Phe Trp
        355                 360                 365

Asp Tyr Asp Leu Val Asn Gly Gly Ala Glu Pro Gln Pro Val Glu Asn
370                 375                 380

Gly Leu Pro Leu Glu Gly Leu Leu Gln Ser Ile Ile Asn Lys Lys Pro
385                 390                 395                 400

Val Leu Ile Pro Ile Ala Gly Glu Gly Ala Ser Gln Met Glu Ile Glu
                405                 410                 415

Arg Glu Thr His Phe Asp Gly Thr Asn Tyr Leu Ala Ile Arg Pro Gly
                420                 425                 430

Val Val Ile Gly Tyr Ser Arg Asn Glu Lys Thr Asn Ala Ala Leu Glu
                435                 440                 445

Ala Ala Gly Ile Lys Val Leu Pro Phe His Gly Asn Gln Leu Ser Leu
                450                 455                 460

Gly Met Gly Asn Ala Arg Cys Met Ser Met Pro Leu Ser Arg Lys Asp
465                 470                 475                 480

Val Lys Trp

<210> SEQ ID NO 41
<211> LENGTH: 484
<212> TYPE: PRT
<213> ORGANISM: Artificial Sequence
<220> FEATURE:
<223> OTHER INFORMATION: the sequence is synthesized

<400> SEQUENCE: 41

Met Gly His His His His His His Asp Glu Ala Val Asp Ala Asn Ser
1               5                   10                  15

Leu Ala Glu Ala Lys Val Leu Ala Asn Arg Glu Leu Asp Lys Tyr Gly
                20                  25                  30

Val Ser Asp Tyr Tyr Lys Asn Leu Ile Asn Asn Ala Lys Thr Val Glu
            35                  40                  45

Gly Val Lys Ala Leu Ile Asp Glu Ile Leu Ala Ala Leu Pro Ser Gly
        50                  55                  60

Ser Asn Asn Asn Asn Asn Gly Ser Gly Gly Lys His Pro Ile His
65                  70                  75                  80

Val Thr Ser Glu Ile Gly Glu Leu Gln Thr Val Leu Leu Lys Arg Pro
                85                  90                  95

Gly Lys Glu Val Glu Asn Leu Thr Pro Asp Tyr Leu Gln Gln Leu Leu
                100                 105                 110

Phe Asp Asp Ile Pro Tyr Leu Pro Ile Ile Gln Lys Glu His Asp Tyr
            115                 120                 125

Phe Ala Gln Thr Leu Arg Asn Arg Gly Val Glu Val Leu Tyr Leu Glu
        130                 135                 140

Lys Leu Ala Ala Glu Ala Leu Val Asp Lys Lys Leu Arg Glu Glu Phe
145                 150                 155                 160

Val Asp Arg Ile Leu Lys Glu Gly Gln Ala Asp Val Asn Val Ala His
                165                 170                 175

Gln Thr Leu Lys Glu Tyr Leu Leu Ser Phe Ser Asn Glu Glu Leu Ile
                180                 185                 190

Gln Lys Ile Met Gly Gly Val Arg Lys Asn Glu Ile Glu Thr Ser Lys
            195                 200                 205
```

```
Lys Thr His Leu Tyr Glu Leu Met Glu Asp His Tyr Pro Phe Tyr Leu
    210                 215                 220

Asp Pro Met Pro Asn Leu Tyr Phe Thr Arg Asp Pro Ala Ala Ser Val
225                 230                 235                 240

Gly Asp Gly Leu Thr Ile Asn Lys Met Arg Glu Pro Ala Arg Arg Arg
                245                 250                 255

Glu Ser Leu Phe Met Glu Tyr Ile Ile Lys Tyr His Pro Arg Phe Ala
            260                 265                 270

Lys His Asn Val Pro Ile Trp Leu Asp Arg Asp Tyr Lys Phe Pro Ile
        275                 280                 285

Glu Gly Gly Asp Glu Leu Ile Leu Asn Glu Thr Ile Ala Ile Gly
290                 295                 300

Val Ser Ala Arg Thr Ser Ala Lys Ala Ile Glu Arg Leu Ala Lys Asn
305                 310                 315                 320

Leu Phe Ser Arg Gln Asn Lys Ile Lys Lys Val Leu Ala Ile Glu Ile
                325                 330                 335

Pro Lys Cys Arg Ala Phe Met His Leu Asp Thr Val Phe Thr Met Val
                340                 345                 350

Asp Tyr Asp Lys Phe Thr Ile His Pro Ala Ile Gln Gly Pro Lys Gly
            355                 360                 365

Asn Met Asn Ile Tyr Ile Leu Glu Lys Gly Ala Asp Glu Glu Thr Leu
370                 375                 380

Lys Ile Thr His Arg Thr Ser Leu Met Glu Ala Leu Lys Glu Val Leu
385                 390                 395                 400

Asp Leu Ser Glu Leu Val Leu Ile Pro Cys Gly Gly Asp Val Ile
                405                 410                 415

Ala Ser Ala Arg Glu Gln Trp Asn Asp Gly Ser Asn Thr Leu Ala Ile
                420                 425                 430

Ala Pro Gly Val Val Val Thr Tyr Asp Arg Asn Tyr Val Ser Asn Thr
                435                 440                 445

Leu Leu Arg Glu His Gly Ile Glu Val Ile Glu Val Leu Ser Ser Glu
                450                 455                 460

Leu Ser Arg Gly Arg Gly Gly Pro Arg Cys Met Ser Met Pro Ile Val
465                 470                 475                 480

Arg Lys Asp Ile

<210> SEQ ID NO 42
<211> LENGTH: 335
<212> TYPE: PRT
<213> ORGANISM: Artificial Sequence
<220> FEATURE:
<223> OTHER INFORMATION: the sequence is synthesized

<400> SEQUENCE: 42

Met Ala Gln His Asp Glu Ala Val Asp Ala Asn Ser Leu Ala Glu Ala
1               5                   10                  15

Lys Val Leu Ala Asn Arg Glu Leu Asp Lys Tyr Gly Val Ser Asp Tyr
                20                  25                  30

Tyr Lys Asn Leu Ile Asn Asn Ala Lys Thr Val Glu Gly Val Lys Ala
            35                  40                  45

Leu Ile Asp Glu Ile Leu Ala Ala Leu Pro Glu Phe Leu Glu Gly Ser
        50                  55                  60

Ser Cys Ile Thr Gly Asp Ala Leu Val Ala Leu Pro Glu Gly Glu Ser
65                  70                  75                  80
```

Val Arg Ile Ala Asp Ile Val Pro Gly Ala Arg Pro Asn Ser Asp Asn
                 85                  90                  95

Ala Ile Asp Leu Lys Val Leu Asp Arg His Gly Asn Pro Val Leu Ala
            100                 105                 110

Asp Arg Leu Phe His Ser Gly Glu His Pro Val Tyr Thr Val Arg Thr
            115                 120                 125

Val Glu Gly Leu Arg Val Thr Gly Thr Ala Asn His Pro Leu Leu Cys
130                 135                 140

Leu Val Asp Val Ala Gly Val Pro Thr Leu Leu Trp Lys Leu Ile Asp
145                 150                 155                 160

Glu Ile Lys Pro Gly Asp Tyr Ala Val Ile Gln Arg Ser Ala Phe Ser
                165                 170                 175

Val Asp Cys Ala Gly Phe Ala Arg Gly Lys Pro Glu Phe Ala Pro Thr
            180                 185                 190

Thr Tyr Thr Val Gly Val Pro Gly Leu Val Arg Phe Leu Glu Ala His
            195                 200                 205

His Arg Asp Pro Asp Ala Gln Ala Ile Ala Asp Glu Leu Thr Asp Gly
        210                 215                 220

Arg Phe Tyr Tyr Ala Lys Val Ala Ser Val Thr Asp Ala Gly Val Gln
225                 230                 235                 240

Pro Val Tyr Ser Leu Arg Val Asp Thr Ala Asp His Ala Phe Ile Thr
                245                 250                 255

Asn Gly Phe Val Ser His Ala Thr Gly Leu Thr Gly Leu Asn Ser Gly
            260                 265                 270

Leu Thr Thr Asn Pro Gly Val Ser Ala Trp Gln Val Asn Thr Ala Tyr
            275                 280                 285

Thr Ala Gly Gln Leu Val Thr Tyr Asn Gly Lys Thr Tyr Lys Cys Leu
290                 295                 300

Gln Pro His Thr Ser Leu Ala Gly Trp Glu Pro Ser Asn Val Pro Ala
305                 310                 315                 320

Leu Trp Gln Leu Gln Gly Asp Pro Ile Thr Ile Thr Ile Thr Lys
                325                 330                 335

<210> SEQ ID NO 43
<211> LENGTH: 636
<212> TYPE: PRT
<213> ORGANISM: Artificial Sequence
<220> FEATURE:
<223> OTHER INFORMATION: the sequence is synthesized

<400> SEQUENCE: 43

Met Lys Ile Glu Glu Gly Lys Leu Thr Asn Pro Gly Val Ser Ala Trp
1               5                   10                  15

Gln Val Asn Thr Ala Tyr Thr Ala Gly Gln Leu Val Thr Tyr Asn Gly
                20                  25                  30

Lys Thr Tyr Lys Cys Leu Gln Pro His Thr Ser Leu Ala Gly Trp Glu
            35                  40                  45

Pro Ser Asn Val Pro Ala Leu Trp Gln Leu Gln Asn Asn Gly Asn Asn
        50                  55                  60

Gly Leu Glu Leu Arg Glu Ser Gly Ala Ile Ser Gly Asp Ser Leu Ile
65                  70                  75                  80

Ser Leu Ala Ser Thr Gly Lys Arg Val Ser Ile Lys Asp Leu Leu Asp
                85                  90                  95

Glu Lys Asp Phe Glu Ile Trp Ala Ile Asn Glu Gln Thr Met Lys Leu
            100                 105                 110

-continued

```
Glu Ser Ala Lys Val Ser Arg Val Phe Cys Thr Gly Lys Leu Val
            115                 120                 125
Tyr Ile Leu Lys Thr Arg Leu Gly Arg Thr Ile Lys Ala Thr Ala Asn
130                 135                 140
His Arg Phe Leu Thr Ile Asp Gly Trp Lys Arg Leu Asp Glu Leu Ser
145                 150                 155                 160
Leu Lys Glu His Ile Ala Leu Pro Arg Lys Leu Glu Ser Ser Ser Leu
                165                 170                 175
Gln Leu Ser Pro Glu Ile Glu Lys Leu Ser Gln Ser Asp Ile Tyr Trp
            180                 185                 190
Asp Ser Ile Val Ser Ile Thr Glu Thr Gly Val Glu Glu Val Phe Asp
195                 200                 205
Leu Thr Val Pro Gly Pro His Asn Phe Val Ala Asn Asp Ile Ile Val
210                 215                 220
His Asn Cys Ser Val Phe Asp Ser Lys Phe Lys Gly Ile His Val Tyr
225                 230                 235                 240
Ser Glu Ile Gly Glu Leu Glu Ser Val Leu Val His Glu Pro Gly Arg
                245                 250                 255
Glu Ile Asp Tyr Ile Thr Pro Ala Arg Leu Asp Glu Leu Leu Phe Ser
            260                 265                 270
Ala Ile Leu Glu Ser His Asp Ala Arg Lys Glu His Lys Gln Phe Val
275                 280                 285
Ala Glu Leu Lys Ala Asn Asp Ile Asn Val Val Glu Leu Ile Asp Leu
290                 295                 300
Val Ala Glu Thr Tyr Asp Leu Ala Ser Gln Glu Ala Lys Asp Lys Leu
305                 310                 315                 320
Ile Glu Glu Phe Leu Glu Asp Ser Glu Pro Val Leu Ser Glu Glu His
                325                 330                 335
Lys Val Val Val Arg Asn Phe Leu Lys Ala Lys Lys Thr Ser Arg Glu
            340                 345                 350
Leu Val Glu Ile Met Met Ala Gly Ile Thr Lys Tyr Asp Leu Gly Ile
355                 360                 365
Glu Ala Asp His Glu Leu Ile Val Asp Pro Met Pro Asn Leu Tyr Phe
370                 375                 380
Thr Arg Asp Pro Phe Ala Ser Val Gly Asn Gly Val Thr Ile His Tyr
385                 390                 395                 400
Met Arg Tyr Lys Val Arg Gln Arg Glu Thr Leu Phe Ser Arg Phe Val
                405                 410                 415
Phe Ser Asn His Pro Lys Leu Ile Asn Thr Pro Trp Tyr Tyr Asp Pro
            420                 425                 430
Ser Leu Lys Leu Ser Ile Glu Gly Gly Asp Val Phe Ile Tyr Asn Asn
435                 440                 445
Asp Thr Leu Val Val Gly Val Ser Glu Arg Thr Asp Leu Gln Thr Val
450                 455                 460
Thr Leu Leu Ala Lys Asn Ile Val Ala Asn Lys Glu Cys Glu Phe Lys
465                 470                 475                 480
Arg Ile Val Ala Ile Asn Val Pro Lys Trp Thr Asn Leu Met His Leu
                485                 490                 495
Asp Thr Trp Leu Thr Met Leu Asp Lys Asp Lys Phe Leu Tyr Ser Pro
            500                 505                 510
Ile Ala Asn Asp Val Phe Lys Phe Trp Asp Tyr Asp Leu Val Asn Gly
515                 520                 525
```

```
Gly Ala Glu Pro Gln Pro Val Glu Asn Gly Leu Pro Leu Glu Gly Leu
            530                 535                 540

Leu Gln Ser Ile Ile Asn Lys Lys Pro Val Leu Ile Pro Ile Ala Gly
545                 550                 555                 560

Glu Gly Ala Ser Gln Met Glu Ile Glu Arg Glu Thr His Phe Asp Gly
                565                 570                 575

Thr Asn Tyr Leu Ala Ile Arg Pro Gly Val Val Ile Gly Tyr Ser Arg
            580                 585                 590

Asn Glu Lys Thr Asn Ala Ala Leu Glu Ala Ala Gly Ile Lys Val Leu
            595                 600                 605

Pro Phe His Gly Asn Gln Leu Ser Leu Gly Met Gly Asn Ala Arg Cys
        610                 615                 620

Met Ser Met Pro Leu Ser Arg Lys Asp Val Lys Trp
625                 630                 635

<210> SEQ ID NO 44
<211> LENGTH: 1452
<212> TYPE: DNA
<213> ORGANISM: Artificial Sequence
<220> FEATURE:
<223> OTHER INFORMATION: the sequence is synthesized

<400> SEQUENCE: 44
atgcatcatc accatcacca tgatgaagcc gtggatgcga attccttagc tgaagctaaa      60
gtcttagcta acagagaact tgacaaatat ggagtaagtg actattacaa gaacctaatc     120
aacaatgcca aaactgttga aggtgtaaaa gcactgatag atgaaatttt agctgcatta     180
ccttcgggta gtaacaacaa taataacaat ggtagcggcg ttctgtatt tgacagtaaa      240 tttaaaggaa ttcacgttta ttcagaaatt ggtgaattag aatcagttct agttcacgaa     300
ccaggacgcg aaattgacta tattacacca gctagactag atgaattatt attctcagct     360
atcttagaaa gccacgatgc tagaaaagaa cacaaacaat cgtagcaga attaaaagca      420 aacgacatca atgttgttga attaattgat ttagttgctg aaacatatga tttagcatca     480
caagaagcta agacaaatt aatcgaagaa tttttagaag actcagaacc agttctatca      540
gaagaacaca agtagttgt aagaaacttc ttaaaagcta aaaaacatc aagagaatta       600 gtagaaatca tgatggcagg gatcacaaaa tacgatttag gtatcgaagc agatcacgaa     660
ttaatcgttg acccaatgcc aaacctatac ttcacacgtg acccatttgc atcagtaggt     720
aatggtgtaa caatccacta catgcgttac aaagttagac aacgtgaaac attattctca     780
agatttgtat tctcaaatca ccctaaacta attaacactc catggtacta cgaccccttca    840 ctaaaattat caatcgaagg tggggacgta tttatctaca caatgacac attagtagtt     900 ggtgtttctg aaagaactga cttacaaaca gttactttat tagctaaaaa cattgttgct     960
aataaagaat gtgaattcaa acgtattgtt gcaattaacg ttccaaaatg dacaaactta    1020
atgcacttag acacatggct aacaatgtta gacaaggaca aattcctata ctcaccaatc    1080
gctaatgacg tatttaaatt ctgggattat gacttagtaa acgtggagc agaaccacaa     1140 ccagttgaaa acggattacc tctagaagga ttattacaat caatcattaa caaaaaacca    1200
gttttaattc ctatcgcagg tgaaggtgct tcacaaatgg aaatcgaaag agaaacacac    1260
ttcgatggta caaactactt agcaattaga ccaggtgttg taattggtta ctcacgtaac    1320
gaaaaaacaa acgctgctct agaagctgca ggcattaaag ttcttccatt ccacggtaac    1380
```

```
caattatcat taggtatggg taacgctcgt tgtatgtcaa tgcctttatc acgtaaagat      1440
gttaagtggt aa                                                         1452

<210> SEQ ID NO 45
<211> LENGTH: 1455
<212> TYPE: DNA
<213> ORGANISM: Artificial Sequence
<220> FEATURE:
<223> OTHER INFORMATION: the sequence is synthesized

<400> SEQUENCE: 45
atgggtcatc atcaccatca ccatgatgaa gccgtggatg cgaacagctt agctgaagct        60
aaagtcttag ctaacagaga acttgacaaa tatggagtaa gtgactatta caagaaccta       120
atcaacaatg ccaaaactgt tgaaggtgta aaagcactga tagatgaaat tttagctgca       180
ttaccttcgg gtagtaacaa caataataac aatggtagcg gcggtaaaca tccgatacat       240
gttacttcag aaattgggga attacaaacg ttttattaa acgaccggg taaagaagtg         300 gaaaacttga cgccagatta tttgcagcaa ttattatttg acgatattcc atacctacca       360
attattcaaa aagagcatga ttattttgca caaacgttac gcaatcgggg tgttgaagtt       420
ctttatttag aaaaactagc cgctgaggcg ttagtagata aaaaacttcg agaagaattt       480
gttgatcgta ttttaaaaga aggacaggcc gacgtaaatg ttgcacatca aactttaaaa       540
gaatatttac tttcctttc aaatgaagaa ttaattcaaa aaattatggg cggtgtacgg       600
aaaaacgaaa ttgaaacaag taagaagaca catttatatg aattaatgga agatcattat       660 ccgtttact tagatccaat gcctaattta tattttactc gtgatccagc agctagcgtg       720
ggcgatggct taacgataaa taagatgaga gaaccagcgc gtagacgtga atcattattc       780
atggagtaca tcattaaata tcatccaaga tttgcaaaac ataatgtacc aatctggtta       840
gatcgtgatt ataaatttcc aattgaaggt ggcgacgagc taattttaaa tgaagaaaca       900
attgcgattg gagtatctgc tcgtacttca gctaaagcaa ttgaacgttt agcaaaaaat       960
ctctttagcc gacaaaataa aattaagaaa gtgttagcaa tagaaattcc aaaatgccga      1020
gcatttatgc atttagatac agtatttaca atggttgatt atgataagtt tacaattcac      1080
ccagctattc aagggccaaa agggaatatg aatatttata ttttagaaaa aggagcagat      1140
gaggaaactc ttaaaattac acatcgtact tctttaatgg aagcattaaa agaggtatta      1200
gacttaagtg aattagttct tattccatgt ggaggaggag atgtaattgc ttctgctcgt      1260
gaacaatgga atgatggctc gaacacatta gcaatcgcgc caggtgtagt tgttacatat      1320
gatcgcaact atgtatccaa tacgttatta cgggaacacg gtatagaagt gattgaggtg      1380
ctaagttcag aattatctcg tggtcgtggg ggtccacgtt gcatgagtat gccaattgtt      1440
cgtaaagata tttaa                                                      1455

<210> SEQ ID NO 46
<211> LENGTH: 46
<212> TYPE: PRT
<213> ORGANISM: Artificial Sequence
<220> FEATURE:
<223> OTHER INFORMATION: the sequence is synthesized
```

<400> SEQUENCE: 46

Leu Ala Glu Ala Lys Val Leu Ala Asn Arg Glu Leu Asp Lys Tyr Gly
1               5                   10                  15

Val Ser Asp Tyr Tyr Lys Asn Leu Ile Asn Asn Ala Lys Thr Val Glu
                20                  25                  30

Gly Val Lys Ala Leu Ile Asp Glu Ile Leu Ala Ala Leu Pro
            35                  40                  45

<210> SEQ ID NO 47
<211> LENGTH: 57
<212> TYPE: PRT
<213> ORGANISM: Artificial Sequence
<220> FEATURE:
<223> OTHER INFORMATION: the sequence is synthesized

<400> SEQUENCE: 47

Ala Gln His Asp Glu Ala Val Asp Ala Asn Ser Leu Ala Glu Ala Lys
1               5                   10                  15

Val Leu Ala Asn Arg Glu Leu Asp Lys Tyr Gly Val Ser Asp Tyr Tyr
                20                  25                  30

Lys Asn Leu Ile Asn Asn Ala Lys Thr Val Glu Gly Val Lys Ala Leu
            35                  40                  45

Ile Asp Glu Ile Leu Ala Ala Leu Pro
    50                  55

<210> SEQ ID NO 48
<211> LENGTH: 46
<212> TYPE: PRT
<213> ORGANISM: Artificial Sequence
<220> FEATURE:
<223> OTHER INFORMATION: the sequence is synthesized

<400> SEQUENCE: 48

Leu Ala Glu Ala Lys Val Leu Ala Asn Arg Glu Leu Asp Lys Tyr Gly
1               5                   10                  15

Val Ser Asp Phe Tyr Lys Arg Leu Ile Asn Lys Ala Lys Thr Val Glu
                20                  25                  30

Gly Val Glu Ala Leu Lys Leu His Ile Leu Ala Ala Leu Pro
            35                  40                  45

<210> SEQ ID NO 49
<211> LENGTH: 57
<212> TYPE: PRT
<213> ORGANISM: Artificial Sequence
<220> FEATURE:
<223> OTHER INFORMATION: the sequence is synthesized

<400> SEQUENCE: 49

Gly Ser His His His His His His Ala Asn Ser Leu Ala Glu Ala Lys
1               5                   10                  15

Val Leu Ala Asn Arg Glu Leu Asp Lys Tyr Gly Val Ser Asp Phe Tyr
                20                  25                  30

Lys Arg Leu Ile Asn Lys Ala Lys Thr Val Glu Gly Val Glu Ala Leu
            35                  40                  45

Lys Leu His Ile Leu Ala Ala Leu Pro
    50                  55

<210> SEQ ID NO 50
<211> LENGTH: 11
<212> TYPE: PRT
<213> ORGANISM: Artificial Sequence

```
<220> FEATURE:
<223> OTHER INFORMATION: the sequence is synthesized

<400> SEQUENCE: 50

Gly Ser His His His His His His Ala Asn Ser
1               5                   10

<210> SEQ ID NO 51
<211> LENGTH: 11
<212> TYPE: PRT
<213> ORGANISM: Artificial Sequence
<220> FEATURE:
<223> OTHER INFORMATION: the sequence is synthesized

<400> SEQUENCE: 51

Ala Gln His Asp Glu Ala Val Asp Ala Asn Ser
1               5                   10

<210> SEQ ID NO 52
<211> LENGTH: 8
<212> TYPE: PRT
<213> ORGANISM: Artificial Sequence
<220> FEATURE:
<223> OTHER INFORMATION: the sequence is synthesized

<400> SEQUENCE: 52

Asp Glu Ala Val Asp Ala Asn Ser
1               5

<210> SEQ ID NO 53
<211> LENGTH: 4
<212> TYPE: PRT
<213> ORGANISM: Artificial Sequence
<220> FEATURE:
<223> OTHER INFORMATION: the sequence is synthesized

<400> SEQUENCE: 53

Gly Ser Gly Gly
1
```

METHOD FOR CANCER TARGETING TREATMENT AND DETECTION OF ARGININE USING ALBUMIN-BINDING ARGININE DEIMINASE FUSION PROTEIN

CROSS-REFERENCE TO RELATED APPLICATION

The present application is a continuation-in-part application of U.S. non-provisional patent application Ser. No. 14/197,236 filed Mar. 5, 2014 and now granted under the U.S. Pat. No. 9,255,262, which claims benefit from U.S. provisional patent application Ser. No. 61/773,214 filed Mar. 6, 2013, and the disclosure of which are incorporated herein by reference in its entirety.

COPYRIGHT NOTICE/PERMISSION

A portion of the disclosure of this patent document contains material which is subject to copyright protection. The copyright owner has no objection to the facsimile reproduction by anyone of the patent document or the patent disclosure as it appears in the Patent and Trademark Office patent file or records, but otherwise reserves all copyright rights whatsoever. The following notice applies to the processes, experiments, and data as described below and in the drawings attached hereto: Copyright © 2014-15, Vision Global Holdings Limited, All Rights Reserved.

TECHNICAL FIELD

The present invention describes albumin-binding arginine deiminase (AAD) fusion protein that has been genetically modified to create a material having high activity and long in vivo half-life. The present invention further describes the designs for DNA and protein engineering for creating different AAD fusion proteins. The AAD fusion proteins can be isolated and purified from soluble fraction and insoluble fraction (inclusion bodies) of the crude proteins. The present invention further relates to albumin-binding arginine deiminase-containing pharmaceutical compositions for cancer targeting treatment and curing arginine-dependent diseases in humans and other animals. The AAD fusion protein can also be used as a component in a testing kit for detection of arginine.

BACKGROUND OF THE INVENTION

The incidence of pancreatic cancer, colon cancer, liver cancer, melanoma and cervical cancer in the worldwide population is increasing. Effective treatments for these diseases are urgently needed. In many types of cancer including leukemia, melanoma, pancreatic, colon, renal cell carcinoma, lung, prostate, breast, brain, cervical and liver cancers, the cancer cells are auxotrophic for arginine since they lack of expression of argininosuccinate synthetase (ASS), making these cancers excellent targets for arginine depletion therapy.

Arginine is a semi-essential amino acid for humans and other mammals. It can be synthesized from citrulline via a two step process catalyzed by the urea cycle enzymes argininosuccinate synthase (ASS) and argininosuccinate lyase (ASL). Arginine can be metabolized to ornithine by the enzyme arginase, and ornithine can be converted to citrulline by ornithine carbamoyltransferase (OTC) in the mitochondria. The citrulline can be utilized to synthesize arginine again. Normal cells usually do not require an exogenous supply of arginine for growth because of the abundant catalytic activity of ASS and ASL. In contrast, many types of cancers do not express ASS and therefore are auxotrophic for arginine. Their growth is dependent on arginine solely obtained from blood circulation. Therefore, targeting circulating arginine by using arginine-degrading enzymes is a feasible strategy to inhibit ASS-negative tumor growth [Feun et al., Curr. Pharm. Des. 14:1049-1057 (2008); Kuo et al., Oncotarget. 1:246-251 (2010)].

Arginine can be degraded by arginase, arginine decarboxylase, and arginine deiminase (ADI). Among them, arginine deiminase (ADI) appears to have the highest affinity for arginine (a low $K_m$ value). ADI converts arginine to citrulline and ammonia, the metabolites of the urea cycle. Unfortunately, ADI can only be found in prokaryotes e.g. *Mycoplasma* sp. There are some problems associated with the isolation and purification of ADI from prokaryotes. ADI isolated from *Pseudomonas putida* fails to exhibit efficacy in vivo because of its low enzymatic activity in neutral pH. ADI produced from *Escherichia coli* is enzymatically inactive and subsequently requires multiple denaturation and renaturation process which raises the subsequent cost of production.

As the native ADI is found in microorganisms, it is antigenic and rapidly cleared from circulation in a patient. The native form of ADI is immunogenic upon injection into human circulation with a short half-life (~4 hours) and elicits neutralizing antibodies [Ensor et al., Cancer Res. 62:5443-5450 (2002); Izzo et al., J. Clin. Oncol. 22:1815-1822 (2004)]. These shortcomings can be remedied by pegylation. Among various forms of pegylated ADI, ADI bound with PEG (molecular weight 20,000) via succinimidyl succinate (ADI-PEG 20) has been found to be an efficacious formulation. However, the activity of ADI after pegylation is greatly decreased on the order of 50% [Ensor et al., Cancer Res. 62:5443-5450 (2002)]. The previous attempts to create pegylated ADI resulted in materials that are not homogenous (due to the random attachment of PEG on protein surface Lys residues) and also difficult to characterize and perform quality control during the manufacturing process. Also, PEG is very expensive, greatly increasing the production cost. After the intravenous injection of pegylated ADI in vivo, leakage or detachment of free PEG is observed and the ADI (without PEG) can elicit the immunogenicity problem. Therefore, there is a need for improved cancer-treatment compositions, particularly, improved cancer-treatment compositions that have enhanced activity and in vivo half-life.

SUMMARY OF THE INVENTION

In the present invention, albumin-binding arginine deiminase (AAD) fusion protein has increased its activity and plasma half-life in order to efficiently deplete arginine in cancer cells. Native ADI may be found in microorganisms and is antigenic and rapidly cleared from circulation in a patient. The present invention constructs different AAD fusion proteins with one or two albumin-binding proteins to maintain high activity with longer in vivo half-life (at least 5 days of arginine depletion after one injection). In the present invention, the albumin binding protein in the AAD fusion protein product does not appear to influence its specific enzyme activity but instead appears to increase the circulating half-life. The specific activities of wild-type ADI and AAD fusion protein in the present invention are about 20 and about 19 U/mg (at physiological pH 7.4), respectively. In addition, the AAD fusion protein of the present invention is generally more soluble in most of the solutions than native or wild-type ADI of different organisms. Purification of native or wild-type ADI is also generally more difficult than the AAD fusion protein of the present invention.

In its broadest sense, the present invention provides an albumin-binding arginine deiminase fusion protein comprising a first portion comprising one or two components selected from an albumin-binding domain, an albumin-binding peptide or an albumin-binding protein(s) fused to a second portion comprising arginine deiminase to form the albumin-binding arginine deiminase fusion protein such that the albumin-binding arginine deiminase fusion protein retains the activity of arginine deiminase and is also able to bind serum albumin.

The present invention further relates to albumin-binding arginine deiminase (AAD) fusion protein-containing pharmaceutical compositions for targeted cancer treatment in humans and other animals. The first aspect of the present invention is to construct the modified AAD fusion protein with high activity against cancer cells. The second aspect of the present invention is to purify AAD fusion protein with high purity from both soluble and insoluble fractions of the crude proteins. The third aspect of the present invention is to lengthen the half-life of AAD fusion protein as it can bind to albumin very well in the circulation. The fourth aspect of the present invention is to provide a method of using the AAD fusion protein-containing pharmaceutical composition of the present invention for treating cancer by administering said composition to a subject in need thereof suffering from various tumors, cancers or diseases associated with tumors or cancers or other arginine-dependent diseases. The fifth aspect of the present invention is to use AAD fusion protein as a component in a testing kit for detection of arginine.

The AAD fusion protein of the present invention is also modified to avoid dissociation into albumin-binding protein and ADI such that it becomes more stable and has a longer half-life in circulation. ADI is fused to an albumin-binding domain/peptide/protein in AAD fusion product to extend the plasma half-life and reduce the immunogenicity of the fusion product. Albumin binding domain (ABD) is a peptide that binds albumin in the blood. There are different variants of ABD showing different or improved human serum albumin (HSA) affinities. Different variants of ABD can be constructed and can be fused to ADI. Unlike the naturally occurring ADI, this longer half-life property facilitates the depletion of arginine efficiently in cancerous cells, cancer stem cells and/or cancer progenitor cells.

The pharmaceutical composition containing AAD fusion protein can be used for intravenous (i.v.) injection (for rapid-acting dosage of medication) and intramuscular (i.m.) injection (for fairly rapid-acting and long-lasting dosage of medication). The application of AAD fusion protein in the present invention can be used in the treatment of various cancers such as pancreatic cancer, leukemia, melanoma, head and neck cancer, colorectal cancer, lung cancer, breast cancer, prostate cancer, cervical cancer, liver cancer, nasopharyngeal cancer, esophageal cancer and brain cancer. The present invention is directed to AAD fusion proteins, to methods of treating cancer, to methods of treating and/or inhibiting metastasis of cancerous tissue, and to methods of curing arginine-dependent diseases.

The method of the present invention also includes using a combination of different chemotherapeutic drugs and/or radiotherapy with the AAD fusion protein of the present invention to give a synergistic effect on cancer treatment.

In the presently claimed invention, an aspect relates to the use of the AAD fusion protein of the present invention as a component in a testing kit for detection of arginine in different samples (e.g. blood samples from cancer patients, food samples, cell cultures). Said testing kit comprises the AAD fusion protein of the present invention and a color reagent. When a sample is incubated with the AAD fusion protein and the color reagent of the testing kit in appropriate assay conditions, the arginine is converted by the AAD fusion protein into citrulline. The color reagent will be turned into pink color in the presence of citrulline. The presence of citrulline indicates the presence of arginine in the sample and the intensity of the pink color developed in the assay can be used to quantify the concentration of the arginine in the sample by measuring the color intensity of the reaction mixture in a spectrophotometer. The sample can be prepared in solution form before using the testing kit. The concentration of the arginine in the sample can be expressed by the following formula:

one unit of arginine deiminase activity=1 µmol of arginine being converted to 1 µmol of citrulline per minute.

In one embodiment, the AAD fusion protein of the present invention has a specific activity of about 19 U/mg at pH 7.4 and 37° C., which is comparable to the activity of wild-type ADI. There are many advantages of using the AAD fusion protein of the present invention over wild-type ADI as enzyme of the testing kit, such as (1) simple production method, (2) longer shelf-life and (3) higher solubility. For wild-type ADI, it is usually insoluble and difficult for purification. For our AAD fusion protein, it can be prepared both soluble and insoluble forms.

BRIEF DESCRIPTION OF THE DRAWINGS

FIG. 2 shows the sequence alignment for ADI in some bacterial species including *Mycoplasma arginini* (SEQ ID No. 23), *Lactococcus lactis* (SEQ ID No. 24), *Bacillus cereus* (SEQ ID No. 25) and *Bacillus licheniformis* (SEQ ID No. 26).

FIG. 3 shows the designs and amino acid sequences for different AAD fusion proteins originated from *Mycoplasma arginini* (A to E) and AAD fusion protein originated from *Bacillus cereus* (F).

FIG. 6 shows the (A) gene map, (B) nucleotide sequence (SEQ ID No. 44) and (C) amino acid sequence (SEQ ID No. 40) of His-ABD-PolyN-ADI. (ADI: the *Mycoplasma arginini* ADI)

FIG. 7 shows the (A) gene map, (B) nucleotide sequence (SEQ ID No. 45) and (C) amino acid sequence (SEQ ID No. 41) of His-ABD-PolyN-bcADI. (bcADI, the *Bacillus cereus* ADI)

FIG. 8 shows the expression and purification of AAD fusion protein: (A) AAD is ~90% soluble when expressed at 20° C. (lanes 2 and 3) and ~90% insoluble (inclusion body) when expressed at 37° C. (lanes 4 and 5); (B) The purified AAD fusion protein in sodium dodecyl sulfate polyacrylamide gel electrophoresis (SDS-PAGE) gel: lane 1, purified AAD fusion protein (52.8 kDa); lane 2, molecular weight marker.

FIG. 12 shows the effects of administration of AAD fusion protein in total of 10 U per week and/or GEM on (A) tumor size; (B) appearance of the Mia-paca-2 pancreatic cancer xenograft; (C) tumor volume and (D) body weight of the mice.

DEFINITIONS

Figure 1:
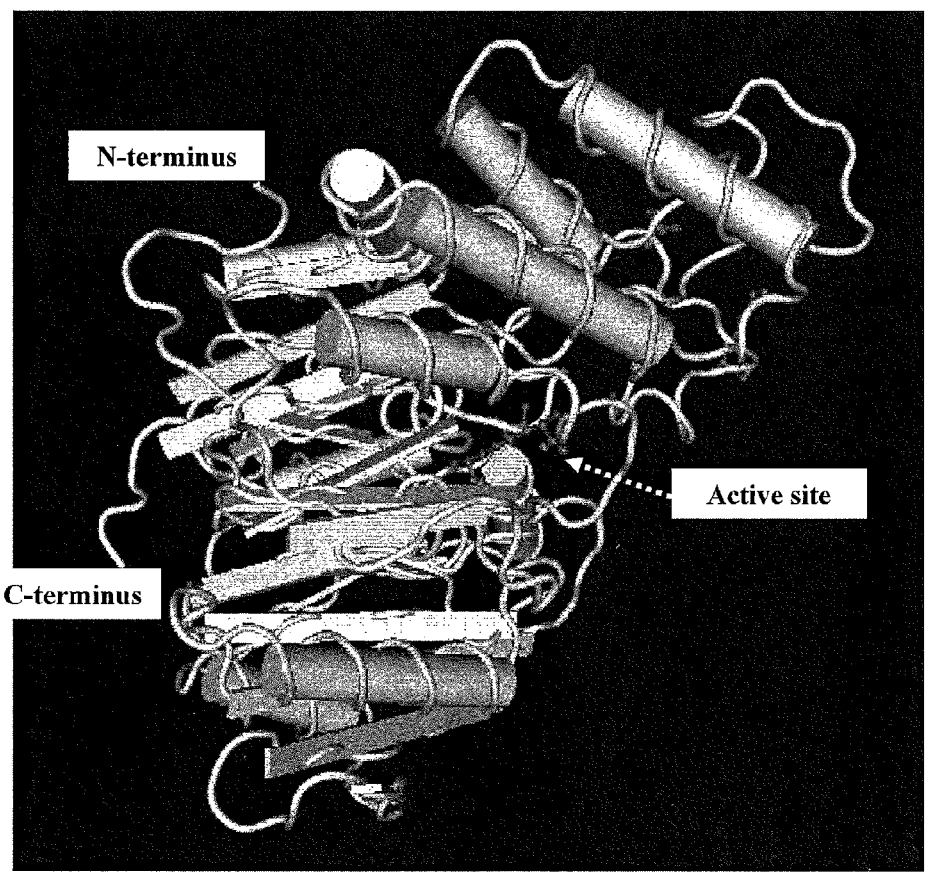
FIG. 1 shows the design approach for construction of different AAD fusion proteins with one or two albumin-binding domain/peptide/protein(s) in three-dimensional structure. One or two albumin-binding domain/peptide/protein(s) can be fused to ADI to form the AAD fusion protein. The position of albumin-binding domain/peptide/protein is far from the ADI active site. The albumin-binding domain/peptide/protein can be fused to the N-terminus or/and C-terminus of ADI. The structure in this figure is based on the *Mycoplasma arginini* ADI structure (Protein Data Bank: 1LXY). (A) Native ADI; (B) AAD fusion protein with two ABD or ABD1; (C) AAD fusion protein with one ABD or ABD1 at N-terminus; (D) AAD fusion protein with one ABD or ABD1 at C-terminus.

The term "cancer stem cell" refers to the biologically distinct cell within the neoplastic clone that is capable of initiating and sustaining tumor growth in vivo (i.e. the cancer-initiating cell).

DETAILED DESCRIPTION OF THE INVENTION

Arginine is a semi-essential amino acid for humans and other mammals. It can be synthesized from citrulline via a two step process catalyzed by urea cycle enzymes argininosuccinate synthase (ASS) and argininosuccinate lyase (ASL). Arginine can be metabolized to ornithine by the enzyme arginase, and ornithine can be converted to citrulline by ornithine carbamoyltransferase (OTC) in the mitochondria. The citrulline can be utilized to synthesize arginine again. Normal cells do not typically require an exogenous supply of arginine for growth because of the abundant catalytic activity of ASS and ASL. In contrast, many types of cancers do not express ASS and are therefore auxotrophic for arginine. Their growth is solely dependent on arginine from circulation. Therefore, targeting circulating arginine by using arginine-degrading enzymes is a feasible strategy to inhibit ASS-negative tumor growth.

Arginine can be degraded by arginine deiminase (ADI). ADI converts arginine to citrulline and ammonia, the metabolites of the urea cycle. Unfortunately, ADI can only be found in prokaryotes e.g. *Mycoplasma* sp. There are many problems associated with the isolation and purification of arginine deiminase from prokaryotes. ADI isolated from *Pseudomonas putida* failed to exhibit efficacy in vivo because of its low enzymatic activity in neutral pH. ADI produced from *Escherichia coli* is enzymatically inactive and subsequently requires multiple denaturation and renaturation process which raised the subsequent cost of production. The plasma half-life of the native form of ADI is short (~4 hours) upon injection into human circulation [Ensor et al., Cancer Res. 62:5443-5450 (2002); Izzo et al., J. Clin. Oncol. 22:1815-1822 (2004)]. These shortcomings can be partially remedied by pegylation. Among various forms of pegylated ADI, ADI bound with PEG (molecular weight 20,000) via succinimidyl succinate (ADI-PEG 20) has been found to be an efficacious formulation. However, the activity of ADI after pegylation is greatly decreased (by ~50%) [Ensor et al., Cancer Res. 62:5443-5450 (2002); Wang et al., Bioconjug. Chem. 17:1447-1459 (2006)]. Also, the succinimidyl succinate PEG linker can easily be hydrolyzed and detached from the protein, causing immunogenic problems after a short period of use in the body. Therefore, there is a need for improved cancer-treatment compositions, particularly, improved cancer-treatment compositions with enhanced activity.

ADI isolated from *P. putida* failed to exhibit efficacy in vivo because it had little enzyme activity at a neutral pH and was rapidly cleared from the circulation of experimental animals. ADI derived from *Mycoplasma arginini* is described, for example, by Takaku et al, Int. J. Cancer, 51:244-249 (1992), and U.S. Pat. No. 5,474,928. However, a problem associated with the therapeutic use of such a heterologous protein is its antigenicity. The chemical modification of ADI from *Mycoplasma arginini*, via a cyanuric chloride linking group, with polyethylene glycol (PEG) was described by Takaku et al., Jpn. J. Cancer Res., 84:1195-1200 (1993). However, the modified protein was toxic when metabolized due to the release of cyanide from the cyanuric chloride linking group. In contrast, even for the ADI-PEG20, the PEG linker can easily be hydrolyzed and detached from the protein, causing immunogenic problems after a short period of use in the body. Therefore, there is a need for compositions which degrade non-essential amino acids and which do not have the problems associated with the prior art.

In many types of cancer including melanoma, pancreatic, colon, leukemia, breast, prostate, renal cell carcinoma and liver cancers, cancer cells are auxotrophic for arginine since they lack of expression of argininosuccinate synthetase (ASS), making them excellent targets for arginine depletion therapy. In this invention, albumin-binding arginine deiminase (AAD) fusion proteins have high activity with long half-lives for efficient depletion of arginine in cancer cells.

The size of the monomer for ADI is on the order of 45 kDa and it exists as dimer (on the order of 90 kDa) [Das et al., Structure. 12:657-667 (2004)]. A design for construction of an AAD fusion protein is shown in FIG. 1. One or two albumin-binding domain/peptide/protein(s) with or without linker(s), SEQ ID NO: 46-49, are fused to ADI to form the AAD fusion protein. It is noteworthy that the selection of one or two particular albumin-binding domain/peptide/protein(s) can be made depending upon the type of cancer tissue to be targeted, the desired size and half-life of the resulting fusion protein, and whether a domain or entire protein is selected. Further, the selected albumin-binding material may be the same or different. That is, a protein and a peptide can be fused, two proteins, two domains, a domain and a protein, etc., as long as the resultant molecule retains the activity of the ADI and is also able to bind serum albumin with neither function of one portion of the fusion protein being interfered with by the other portion of the fusion protein. The position of the albumin-binding domain/peptide/protein is far from the active site. The albumin-binding domain/peptide/protein can be fused to the N-terminus or/and C-terminus of ADI. There are different variants of ABD showing different or improved human serum albumin (HSA) affinities. Different variants of ABD can be constructed and can be fused to ADI. Some micro-organisms endowed with ADI (for example *Pseudomonas* sp) cannot be used, due to their potential pathogenicity and pyrogenicity. The source of ADI can be from, but not limited to, different microorganisms, e.g. *Mycoplasma* (e.g. *Mycoplasma arginini*, *Mycoplasma arthritidis*, *Mycoplasma hominis*), *Lactococcus* (e.g. *Lactococcus lactis*), *Pseudomonas* (e.g. *Pseudomonas plecoglossicida*, *Pseudomonas putida*, *Pseudomonas aeruginosa*), *Streptococcus* (e.g. *Streptococcus pyogenes*, *Streptococcus pneumoniae*), *Escherichia*, *Mycobacterium* (e.g. *Mycobacterium tuberculosis*) and *Bacillus* (e.g. *Bacillus licheniformis*, *Bacillus cereus*). It is preferred that ADI is cloned from *Mycoplasma arginini*, *Lactococcus lactis*, *Bacillus licheniformis*, *Bacillus cereus*, thermophilic *Aspergillus fumigatus* or any combination thereof. Their amino acid sequences with SEQ ID (SEQ ID NO: 23-35) and the sequence alignment for some of the amino acid sequences in FIG. 2 are disclosed herein and also in the literatures [Das et al., Structure. 12:657-667 (2004); Wang et al., Bioconjug. Chem. 17:1447-1459 (2006); Ni et al., Appl. Microbiol. Biotechnol. 90:193-201 (2011); El-Sayed et al., Biotechnol Prog. 31(2):396-405 (2015)], where the disclosure of the literatures are incorporated herein by reference in their entirety.

The design and amino acid sequence for (A) native *Mycoplasma arginini* ADI protein (SEQ ID NO: 23), (B) different AAD fusion proteins originated from the *Mycoplasma arginini* ADI (SEQ ID NO: 36-40) and (C) AAD fusion protein originated from the *Bacillus cereus* ADI (SEQ ID NO: 41) are shown in FIG. 3. Different AAD fusion proteins are successfully constructed. A linker is inserted between the albumin-binding protein and ADI in the AAD fusion protein in these embodiments.

Figure 4:
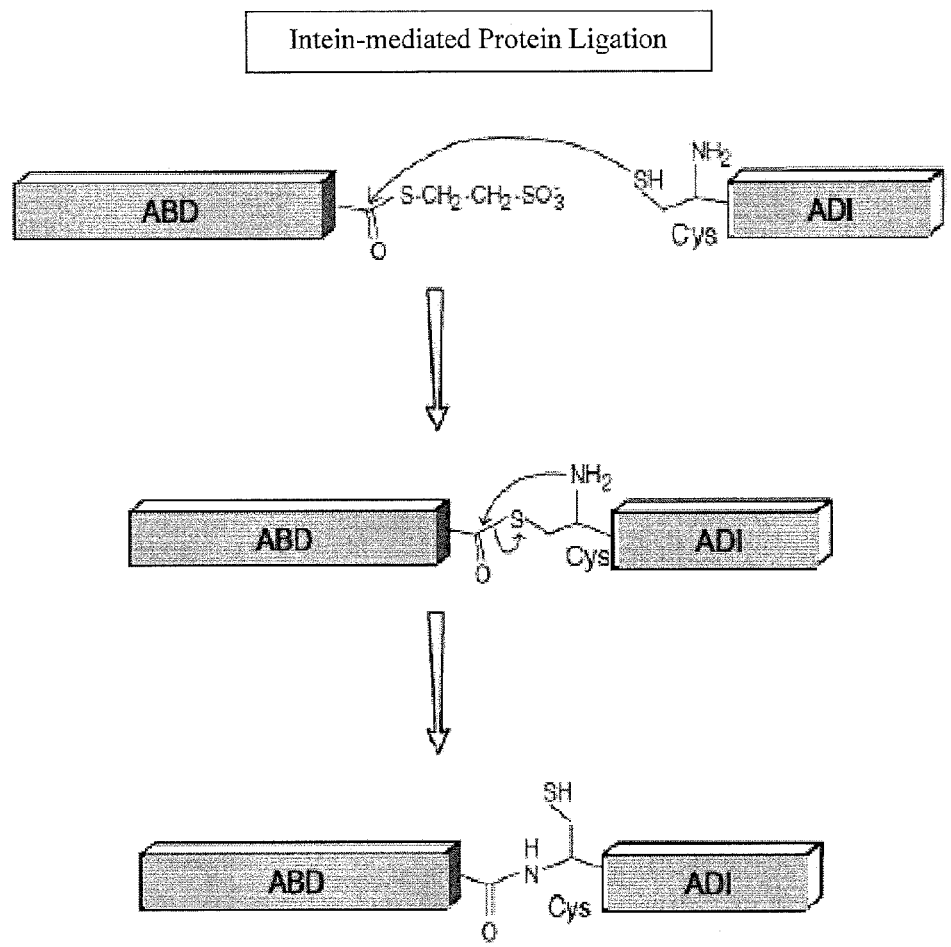
FIG. 4 shows the creation of AAD fusion protein in two embodiments (A) and (B) by the use of intein-fusion proteins and expressed protein ligation (CBD, chitin binding domain) under the following schemes; (C) C-terminal fusion; (D) N-terminal fusion; (E) Intein-mediated protein ligation.

On the other hand, a novel AAD fusion protein is also created by the use of intein-fusion proteins and expressed protein ligation (FIG. 4). The novel AAD fusion protein can be formed (1) by reacting the ADI having a N-terminal cysteine residue with a reactive thioester at C-terminus of the ABD, or (2) by reacting the ABD having a N-terminal cysteine residue with a reactive thioester at C-terminus of the ADI so that the ADI and the ABD are linked by a covalent bond. In FIG. 4E, ADI with N-terminal cysteine residue reacts with reactive thioester at the C-terminus of ABD. The thioester tag at the C-terminus of ABD, and an α-cysteine at the N-terminus of ADI are required to facilitate protein ligation. These fragments are produced using a pTWIN1 vector (New England Biolabs) according to the manufacturer's manual. In particular, the gene coding for the ABD-Intein-CBD fusion protein is synthesized and it is cloned into the vector under the control of T7 promoter for expression in *E. coli* (FIG. 4C). The ABD-Intein-CBD fusion protein produced binds to chitin in a column. The amino acid sequence of ABD-Intein-CBD (SEQ ID NO: 42) is shown in FIG. 4A. After thiol-inducible cleavage and elution from the column, the ABD with reactive thioester at its C-terminus is obtained (FIG. 4C). On the other hand, the gene coding for the CBD-Intein-ADI fusion protein is synthesized and cloned into the vector under the control of the T7 promoter for expression in *E. coli* (FIG. 4D). The CBD-Intein-ADI fusion protein produced binds to chitin in a column. The amino acid sequence of the CBD-Intein-ADI (SEQ ID NO: 43) is shown in FIG. 4B. After cleavage at pH 7 and 25° C., and elution from the column, the ADI with α-cysteine at its N-terminus is obtained (FIG. 4D). Finally, the AAD fusion protein is produced by the protein ligation reaction as shown in FIG. 4E.

Figure 9:
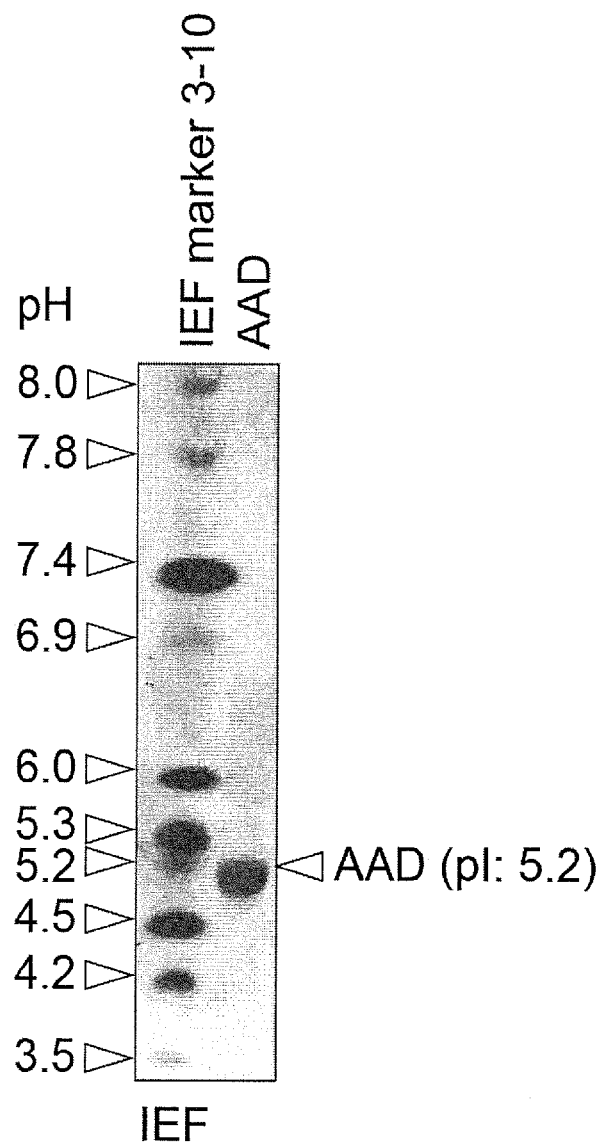
FIG. 9 shows the isoelectric point of AAD fusion protein in a pH 3-7 IEF protein gel.

Importantly, AAD fusion proteins can be produced and purified in a convenient manner. For example, an AAD fusion protein is successfully expressed and purified from *E. coli* both in soluble fraction and insoluble fraction, and this result is shown in FIG. 8. Furthermore, FIG. 8 shows the purified AAD fusion protein analyzed by sodium dodecyl sulfate polyacrylamide gel electrophoresis (SDS-PAGE). The size of the purified AAD fusion protein is determined as 52.8 kDa. The isoelectric point of wild-type ADI is 4.7 and the purified AAD fusion protein is about 5.2 (as shown in FIG. 9).

The pharmaceutical composition of the present invention contains AAD fusion protein with high activity for depleting arginine in tumor cells for cancer treatment. The specific activity of the purified AAD fusion protein is found to be similar to that of the wild-type ADI. The inhibitory effect of the AAD fusion protein on a panel of human cancer cell lines is therefore examined using MTT assay. Different cancer cells are seeded in 96-well plates and allowed to grow for 24 h for acclimatization. The cells are then incubated with 0-10 µg/ml of AAD for 72 hours. $IC_{50}$ is the half maximal inhibitory concentration, that is, it represents the concentration of AAD fusion protein that is required for 50% inhibition of a cancer cell line. The $IC_{50}$ is a measure of the effectiveness of a drug. The $IC_{50}$ of AAD fusion protein (amino acid sequence is shown in SEQ ID NO: 40, FIG. 3E) for different cancer cell lines (human melanoma, A375 & SK-mel-28; human colorectal cancer, HCT116; human pancreatic cancer, PancI & Mia-paca-2; human liver cancer, Sk-hep1; human cervical cancer, C-33A; human breast cancer, MDA-MB-231; human prostate cancer, 22Rv1; and human leukemia, Jurkat) is shown in TABLE 1.

TABLE 1

| Cancer cell line (argininosuccinate synthetase-negative, $ASS^{-ve}$) | $IC_{50}$ of AAD (µg/ml) |
| --- | --- |
| A375 (human melanoma) | 0.104 |
| SK-mel-28 (human melanoma) | 1.92 |
| PancI (human pancreatic cancer) | 0.043 |
| Mia-paca-2 (human pancreatic cancer) | 0.010 |
| Sk-hep1 (human liver cancer) | >10 |
| C-33A (human cervical cancer) | 0.058 |
| HCT116 (human colorectal cancer) | 0.211 |
| MDA-MB-231 (human breast cancer) | 0.173 |
| 22Rv1 (human prostate cancer) | 0.235 |
| Jurkat (human leukemia) | 0.379 |

Figure 10:
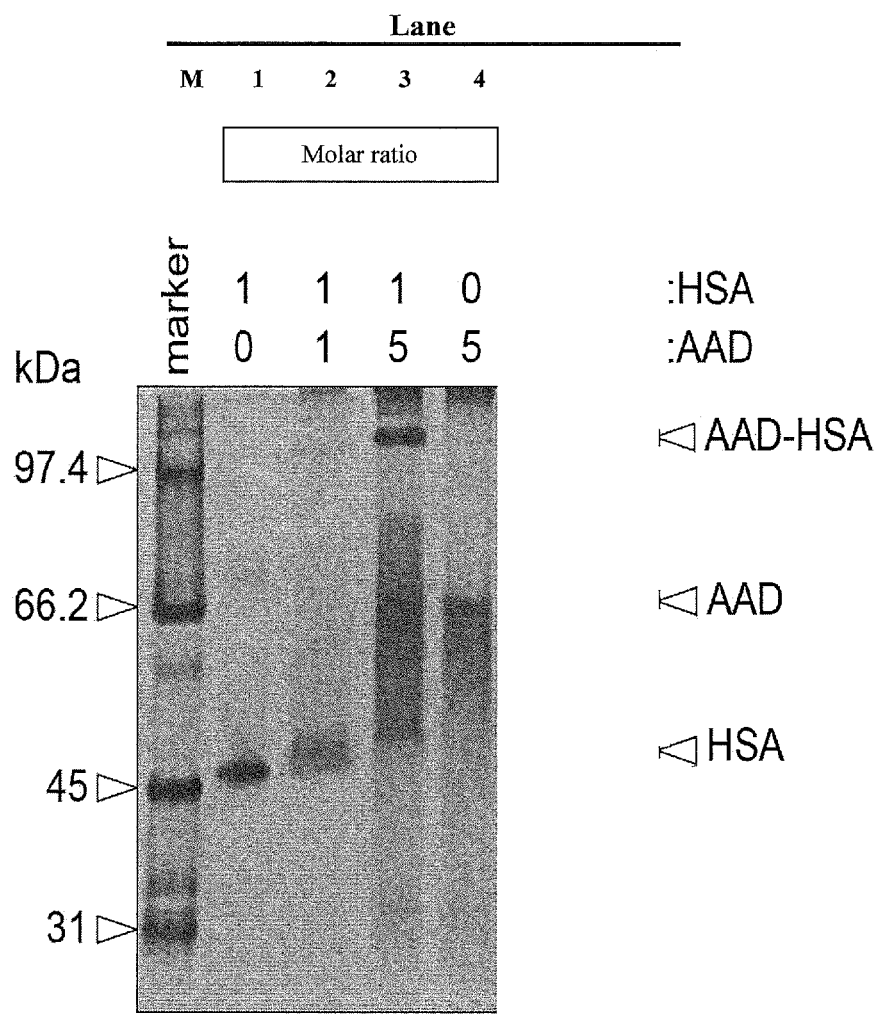
FIG. 10 shows the human serum albumin (HSA) binding of AAD. M: marker; Lane 1: HSA only; Lane 2: HSA:AAD ratio=1:1; Lane 3: HSA:AAD ratio=1:5; Lane 4: AAD only; Open Arrow: band of AAD, HSA, or AAD-HSA complexes.

For the albumin binding study, the present invention has demonstrated successfully that the engineered AAD fusion protein can bind to human serum albumin (HSA) or other animal serum albumin similar to HSA. FIG. 10 shows that the AAD fusion protein (amino acid sequence is shown in SEQ ID NO: 40, FIG. 3E) binds to HSA readily. AAD is incubated with the indicated molar ratio of HSA for 60 min at room temperature as shown in FIG. 10, lanes 1-4. After incubation, samples are subject to native polyacrylamide gel (10%). Lane 2 shows a partial binding of HSA in a 1:1 ratio while a complete binding of HSA is observed in a 1:5 (HSA:AAD) ratio in lane 3. At a mole ratio of 1:5 or 1:1 (i.e. lane 3 or 2 in FIG. 10), the formation of the HSA-AAD complex forms (~100-110 kDa) according to the construct of FIG. 1 using the linker molecule design. A band with molecular weight ~100 kDa representing the AAD-HSA complexes (indicated with an open arrowhead) is clearly observed in lane 3. It is expected that the circulating half-life of AAD fusion protein in the blood is increased by the non-covalent HSA-AAD complex formation. Therefore, a long-lasting version of AAD fusion protein has been successfully created.

No commercial products show high efficacy when compared to the AAD fusion protein-containing pharmaceutical composition prepared in this invention. For uses in cancer treatment, the AAD fusion protein-containing pharmaceutical composition of the present invention serves as an anti-cancer agent to deplete the arginine in tumor tissues. AAD fusion protein is a good candidate to be used in combination with other molecular targeting or cytotoxic agents.

The AAD fusion protein in the present invention can also be used as a component in a testing kit for detection of arginine in different samples. AAD has a small Km value; it indicates the high affinity for the substrate (arginine). Therefore, the rate will approach the maximum reaction rate more quickly. The AAD fusion protein can be used to testing arginine level (1) in cancer patients, (2) in a food sample, and (3) in cell culture.

EXAMPLES

The following examples are provided by way of describing specific embodiments of this invention without intending to limit the scope of this invention in any way.

Several of the Examples below relate to methods of making an albumin-binding arginine deiminase fusion protein. Various techniques can be used including cloning and intein-mediated protein ligation. As used herein, the term "cloning" is broadly used and comprises constructing a fusion gene coding for the albumin-binding arginine deiminase fusion protein, inserting the fusion gene into a vector, inserting the vector into a host organism and expressing a protein that includes an albumin-binding arginine deiminase fusion protein. Numerous variants on this technique can be performed and still fall within the cloning contemplated by the present invention.

Example 1

Construction of the Gene Coding for Albumin-Binding Domain/Peptide/Protein (ABD)

The gene coding for ABD is constructed by two rounds of PCR. In the first round, the PCR reaction mixture (total volume of 25 µl) contains the following materials:
1×iProof PCR buffer (Bio-Rad)
50 µM dNTP mixture
0.5 unit of iProof DNA Polymerase (Bio-Rad)
10 nM of each of the following oligos

```
ABD-F1 forward primer (SEQ ID NO: 01):
5'-CATGATGCGAATTCCTTAGCTGAAGCTAAAGTCTT
AGCTAACAGAGAACT-3'

ABD-R2 reverse primer (SEQ ID NO: 02):
5'-TAGTCACTTACTCCATATTTGTCAAGTTCTCTGTT
AGCTAAGACTTTAGC-3'

ABD-F3 forward primer (SEQ ID NO: 03):
5'-GAACTTGACAAATATGGAGTAAGTGACTATTACAA
GAACCTAATCAACAA-3'

ABD-R4 reverse primer (SEQ ID NO: 04):
5'-TACACCTTCAACAGTTTTGGCATTGTTGATTAGGT
TCTTGTAATAGTCAC-3'
```

```
-continued
ABD-F5 forward primer (SEQ ID NO: 05):
5'-GCCAAAACTGTTGAAGGTGTAAAAGCACTGATAGA
TGAAATTTTAGCTGC-3'

ABD-R6 reverse primer (SEQ ID NO: 06):
5'-AGCTACGATAAGCTTAAGGTAATGCAGCTAAAATT
TCATCTATCAGTG-3'
```

The following PCR program is used:
98° C. 30 s; 20 cycles of {98° C. 10 s, 50° C. 20 s, 72° C. 20 s}

In the second round of PCR, the PCR mixture (total volume of 50 µl) contains the following materials:
1×iProof PCR buffer (Bio-Rad);
50 µM dNTP mixture;
1 µl of PCR reactant as DNA template from the first round;
1 unit of iProof DNA Polymerase (Bio-Rad);
200 nM of each of the following oligos:

```
ABD-F7 forward primer (SEQ ID NO: 07):
5'-CATGATGCGAATTCCTTAGCTGAAGCTAAAGTCTT
AGCTAACAGAGAACT-3'

ABD-R8 reverse primer (SEQ ID NO: 08):
5'-AGCTACGATAAGCTTAAGGTAATGCAGCTAAAATT
TCATCTATCAGTG-3'
```

The following PCR program is used:
98° C. 30 s; 35 cycles of {98° C. 10 s, 60° C. 20 s, 72° C. 20 s}; 72° C. 5 min A PCR product containing the DNA sequence of ABD (169 bp) is obtained and purified by Qiagen DNA Gel Extraction Kit for cloning purpose.

Example 2A

Construction of the Fusion Gene Coding for the AAD Fusion Protein

In the first PCR, the PCR mixture (total volume of 50 µl) contains the following materials:
1×iProof PCR buffer (Bio-Rad);
50 µM dNTP mixture;
25 ng of *Mycoplasma arginini* genomic DNA;
1 unit of iProof DNA Polymerase (Bio-Rad);
200 nM of each of the following oligos:

```
ADINde-F forward primer (SEQ ID NO: 09):
5'-ATCGATCGATGTCTGTATTTGACAGTAAATTTAAAG
G-3'

ADIhis-R reverse primer (SEQ ID NO: 10):
5'-AGCTAAGGAATTCGCATCATGATGGTGATGGTGGTGG
CTACCCACTTAAC-3'
```

The following PCR program is used:
98° C. 1 min; 35 cycles of {98° C. 10 s, 50° C. 20 s, 72° C. 40 s}; 72° C. 5 min A PCR product of 1280 bp long is obtained and purified by Qiagen DNA Gel Extraction Kit. After that, the second PCR is performed. The PCR mixture (total volume of 50 µl) contains the following materials:
1×iProof PCR buffer (Bio-Rad);
50 µM dNTP mixture;
10 ng of the 1280 bp PCR product;
10 ng of the 169 bp PCR product;
1 unit of iProof DNA Polymerase (Bio-Rad);

200 nM of each of the following oligos:

```
ADINde-F forward primer (SEQ ID NO: 11):
5'-ATCGATCGATGTCTGTATTTGACAGTAAATTTAAAG
G-3'

ABD-R10 reverse primer (SEQ ID NO: 12):
5'-AGCTACGATAAGCTTAAGGTAATGCAGCTAAAATTT
CATCTATCAGTG-3'
```

The following PCR program is used:
98° C. 1 min; 35 cycles of {98° C. 10 s, 50° C. 20 s, 72° C. 45 s}; 72° C. 5 min A PCR product of 1428 bp is obtained and purified by Qiagen DNA Gel Extraction Kit. Then it is digested with restriction enzymes NdeI and HindIII, and ligated to plasmid pREST A (Invitrogen) that is predigested with the same enzymes. The ligation product is then transformed into *E. coli* BL21 (DE3) cells. The sequence of the constructed fusion gene is confirmed by DNA sequencing.

Example 2B

Cloning of His-ABD-PolyN-ADI

The construction of His-ABD-PolyN-ADI (SEQ ID NO: 40, in FIG. 3E) is done by two steps of overlapping PCR, the PCR fragment obtained from the last step is inserted into the vector pET3a between the NdeI and BamHI sites. The gene map, nucleotide sequence and amino acid sequence of His-ABD-PolyN-ADI are shown in FIG. 6.
Primers involved in construction of His-ABD-PolyN-ADI:

```
hisABDNde-F forward primer (SEQ ID NO: 13):
5'-GGAGATATACATATGCATCATCACCATCACCATGATGAAG
CCGTGGATG-3'

ABDnn-R1 reverse primer (SEQ ID NO: 14):
5'-TTGTTATTATTGTTGTTACTACCCGAAGGTAATGCAGCTA
AAATTTCATC-3'

ABDn-R2 reverse primer (SEQ ID NO: 15):
5'-AGAACCGCCGCTACCATTGTTATTATTGTTGTTACTACCC
GA-3'

ADln-F forward primer (SEQ ID NO: 16):
5'-AATAATAACAATGGTAGCGGCGGTTCTGTATTTGACAGTA
AATTTAAAGG-3'

ADIBam-R reverse primer (SEQ ID NO: 17):
5'-TAGATCAATGGATCCTTACCACTTAACATCTTTACGTGAT
AAAG-3'
```

In the first round of PCR, 50 µl of reaction volume containing the known concentration of components are prepared in two PCR tubes. In each of the tubes, dNTP, iProof buffer (BIO-RAD), iProof DNA polymerase (BIO-RAD), primers and DNA template are mixed and added up to 50 µl by ddH₂O. The DNA template used in the reaction is a pET3a vector containing the gene of ADI from *Mycoplasma arginini* with a removal of an internal NdeI site mutation without altering the protein sequence of the ADI gene.

The two reaction tubes contain the primer mixtures of (A) 10 pmol hisABDNde-F (SEQ ID NO: 13), 0.5 pmol ABDnn-R1 (SEQ ID NO: 14) and 10 pmol ABDn-R2 (SEQ ID NO: 15); and (B) 10 pmol ADIn-F (SEQ ID NO: 16) and 10 pmol ADIBam-R (SEQ ID NO: 17), respectively.

The PCR program is set according to the recommended steps in the manual with an annealing and extension temperature (time) at 50° C. (20 s) and 72° C. (40 s), respectively. The two products generated by PCR with the size of 237 bp and 1278 bp. The products are extracted and applied as template for the next round of PCR.

In the second overlapping step, the reaction mixture is prepared in a similar way to the first round except the template used was the mixture of 1 pmol of the 237 bp PCR product and 1 pmol of the 1278 bp PCR product from the first round PCR. Primers used are changed to 10 pmol hisABDNde-F (SEQ ID NO: 13) and 10 pmol ADIBam-R (SEQ ID NO: 17).

The annealing and extension temperature (time) are 50° C. (20 s) and 72° C. (60 s), respectively. A PCR product with the size of 1484 bp is generated from the reaction. The PCR product is purified and digested with NdeI and BamHI and then ligated into the pre-digested pET3a plasmid. The ligated product is then transformed into *E. coli* BL21 (DE3) for the production of recombinant protein.

Example 2C

Cloning of His-ABD-PolyN-bcADI

The construction of His-ABD-PolyN-bcADI (SEQ ID NO: 41, in FIG. 3F) is done by two steps of overlapping PCR, the PCR fragment obtained from the last step is inserted into the vector pET3a between the NdeI and BamHI sites. The gene map, nucleotide sequence and amino acid sequence of His-ABD-PolyN-bcADI are shown in FIG. 7.
Primers involved in construction of His-ABD-PolyN-bcADI:

```
hisABDNde-F2 forward primer (SEQ ID NO: 18):
5'-GGAGATATACATATGCATCATCACCATCACCATGATGAAGC
CGTGGATG-3' bcABDnn-R1 reverse primer (SEQ ID NO: 19):
5'-TTGTTATTATTGTTGTTACTACCCGAAGGTAATGCAGCTAA
AATTTCATC-3' bcABDn-R2 reverse primer (SEQ ID NO: 20):
5'-TTTACCGCCGCTACCATTGTTATTATTGTTGTTACTACCCG
A-3' bcADln-F forward primer (SEQ ID NO: 21):
5'-AATAATAACAATGGTAGCGGCGGTAAACATCCGATACATGT
TACTTCAGA-3' bcADIBam-R reverse primer (SEQ ID NO: 22):
5'-TAGATCAATGGATCCCTAAATATCTTTACGAACAATTGGCA
TAC-3'
```

In the first round of PCR, 50 µl of reaction volume containing the known concentration of components are prepared in two PCR tubes. In each of the tubes, dNTP, iProof buffer (BIO-RAD), iProof DNA polymerase (BIO-RAD), primers and DNA template are mixed and added up to 50 µl by ddH₂O. The DNA template used in the reaction is a pET3a vector containing the gene of ADI from *Bacillius cereus* with a removal of an internal NdeI site mutation without altering the protein sequence of the ADI gene.

The two reaction tubes contain the primer mixtures of (A) 10 pmol hisABDNde-F2 (SEQ ID NO: 18), 0.5 pmol bcABDnn-R1 (SEQ ID NO: 19) and 10 pmol bcABDn-R2 (SEQ ID NO: 20); and (B) 10 pmol bcADIn-F (SEQ ID NO: 21) and 10 pmol bcADIBam-R (SEQ ID NO: 22), respectively. The PCR program is set according to the recommended steps in the manual with an annealing and extension temperature (time) at 50° C. (20 s) and 72° C. (40 s), respectively. The two products are generated by PCR with the size of 237 bp and 1250 bp. The products are extracted and applied as template for the next round of PCR.

In the second overlapping step, the reaction mixture is prepared in a similar way to the first round except the template used is the mixture of 1 pmol of the 237 bp PCR product and 1 pmol of the 1250 bp PCR product from the first round PCR. Primers used are changed to 10 pmol hisABDNde-F2 (SEQ ID NO: 18) and 10 pmol bcADI-Bam-R (SEQ ID NO: 22).

The annealing and extension temperature (time) are 50° C. (20 s) and 72° C. (60 s), respectively. A PCR product with the size of 1512 bp is generated from the reaction. The PCR product is purified and digested with NdeI and BamHI and then ligated into the pre-digested pET3a plasmid. The ligated product is then transformed into E. coli BL21 (DE3) for the production of recombinant protein.

Example 3

Figure 5:
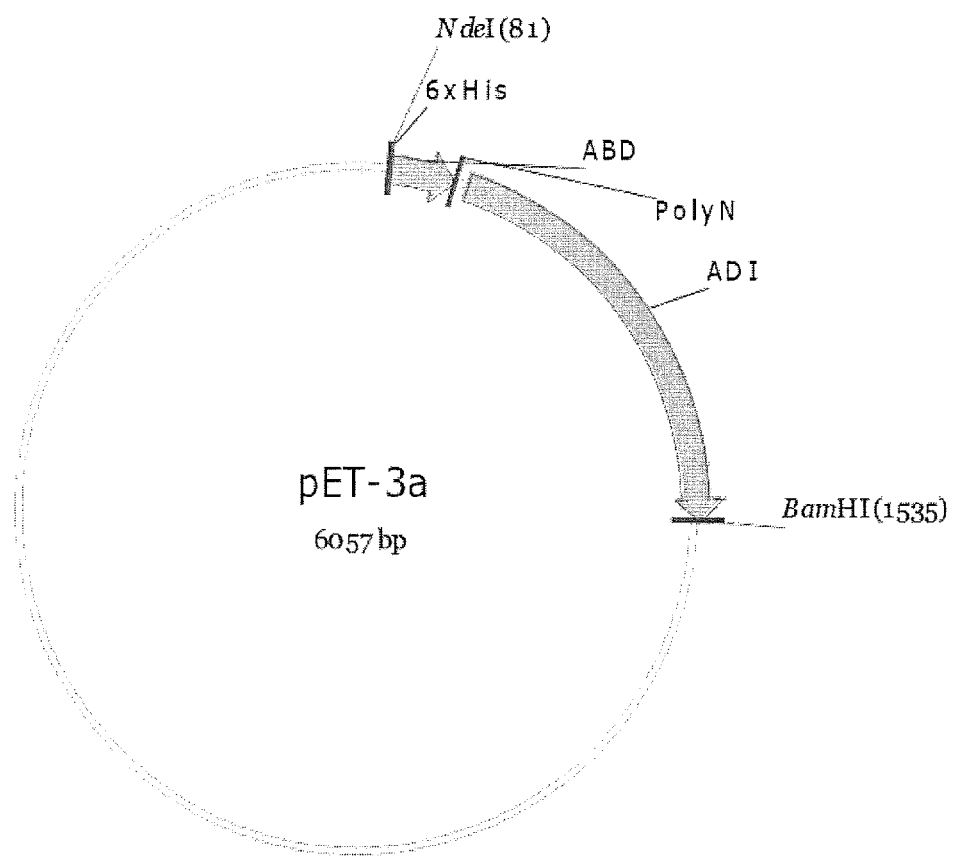
FIG. 5 shows the plasmid map of the expression vector constructed for producing AAD fusion protein.

Expression and Purification of the AAD Fusion Protein (3a) Expression of the AAD Fusion Protein by Shake-Flask Method For preparing the seed culture, the strain E. coli BL21 (DE3) carrying the plasmid encoding the AAD fusion protein (FIG. 5) is cultured in 5 ml of 2×TY medium, 30° C., 250 rpm, overnight. The overnight seed culture (2.5 ml) is added to 250 ml of 2×TY, 37° C., 250 rpm, 2.5 h (until $OD_{600} \approx 0.6$-$0.7$). When the $OD_{600}$ reached, IPTG is added to the culture (0.2 mM final concentration). The growth is continued for 22 more hours at 20° C. and then the cells are collected by centrifugation. The cell pellet is resuspended in 25 ml of 10 mM sodium phosphate buffer, pH 7.4. The cells are lysed by sonication.

(3b) Expression of the AAD Fusion Protein by Fermentation Method

For the seed culture, the aliquot of bacteria stock is inoculated into 50 ml of seeding medium (containing 1.5 g of yeast extract and 0.25 g of NaCl) with ampicillin and grown at 30° C. for 16 hr with continuous shaking at 250 rpm. The seed culture is then added to 1.25 L of medium (pH 7.4, containing yeast extract, tryptone, $Na_2HPO_4$, $KH_2PO_4$, $(NH_4)_2SO_4$, glycerol, glucose, $MgSO_4.7H_2O$, Thiamine-HCl and $CaCl_2$) supplement with trace element in the BIOSTAT fermentor system and grown at 28° C. Until the $OD_{600}$ of the culture reaches ~20, IPTG is added to a final concentration of 0.2 mM. The culture is further incubated for 16 hr. During incubation, 500 ml of feeding medium (pH 7.4, containing yeast extract, tryptone, $NH_4Cl$, $(NH_4)_2SO_4$, glycerol and $MgSO_4.7H_2O$) supplement with trace element were applied at 0.5 ml/min. Aeration is regulated in order to maintain 20% of air saturation by varying the speed of stirring from 500 rpm to 2000 rpm. The bacteria are harvested by centrifugation. The cells are lysed by sonication or high pressure homogenizer.

(3c) Purification of the AAD Fusion Protein

The soluble portion is collected after centrifugation. The fusion protein (containing a His tag) is then purified by nickel affinity chromatography. TABLE 2 shows that cultivation temperature is an important factor in affecting the solubility of AAD fusion protein (amino acid sequence is shown in SEQ ID NO: 40, FIG. 3E) obtained from the expression host.

For isolating the soluble fraction of AAD fusion protein, the cell pellet is resuspended in 25 ml of 10 mM sodium phosphate buffer, pH 7.4. The cells are lysed by sonication or high pressure homogenizer. The soluble portion is collected after centrifugation. The AAD fusion protein (contains a His tag or without His tag) is then purified by nickel affinity chromatography and/or ion-exchange columns.

For isolating the insoluble fraction of AAD fusion protein, the cell pellet is resuspended in 25 ml of 20 mM Tris-HCl, pH 7.4, 1% TRITON X-100. The cells are lysed by sonication. The insoluble portion (inclusion bodies) is collected by centrifugation. The protein is unfolded by resuspending in 10 ml of 20 mM Tris-HCl, pH 7.4, 6 M Guanidine HCl, and vortexed until it becomes soluble. The protein is refolded by adding the unfolded protein solution drop by drop into a fast stirring solution of 100 ml of 20 mM Sodium phosphate buffer, pH 7.4. The insoluble materials are removed by centrifugation. Salting out of the protein is performed by adding solid ammonium sulphate powder into the supernatant to achieve 70% saturation. The insoluble portion is collected by centrifugation and it is resuspended in 10 ml of 20 mM sodium phosphate buffer. The AAD fusion protein (contains a His tag or without His tag) is then purified by nickel affinity chromatography and/or ion-exchange columns.

TABLE 2

|  | AAD | | |
| --- | --- | --- | --- |
|  | 1 | 2 | 3 |
| Cultivation temperature (° C.) | 30 | 20 | 37 |
| Yield (mg)/ 250 ml culture | ~0.66 | ~12.0 | ~7.0 |
| solubility | 50% soluble | 90% soluble | 90% inclusion body |
| $IC_{50}$ (μg/ml) on A375 cells | 0.10 | 0.68 | 0.23 |

"90% inclusion body" means 90% of the AAD fusion protein produced in the bacterial cells are not soluble.

The yield and the enzyme activity of AAD fusion protein from shake-flask method and fermentation method are shown in TABLE 3.

TABLE 3

|  | AAD Yield (mg/L) | Activity (U/mg) |
| --- | --- | --- |
| Shake-flask method | ~10 | ~9 |
| Fermentation method | ~42 | ~19 |

Example 4

Enzyme Activity Assay and Enzyme Kinetics for AAD Fusion Protein

To determine the enzyme activity for wild-type ADI and AAD fusion protein in the present invention, the diacetyl monoxime (DAM)-thiosemicarbazide (TSC) assay for citrulline detection is used. The reaction is shown below.

L-Arginine  L-Citrulline+Ammonia

This assay is run by adding sample to a color reagent, which is made by mixing acidic ferric chloride solution with DAM-TSC solution. Briefly, enzyme is incubated with 20 mM arginine, 10 mM sodium phosphate pH 7.4 for 5 min at 37° C. The reaction mixture is heated at 100° C. for 5 mM to develop the color and read at 540 nm (light path=1 cm). A standard curve is constructed using various concentrations of citrulline. One unit of the ADI native enzyme is the amount of enzyme activity that converts 1 μmol of arginine to 1 μmol of citrulline per minute at 37° C. under the assay conditions. The specific activities of wild-type ADI, pegylated ADI (Ensor et al., Cancer Res. 62:5443-5450, 2002) and AAD fusion protein in the present invention are about 20, 15 and 19 U/mg (at pH 7.4, physiological pH), respectively. The specific activities for wild-type ADI and AAD fusion protein at different pH values (in a range from pH 5.5 to 9.5) are also determined, and the optimum pH is at 6.5. Therefore, the results indicate that AAD fusion protein depletes arginine efficiently which is even better than pegylated ADI, as the fusion with albumin-binding protein does not affect enzyme activity of ADI.

The Michaelis constant $K_m$ is the substrate concentration at which the reaction rate is at half-maximum, and is an inverse measure of the substrate's affinity for the enzyme. A small $K_m$ indicates high affinity for the substrate, and it means that the rate will approach the maximum reaction rate more quickly. For determination of the enzyme kinetics or $K_m$ value, the activity of wild-type ADI and AAD fusion protein are measured under different concentration of substrate arginine (2000 μM, 1000 μM, 500 μM, 250 μM, 125 μM, 62.5 μM) at pH 7.4. The measured $K_m$ values of the AAD fusion protein shown in FIG. 3E (SEQ ID NO: 40, ADI protein is originated from *Mycoplasma arginini*) and AAD fusion protein shown in FIG. 3F (SEQ ID NO: 41, ADI protein is originated from *Bacillus cereus*) are 0.0041 mM and 0.132 mM respectively. The results suggest that the fusion to ABD did not affect the binding affinity of the different AAD fusion proteins to arginine.

Example 5

Cell Proliferation Assay and In Vitro Efficacy of AAD Fusion Protein on Cancer Cell Lines Culture medium DMEM is used to grow the human melanoma A375 & SK-mel-28 and pancreatic cancer Panc1 & Mia-paca-2 cell lines. The EMEM medium is used to culture the human liver cancer SK-hep, cervical cancer C-33A and colorectal cancer HCT116 cell lines. The RPMI-1640 medium is used to culture the human breast cancer MDA-MB-231, prostate cancer 22Rv1 and leukemia Jurkat cell lines. Cancer cells (2-5×10³) in 100 μl culture medium are seeded to the wells of 96-well plates and incubated for 24 hours. The culture medium is replaced with medium containing 0-10 μg/ml of AAD fusion protein. The plates are incubated for an additional 3 days at 37° C. in an atmosphere of 95% air/5% $CO_2$. MTT assay is performed to estimate the number of viable cells in the culture according to manufacturer's instructions. The amount of enzyme needed to achieve 50% inhibition of cell growth is defined as $IC_{50}$.

As shown in TABLE 1, the results indicate that AAD fusion protein depletes arginine efficiently and inhibits the growth of various types of human cancer cell lines in in vitro tissue culture studies. For example, human melanoma, human breast cancer, human colorectal cancer, human pancreatic cancer, human liver cancer, human prostate cancer, human leukemia and human cervical cancer, all have low values of $IC_{50}$ (see TABLE 1), as these cancer types are all inhibited by AAD fusion protein readily. As determined from the in vitro_data, AAD fusion protein would inhibit all cancer types that are arginine-dependent, for example, the argininosuccinate synthetase-negative ($ASS^{-ve}$) cancers.

Example 6

In Vivo Half-Life Determination of AAD Fusion Protein

Balb/c mice (5-7 weeks) are used in this study and they are allowed to acclimatize for a week before the experiment. Mice (n=3) are separated into four groups and injected with 0, 100, 500 or 1000 μg of AAD fusion protein (SEQ ID NO: 40, FIG. 3E) in 100 μl PBS intraperitoneally, respectively. Blood of each mouse is collected at 0 h and Day 1-7. Sera are obtained after centrifugation. The sera are then deproteinised and analyzed by amino acid analyzer for arginine.

Figure 11:
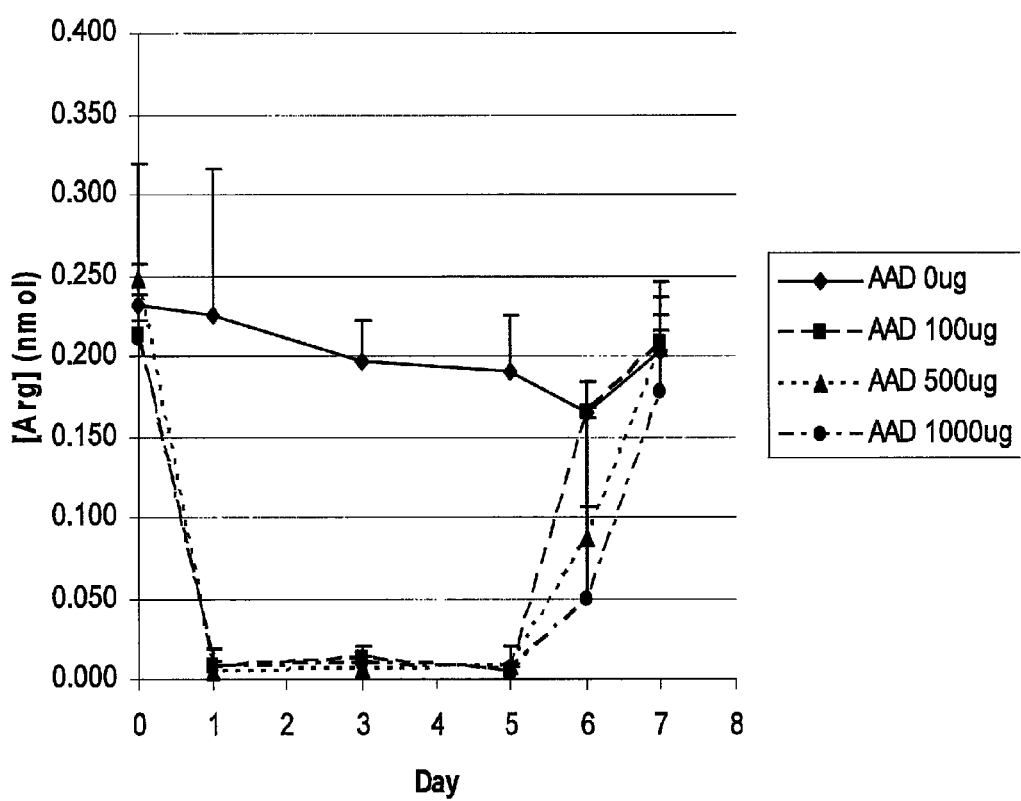
FIG. 11 is a graph showing the dose response of AAD fusion protein on plasma arginine levels in mice. A dose of 100 μg of AAD is sufficient to deplete plasma arginine for at least 5 days.

As shown in FIG. 11, AAD fusion protein (SEQ ID NO: 40, FIG. 3E), even at the lowest dosage of 100 μg, depletes plasma arginine efficiently at Day 1, 3 and 5, suggesting that AAD can deplete arginine in vivo efficiently for at least 5 days. The arginine level returns to normal gradually at Day 6 and Day 7 in all treatment groups.

Example 7

In Vivo Efficacy of Weekly Administration of AAD Fusion Protein on HCT 116 Colorectal Cancer Cell Xenografts Nude balb/c mice (5-7 weeks) are used in this study and they are allowed to acclimatize for a week before the experiment. Mice are inoculated subcutaneously with 2×10⁶ cancer cells in 100 μl of fresh culture medium. Ten days later, the mice are randomly separated into control and treatment group. Control group receives 100 μl PBS and treatment group receives 100 μl AAD fusion protein (amino acid sequence is shown in SEQ ID NO: 40, FIG. 3E) intraperitoneally weekly. Tumor size is measured by caliper and tumor volume is calculated using formula: (length× width²)/2. Blood draw are obtained at Day 5 after each treatment for plasma measurement of arginine.

Example 8

Comparison in In Vivo Efficacy Between Weekly and Biweekly Based Administration of AAD Fusion Protein on HCT 116 Colorectal Cancer Cell Xenograft Nude balb/c mice (4-6 weeks) are used and they are allowed to acclimatize for a week before the treatment. Mice are inoculated subcutaneously with 2×10⁶ cancer cells in 100 μl PBS. Ten days later, the mice are randomly separated into control and treatment groups. Control group receives 100 μl PBS and treatment group receives 200 μg AAD fusion protein (amino acid sequence is shown in SEQ ID NO: 40, FIG. 3E) in 100 μl PBS intraperitoneally weekly or biweekly. Tumor size is measured by caliper and tumor volume is calculated using formula: (length×width²)/2. In the weekly treatment group, blood draw are obtained at Day 0 and Day 5 of each treatment for plasma measurement of arginine. In the biweekly treatment group, blood draw are obtained just before the first treatment every week for plasma measurement of arginine. After the mice are sacrificed by end of the time course, the tumors are excised and weighed. The plasma arginine levels over the time course in the weekly treatment group are measured.

At Day 5, Day 12 and Day 19, the plasma arginine level is significantly decreased respectively after the weekly administration of the AAD fusion protein. Comparing the plasma arginine levels between Day 0, Day 7 and Day 14, the levels at Day 7 and Day 14 are relatively lower than that at Day 0, revealing that weekly administration of AAD fusion protein can decrease the overall plasma arginine levels over the time course. The tumor size in the weekly treatment group is lower than that in control at the end of the time course, revealing that the weekly administration of AAD fusion protein can reduce the tumor size of the xenograft in the disease mouse model. The difference in the tumor size between control and weekly treatment group is about 20% at Day 30.

The reduction in plasma arginine level is more significant in the biweekly treatment group than that in the weekly treatment group. The biweekly administration of AAD fusion protein does not affect the body weight of the mice over a 35-day time course as compared to the control. In conclusion, biweekly administration of AAD fusion protein in 400 μg per week (16 mg/kg/week/mouse) is more effective in completely suppressing plasma arginine level than weekly administration. Using the conversion of animal doses to human equivalent doses (HED) based on body surface area mentioned in "Guidance for Industry and Reviewers—Estimating the safe starting dose in clinical trials for therapeutics in adult healthy volunteers (2002)", human dose of the AAD fusion protein is about 1.3 mg/kg/week.

Example 9

In Vivo Efficacy of AAD Fusion Protein on Mia-Paca-2 Pancreatic Cancer Cell Xenografts Nude balb/c mice (4-6 weeks) are used and they are allowed to acclimatize for a week before the treatment. Mice are inoculated subcutaneously with $2 \times 10^6$ cancer cells in 100 μl of 1:1 PBS:Matrigel. Matrigel is used to augment the growth of tumors. Two weeks later, the mice are randomly separated into four groups of 4 animals in each group. Mice are intraperitoneally administered with PBS (control), AAD (5 U; twice a week), Gemcitabine, Gem (100 mg/kg; once a week) or AAD+Gem (a combination of both AAD and Gem) in 200 μl PBS. Tumor size is measured by caliper and tumor volume is calculated using formula: (length×width$^2$)/2. Body weight is measured every week. After the mice are sacrificed by end of the time course, the tumors are excised and weighed. The tumor size in all treatment groups is significantly lower than that in control at the end of the time course, revealing that the administration of AAD fusion protein can reduce the tumor size of the xenograft in the disease mouse model (shown in FIG. 12A, 12B, 12C). The difference in the tumor size between control and AAD fusion protein-treatment group is about 60% at Day 28. The treatment groups do not affect the body weight of the mice over a 28-day time course as compared to the control (shown in FIG. 12D).

Example 10

In Vivo Efficacy of AAD Fusion Protein on 22Rv1 Prostate Cancer Cell Xenografts Nude balb/c mice (4-6 weeks) are used and they are allowed to acclimatize for a week before the treatment. Mice are inoculated subcutaneously with $3 \times 10^6$ cancer cells in 100 μl PBS. Two weeks later, the mice are randomly separated into four groups of 5 animals in each group. Mice are intraperitoneally administered with PBS (control), AAD (5 U; twice a week), Docetaxel, DTX (10 mg/kg; once a week) or AAD+DTX (a combination of both AAD and DTX) in 200 ul PBS. Tumor size is measured by caliper and tumor volume is calculated using formula: (length×width$^2$)/2. Body weight is measured every week. After the mice are sacrificed by end of the time course, the tumors are excised and weighed.

Figure 13:
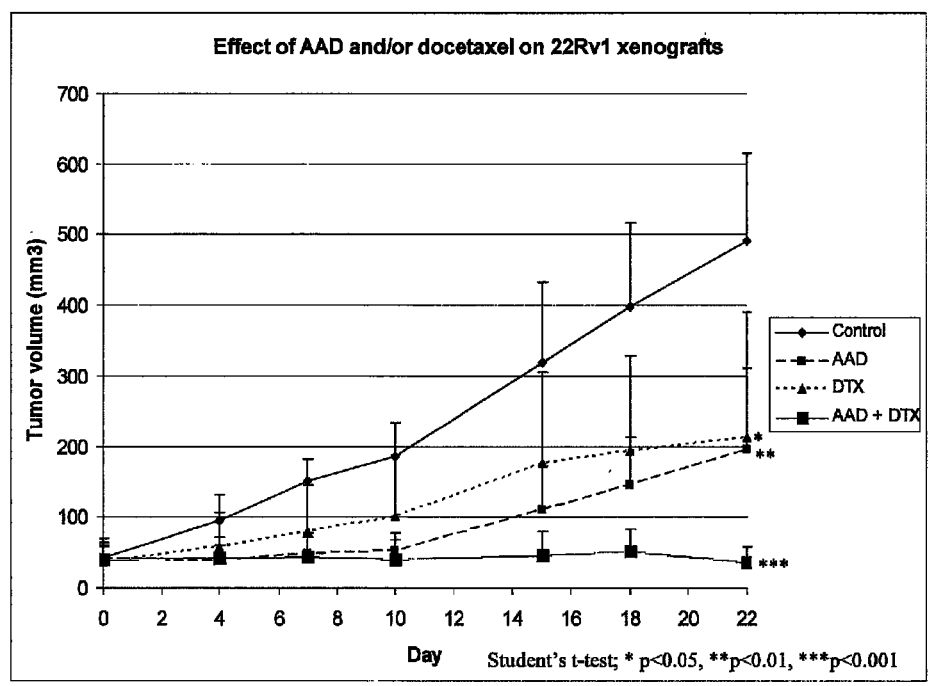
FIG. 13 shows the effects of administration of AAD fusion protein in total of 10 U per week and/or DTX on (A) tumor size; (B) appearance of the 22Rv1 prostate cancer xenograft and (C) tumor volume of the mice.

In FIG. 13A, the tumor size in all treatment groups is significantly lower than that in control at the end of the time course, revealing that the administration of AAD fusion protein or docetaxel can reduce the tumor size of the xenograft in the disease mouse model. The difference in the tumor size between control and AAD fusion protein- or DTX-treatment groups are about 55% and 54% at Day 22, respectively. Besides, the combination of AAD fusion protein and DTX-treatment group has a synergistic effect on tumor growth inhibition. Tumor growth of the combination treatment group is inhibited by about 94% when compared to that of the control group. FIG. 13B shows the appearance of the tumor tissues excised from xenografts at Day 22. AAD treatment does not affect the body weight of the mice over a 28-day time course.

Example 11

In Vivo Efficacy of AAD Fusion Protein on Jurkat Leukemia Xenografts

Figure 14:
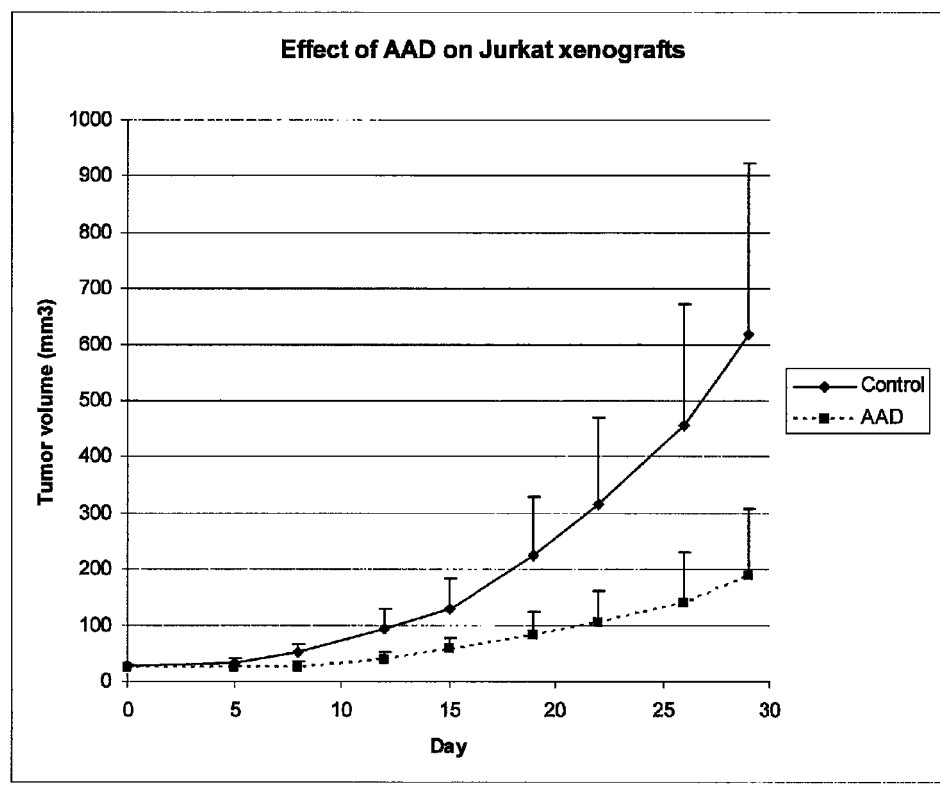
FIG. 14 shows the effects of administration of AAD fusion protein in total of 10 U per week of the Jurkat leukemia xenografts on tumor volume of the mice.

Nude balb/c mice (4-6 weeks) are used and they are allowed to acclimatize for a week before the treatment. Mice are inoculated subcutaneously with $5 \times 10^6$ cancer cells in 100 μl of 1:1 PBS:Matrigel. Matrigel is used to augment the growth of tumors. Since the take rate of this cancer cell line is relatively low, when certain tumor xenograft reaches a suitable size, the tumor is excised and cut into various pieces (~10 mm$^3$), which are further transplanted to the back of another group of mice subcutaneously. Ten days later, the mice are randomly separated into two groups of 8 animals in each group. Mice are intraperitoneally administered with PBS (control) or AAD (5 U; twice a week) in 200 μl PBS. Tumor size is measured by caliper and tumor volume is calculated using the following formula: (length×width$^2$)/2. Body weight is measured every week. At Day 28, the AAD fusion protein significantly inhibits the tumor growth when comparing to the control group (FIG. 14). The difference in tumor size between AAD fusion protein-treated and control groups becomes more significant at Day 30.

Example 12

Using AAD Fusion Protein in a Testing Kit

AAD fusion protein of the present invention has a small $K_m$, indicating the high affinity for the substrate (arginine). Therefore, the rate approaches the maximum reaction rate more quickly. To determine the concentration of arginine in a sample, AAD fusion protein in the present invention, the diacetyl monoxime (DAM)-thiosemicarbazide (TSC) assay for citrulline detection is used. The reaction is as follows: L-Arginine (of unknown concentration) is converted by AAD fusion protein to form L-Citrulline and Ammonia.

This assay is run by adding sample to a color reagent, which is made by mixing acidic ferric chloride solution with DAM-TSC solution. Briefly, arginine (in the sample, of unknown concentration) is incubated with 2-20 ng of the AAD fusion protein, and 10 mM sodium phosphate pH 7.4 for 5 mM at 37° C. The reaction mixture is heated at 100° C. for 5 mM to develop into pink color and read at 540 nm (light path=1 cm). A standard curve is constructed using various concentrations of citrulline. One unit of the AAD is the amount of enzyme activity that converts 1 µmol of arginine to 1 µmol of citrulline per minute at 37° C. under the assay conditions. This testing kit is very useful for the following applications:

Example 12A

Testing Arginine Level in Cancer Patients

For a cancer patient (human or animal), after treated with an arginine depleting drug, the arginine level (concentration) in blood should be very low or zero. A blood sample can be taken from the patient and then tested with this new testing kit based on the AAD fusion protein. After comparing to the standard curve (generated from standard solution plotted from known arginine concentration solutions), the exact arginine concentration of this blood sample of the patient can be measured. Therefore, this data helps monitor the progress of an arginine depletion treatment method. If the arginine level is too high (e.g. 200 micro-molar), more arginine depleting drug can be used on the patient to further keep the arginine at a lower or undetectable level so that the tumor can be inhibited by the systemic arginine depletion in the cancer patient.

Example 12B

Testing Arginine Level in a Food Sample

For industrial or food manufacturing purposes, the arginine (amino acid) level of a particular food material or intermediate during the food processing step might need to be monitored and measured. This arginine testing kit by using the AAD fusion protein of the present invention can measure the exact arginine concentration of a food sample prepared in solution form in the laboratory. This testing kit can also be used in high throughput manner and applicable for industrial scale and mass production.

Example 12C

Testing Arginine Level in Cell Culture

Nitric oxide (NO) is an important signaling molecule in cells and in the body. For many research projects on nitric oxide (NO) and cell culture studies, a lot of time a scientist would need to measure the amount or concentration of arginine (which is a substrate for making NO). This arginine testing kit by using the AAD fusion protein of the present invention can also be used for measuring the exact arginine concentration of any laboratory samples and/or analytical samples (e.g. for NO and cell culture studies).

What is claimed is:

1. A method of treating a cancer or inhibiting arginine-dependent tumor growth in a subject comprising administering an albumin-binding arginine deiminase fusion protein to the patient weekly or biweekly to reduce the availability of circulating arginine, wherein said albumin-binding arginine deiminase fusion protein comprises a first portion comprising one or two albumin-binding domain(s) fused to a second portion comprising arginine deiminase to form the albumin-binding arginine deiminase fusion protein, and one or more linker molecules; the first portion being positioned far from active site of the second portion by said linker molecule such that the albumin-binding arginine deiminase fusion protein retains the activity of arginine deiminase and binds serum albumin with neither function of one portion of the fusion protein being interfered with by the other portion of the fusion protein, wherein said albumin-binding arginine deiminase fusion protein comprises a sequence selected from SEQ ID NO: 36, 37, 38, 39, 40 or 41, and wherein said cancer consists essentially of pancreatic cancer, leukemia, melanoma, head and neck cancer, colorectal cancer, lung cancer, breast cancer, liver cancer, nasopharyngeal cancer, esophageal cancer, prostate cancer, stomach cancer and brain cancer.

2. The method of claim 1, wherein said cancer or arginine-dependent tumor growth is argininosuccinate synthetase-negative.

3. The method of claim 1, wherein the two albumin-binding domains of the first portion are the same.

4. The method of claim 1, wherein the two albumin-binding domains of the first portion are different from each other.

5. The method of claim 1, wherein said albumin-binding domain is SEQ ID NO: 46, 47, 48, or 49.

6. The method of claim 1, wherein the linker molecule comprises a sequence selected from SEQ ID NO: 50, 51, 52, 53, or serine-glycine-serine (SGS) amino acid sequence.

7. The method of claim 1, wherein the arginine deiminase is selected from arginine deiminase produced from a *Mycoplasma, Lactococcus, Pseudomonas, Streptococcus, Escherichia, Mycobacterium* or *Bacillus* microorganism.

8. The method of claim 1, wherein the arginine deiminase is produced from *Mycoplasma arginini, Lactococcus lactis, Bacillus licheniformis, Bacillus cereus, Mycoplasma arthritidis, Mycoplasma hominis, Streptococcus pyogenes, Streptococcus pneumoniae, Mycobacterium tuberculosis, Pseudomonas plecoglossicida, Pseudomonas putida, Pseudomonas aeruginosa*, thermophilic *Aspergillus fumigatus* or a combination thereof.

9. The method of claim 1, wherein said weekly or biweekly administering of said albumin-binding arginine deiminase fusion protein to said patient is 1.3 mg/kg/week.

10. The method of claim 1, wherein said albumin-binding arginine deiminase fusion protein is clinically effective in a pH range from 5.5 to 9.5.

11. The method of claim 1, wherein said albumin-binding arginine deiminase fusion protein is clinically effective at pH 7.4.

12. The method of claim 1, wherein said albumin-binding arginine deiminase fusion protein is clinically effective at pH 6.5.

13. The method of claim 11, wherein said albumin-binding arginine deiminase fusion protein has a specific activity of about 19 U/mg at pH 7.4.

14. The method of claim 1, wherein said albumin-binding arginine deiminase fusion protein is purified from both soluble and insoluble fractions of crude proteins.

* * * * *